US010792289B2

(12) United States Patent
Loutit et al.

(10) Patent No.: US 10,792,289 B2
(45) Date of Patent: *Oct. 6, 2020

(54) USE OF AEROSOLIZED LEVOFLOXACIN FOR TREATING CYSTIC FIBROSIS

(71) Applicant: Horizon Orphan LLC, Lake Forest, IL (US)

(72) Inventors: Jeffery S. Loutit, Los Altos, CA (US); Elizabeth E. Morgan, Escondido, CA (US); Michael N. Dudley, San Diego, CA (US); David C. Griffith, San Marcos, CA (US); Olga Lomovskaya, Mountain View, CA (US)

(73) Assignee: Horizon Orphan LLC, Lake Forest, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/263,886

(22) Filed: Jan. 31, 2019

(65) Prior Publication Data

US 2020/0000817 A1    Jan. 2, 2020

Related U.S. Application Data

(63) Continuation of application No. 15/623,168, filed on Jun. 14, 2017, now Pat. No. 10,231,975, which is a continuation of application No. 13/412,423, filed on Mar. 5, 2012, now Pat. No. 9,700,564, which is a continuation of application No. PCT/US2010/047903, filed on Sep. 3, 2010.

(60) Provisional application No. 61/249,231, filed on Oct. 6, 2009, provisional application No. 61/240,092, filed on Sep. 4, 2009.

(51) Int. Cl.
*A61K 31/5383* (2006.01)
*A61K 9/00* (2006.01)
*A61K 9/08* (2006.01)
*A61K 33/06* (2006.01)
*A61K 33/14* (2006.01)
*A61K 45/06* (2006.01)

(52) U.S. Cl.
CPC ........ *A61K 31/5383* (2013.01); *A61K 9/0078* (2013.01); *A61K 9/08* (2013.01); *A61K 33/06* (2013.01); *A61K 33/14* (2013.01); *A61K 45/06* (2013.01); *Y02A 50/401* (2018.01); *Y02A 50/469* (2018.01); *Y02A 50/47* (2018.01); *Y02A 50/471* (2018.01); *Y02A 50/473* (2018.01); *Y02A 50/475* (2018.01); *Y02A 50/478* (2018.01); *Y02A 50/481* (2018.01); *Y02A 50/483* (2018.01)

(58) Field of Classification Search
CPC .......... A61P 11/00; A61P 31/04; A61P 31/00; A61K 9/0078; A61K 31/5383; A61K 9/0073; A61K 47/02; A61K 45/06; A61K 31/536; A61K 33/06; A61K 31/4375; A61K 31/47; A61K 31/538; A61K 31/7036; A61K 9/08; A61K 33/14; A61K 9/0075; A61K 2300/00; A61K 47/26; A61K 9/5123; A61K 31/496; A61K 9/008; A61K 9/14; A61K 31/7034; A61K 31/7048; A61K 9/127; A61K 31/4164; A61K 31/4168; A61K 38/217; A61K 47/12; A61K 47/20; A61K 47/24; A61K 9/007; A61K 31/427; A61K 31/4709; A61K 9/145; A61M 15/08

See application file for complete search history.

(56) References Cited

U.S. PATENT DOCUMENTS

| | | |
|---|---|---|
| 2,587,215 A | 2/1952 | Priestly |
| 2,858,691 A | 11/1958 | Hoffman |
| 2,868,691 A | 1/1959 | Irving |
| 3,014,844 A | 12/1961 | Thiel |
| 3,456,644 A | 7/1969 | Thiel |
| 3,456,645 A | 7/1969 | Brock |
| 3,456,646 A | 7/1969 | Phillips |
| 3,507,277 A | 4/1970 | Altounyan |
| 3,565,070 A | 2/1971 | Hanson |
| 3,598,294 A | 8/1971 | Hedrick |
| 3,635,219 A | 1/1972 | Altounyan |
| 3,636,949 A | 1/1972 | Kropp |
| 3,669,113 A | 6/1972 | Altounyan |
| 3,732,864 A | 5/1973 | Thompson |
| 3,789,843 A | 2/1974 | Armstrong |

(Continued)

FOREIGN PATENT DOCUMENTS

| | | |
|---|---|---|
| BE | 0892357 | 7/1982 |
| CA | 2440412 A1 | 9/2002 |

(Continued)

OTHER PUBLICATIONS

"Fungal Lung Disease," In Breathing in America: Diseases, Progress, and Hope, chapter 9, pp. 92 and 95, published online in 2010 by the American Thoracic Society, accessed on Jan. 2, 2013 at http://www.thoracic.org/education/breaething-in-america/resources/chapter- -9-fungal-lung-disease.pdf.

(Continued)

*Primary Examiner* — Mark V Stevens

(74) *Attorney, Agent, or Firm* — Dennis A. Bennett; Brock D. Levin; Chris Marion

(57) ABSTRACT

Methods for treating cystic fibrosis. The method includes administering to a human in need thereof an aerosol solution comprising levofloxacin or ofloxacin and a divalent or trivalent cation. More particularly, the method includes administering the aerosol solution to a human having a pulmonary infection comprising *P. aeruginosa*.

8 Claims, 15 Drawing Sheets

(56) References Cited

U.S. PATENT DOCUMENTS

Figure 1A:
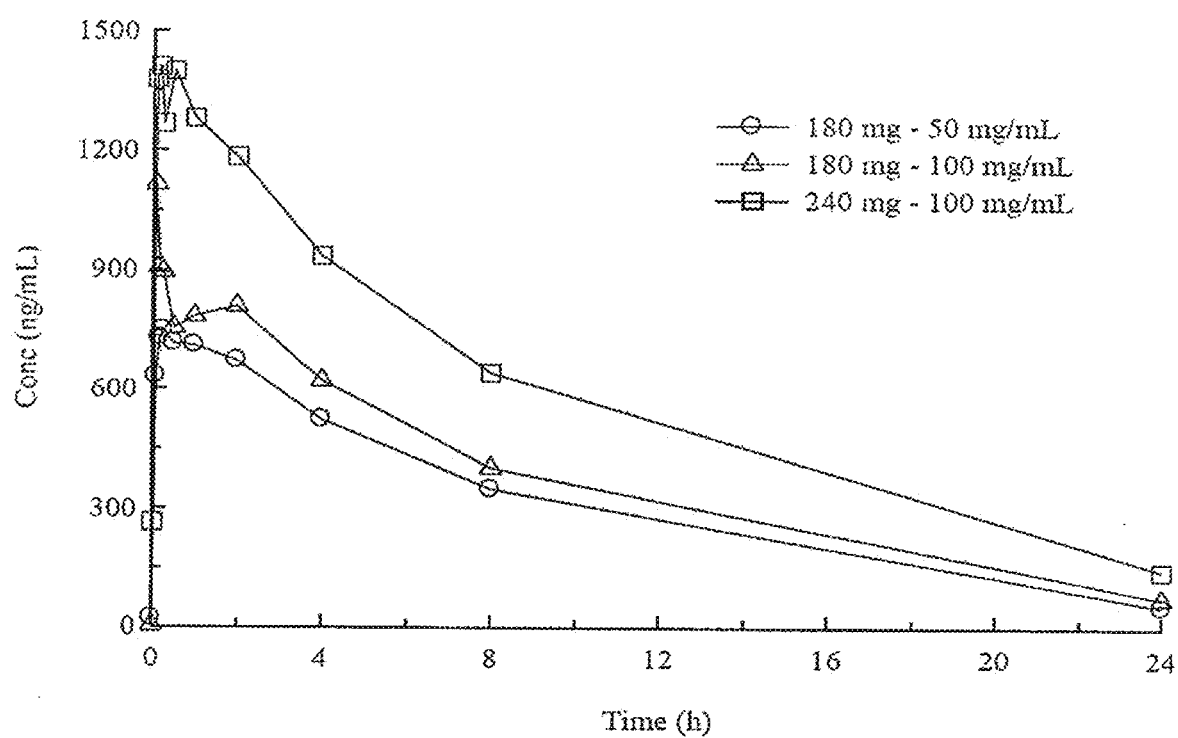
Figure 1B:
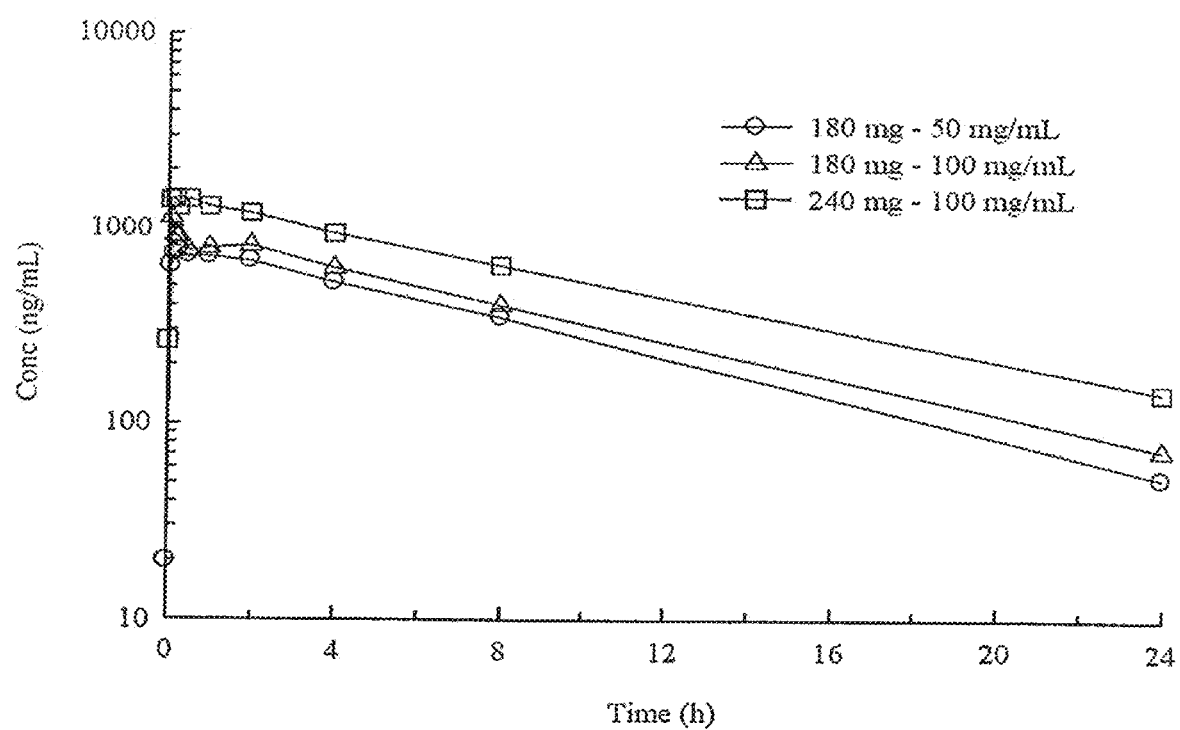
Figure 2A:
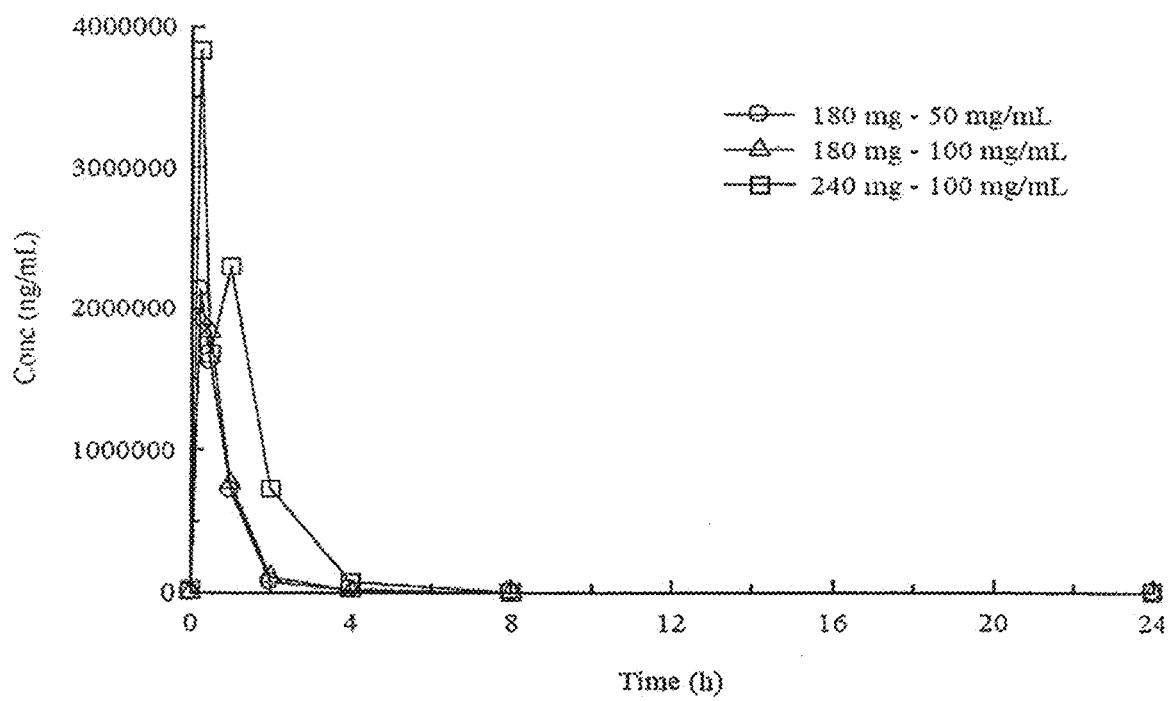
Figure 2B:
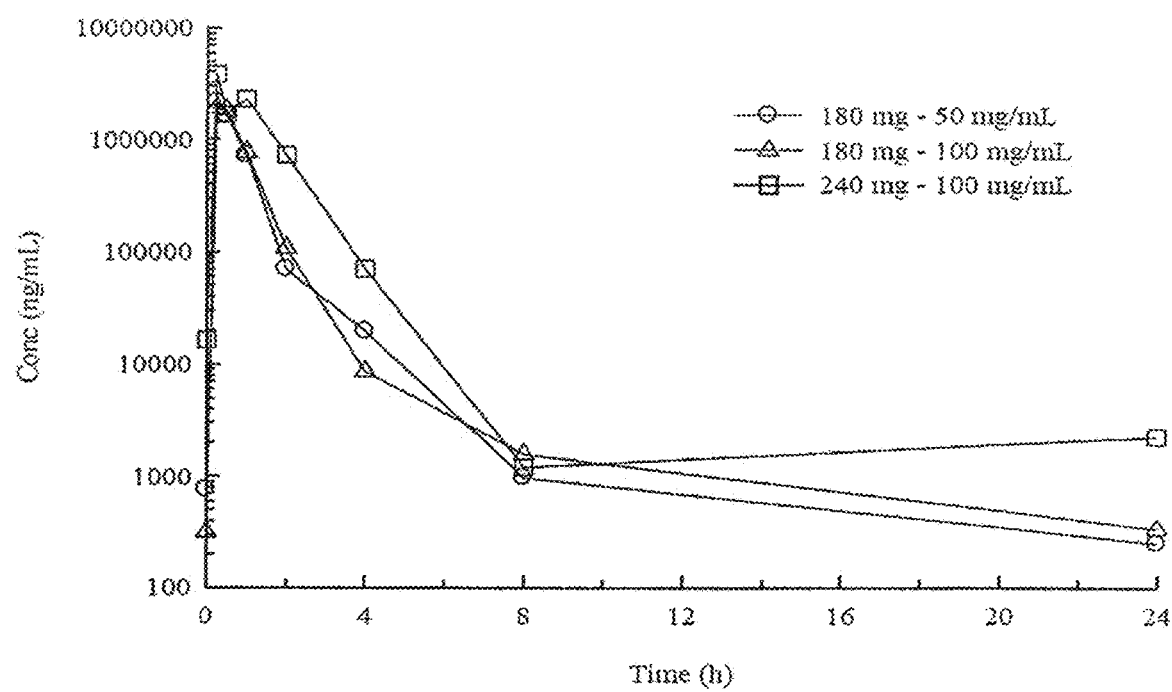

| | | |
|---|---|---|
| 3,807,400 A | 4/1974 | Cocozza |
| 3,826,255 A | 7/1974 | Havstad |
| 3,906,950 A | 9/1975 | Cocozza |
| 3,948,264 A | 4/1976 | Wilke |
| 3,971,377 A | 7/1976 | Damani |
| 3,991,761 A | 11/1976 | Cocozza |
| 4,013,075 A | 3/1977 | Cocozza |
| 4,046,146 A | 9/1977 | Rosskamp |
| 4,147,166 A | 4/1979 | Hansen |
| 4,253,468 A | 3/1981 | Lehmbeck |
| 4,263,907 A | 4/1981 | Lindsey |
| 4,268,460 A | 5/1981 | Boiarski |
| 4,353,365 A | 10/1982 | Hallworth |
| 4,382,892 A | 5/1983 | Hayakawa |
| 4,470,412 A | 9/1984 | Nowacki |
| 4,510,929 A | 4/1985 | Bordoni |
| 4,517,359 A | 5/1985 | Kobrehel |
| 4,534,345 A | 8/1985 | Wetterlin |
| 4,624,251 A | 11/1986 | Miller |
| 4,648,393 A | 3/1987 | Landis |
| 4,649,911 A | 3/1987 | Knight |
| 4,664,107 A | 5/1987 | Wass |
| 4,667,668 A | 5/1987 | Wetterlin |
| 4,688,218 A | 8/1987 | Blineau |
| 4,730,000 A | 3/1988 | Chu |
| 4,790,305 A | 12/1988 | Zoltan |
| 4,805,811 A | 2/1989 | Wetterlin |
| 4,807,814 A | 2/1989 | Douche |
| 4,809,692 A | 3/1989 | Nowacki |
| 4,811,731 A | 3/1989 | Newell |
| 4,832,015 A | 5/1989 | Nowacki |
| 4,844,902 A | 7/1989 | Grohe |
| 4,857,311 A | 8/1989 | Domb |
| 4,889,144 A | 12/1989 | Tateno |
| 4,907,538 A | 3/1990 | Helmle et al. |
| 4,926,852 A | 5/1990 | Zoltan |
| 4,955,371 A | 9/1990 | Zamba |
| 4,977,154 A | 12/1990 | Sanchez |
| 4,985,557 A | 1/1991 | Hayakawa |
| 4,994,599 A | 2/1991 | Chu |
| 5,012,803 A | 5/1991 | Foley |
| 5,012,804 A | 5/1991 | Foley |
| 5,024,467 A | 6/1991 | Truchet |
| 5,027,806 A | 7/1991 | Zoltan |
| 5,033,463 A | 7/1991 | Cocozza |
| 5,040,527 A | 8/1991 | Larson |
| 5,053,407 A | 10/1991 | Hayakawa |
| 5,060,643 A | 10/1991 | Rich |
| 5,113,855 A | 5/1992 | Newhouse |
| 5,119,806 A | 6/1992 | Palson |
| 5,142,046 A | 8/1992 | Hayakawa |
| 5,164,740 A | 11/1992 | Ivri |
| 5,217,004 A | 6/1993 | Blasnik |
| 5,284,133 A | 2/1994 | Burns |
| 5,304,559 A | 4/1994 | Rozier |
| 5,334,589 A | 8/1994 | Al-Razzak |
| 5,347,998 A | 9/1994 | Hodson |
| 5,364,838 A | 11/1994 | Rubsamen |
| 5,385,140 A | 1/1995 | Smith |
| 5,388,572 A | 2/1995 | Mulhauser |
| 5,404,781 A | 4/1995 | Chen |
| 5,404,871 A | 4/1995 | Goodman |
| 5,427,089 A | 6/1995 | Kraemer |
| 5,437,270 A | 8/1995 | Braithwaite |
| 5,478,578 A | 12/1995 | Arnold |
| 5,508,269 A | 4/1996 | Smith |
| 5,532,239 A | 7/1996 | Pruna |
| 5,549,102 A | 8/1996 | Lintl |
| 5,563,155 A | 10/1996 | Domagala |
| 5,586,550 A | 12/1996 | Ivri |
| 5,642,730 A | 7/1997 | Baran |
| 5,645,049 A | 7/1997 | Foley |
| 5,688,792 A | 11/1997 | Barbachyn |
| 5,694,920 A | 12/1997 | Abrams |
| 5,709,202 A | 1/1998 | Lloyd |
| 5,740,794 A | 4/1998 | Smith |
| 5,756,506 A | 5/1998 | Copeland |
| 5,758,637 A | 6/1998 | Ivri |
| 5,775,320 A | 7/1998 | Patton |
| 5,785,049 A | 7/1998 | Smith |
| 5,816,240 A | 10/1998 | Komesaroff |
| 5,820,873 A | 10/1998 | Choi |
| 5,823,179 A | 10/1998 | Grychowski |
| 5,829,434 A | 11/1998 | Ambrosio |
| 5,840,279 A | 11/1998 | Narodylo |
| 5,906,202 A | 5/1999 | Schuster |
| 5,918,594 A | 7/1999 | Asking |
| 5,934,272 A | 8/1999 | Lloyd |
| 5,960,792 A | 10/1999 | Lloyd |
| 5,971,951 A | 10/1999 | Ruskewicz |
| 5,988,160 A | 11/1999 | Foley |
| 6,003,512 A | 12/1999 | Gerde |
| 6,006,747 A | 12/1999 | Eisele |
| 6,026,807 A | 2/2000 | Puderbaugh |
| 6,026,809 A | 2/2000 | Abrams |
| 6,029,662 A | 2/2000 | Marcon |
| 6,070,575 A | 6/2000 | Gonda |
| 6,083,922 A | 7/2000 | Montgomery |
| 6,161,536 A | 12/2000 | Redmon |
| 6,192,876 B1 | 2/2001 | Denyer |
| 6,196,219 B1 | 3/2001 | Hess |
| 6,223,746 B1 | 5/2001 | Jewett |
| 6,230,706 B1 | 5/2001 | Gonda |
| 6,264,922 B1 | 7/2001 | Wood |
| 6,268,489 B1 | 7/2001 | Allen |
| 6,288,080 B1 | 9/2001 | Barsuhn |
| 6,294,178 B1 | 9/2001 | Weinstein |
| 6,333,044 B1 | 12/2001 | Santus |
| 6,333,045 B1 | 12/2001 | Yasueda |
| 6,338,443 B1 | 1/2002 | Piper |
| 6,349,719 B2 | 2/2002 | Gonda |
| 6,350,199 B1 | 2/2002 | Williams |
| 6,367,470 B1 | 4/2002 | Denyer |
| 6,406,880 B1 | 6/2002 | Thornton |
| 6,427,682 B1 | 8/2002 | Klimowicz |
| 6,435,177 B1 | 8/2002 | Schmidt |
| 6,468,967 B1 | 10/2002 | Oleson, Jr. |
| 6,492,328 B2 | 12/2002 | Lehrer |
| 6,503,953 B2 | 1/2003 | Vyden |
| 6,518,239 B1 | 2/2003 | Kuo |
| 6,523,536 B2 | 2/2003 | Fugelsang |
| 6,543,442 B2 | 4/2003 | Gonda |
| 6,544,555 B2 | 4/2003 | Rudnic |
| 6,557,549 B2 | 5/2003 | Schmidt |
| 6,561,186 B2 | 5/2003 | Casper |
| 6,576,224 B1 | 6/2003 | Osbakken |
| 6,579,854 B1 | 6/2003 | Mitchell |
| 6,584,971 B1 | 7/2003 | Denyer |
| 6,585,958 B1 | 7/2003 | Keller |
| 6,586,008 B1 | 7/2003 | Batycky |
| 6,601,581 B1 | 8/2003 | Babaev |
| 6,605,609 B2 | 8/2003 | Barbachyn |
| 6,608,078 B2 | 8/2003 | De Souza |
| 6,612,303 B1 | 9/2003 | Grychowski |
| 6,626,173 B2 | 9/2003 | Genova |
| 6,644,304 B2 | 11/2003 | Grychowski |
| 6,663,890 B2 | 12/2003 | Rudnic |
| 6,663,891 B2 | 12/2003 | Rudnic |
| 6,664,239 B2 | 12/2003 | Mitchell |
| 6,667,042 B2 | 12/2003 | Rudnic |
| 6,667,057 B2 | 12/2003 | Rudnic |
| 6,669,948 B2 | 12/2003 | Rudnic |
| 6,672,304 B1 | 1/2004 | Casper |
| 6,681,768 B2 | 1/2004 | Haaije De Boer |
| 6,689,769 B2 | 2/2004 | Gordeev |
| 6,716,819 B2 | 4/2004 | Welsh |
| 6,723,341 B2 | 4/2004 | Rudnic |
| 6,730,320 B2 | 5/2004 | Rudnic |
| 6,756,369 B2 | 6/2004 | Mitchell |
| 6,806,256 B2 | 10/2004 | Ulrich |
| 6,835,372 B2 | 12/2004 | Kuo |
| 6,838,552 B1 | 1/2005 | Mitchell |
| 6,869,965 B2 | 3/2005 | Gordeev |
| 6,878,713 B2 | 4/2005 | De Souza |

(56) References Cited

U.S. PATENT DOCUMENTS

| | | |
|---|---|---|
| 6,884,784 B1 | 4/2005 | Mitchell |
| 6,890,526 B2 | 5/2005 | Stratton |
| 6,962,151 B1 | 11/2005 | Knoch |
| 6,987,094 B2 | 1/2006 | Malvolti |
| 7,148,404 B2 | 12/2006 | Hoegenhaug |
| 7,838,532 B2 | 11/2010 | Surber |
| 7,893,020 B2 | 2/2011 | Glinka |
| 8,357,696 B2 | 1/2013 | Surber |
| 8,524,734 B2 | 9/2013 | Surber |
| 8,524,735 B2 | 9/2013 | Surber |
| 8,546,423 B2 | 10/2013 | Surber |
| 8,629,139 B2 | 1/2014 | Dudley |
| 8,815,838 B2 * | 8/2014 | Griffith ............... A61K 9/0078 |
| | | 514/210.15 |
| 9,326,936 B2 | 5/2016 | Griffith |
| 9,700,564 B2 * | 7/2017 | Loutit ............... A61K 9/0078 |
| 9,717,738 B2 * | 8/2017 | Griffith ............... A61K 9/0078 |
| 9,951,013 B2 | 4/2018 | Zankel |
| 1,014,985 A1 | 12/2018 | Griffith |
| 1,023,197 A1 | 3/2019 | Loutit |
| 10,231,975 B2 * | 3/2019 | Loutit ............... A61K 9/0078 |
| 10,308,607 B2 | 6/2019 | Zankel |
| 2001/0049366 A1 | 12/2001 | Singh |
| 2002/0061281 A1 | 5/2002 | Osbakken |
| 2002/0086867 A1 | 7/2002 | Dubois |
| 2002/0142050 A1 | 10/2002 | Straub |
| 2002/0197212 A1 | 12/2002 | Osbakken |
| 2003/0012814 A1 | 1/2003 | Rudnic |
| 2003/0028025 A1 | 2/2003 | Raghavan |
| 2003/0032600 A1 | 2/2003 | Ulrich |
| 2003/0078517 A1 | 4/2003 | Kensey |
| 2003/0138403 A1 | 7/2003 | Drustrup |
| 2003/0143265 A1 | 7/2003 | Araki et al. |
| 2003/0171340 A1 | 9/2003 | Isbister |
| 2003/0186894 A1 | 10/2003 | Kuo |
| 2004/0009126 A1 | 1/2004 | Pilkiewicz |
| 2004/0009989 A1 | 1/2004 | Niddam-Hildesheim |
| 2004/0014750 A1 | 1/2004 | Michaelis |
| 2004/0025876 A1 | 2/2004 | Miller |
| 2004/0037781 A1 | 2/2004 | McCormack, Jr. |
| 2004/0045546 A1 | 3/2004 | Hirsh |
| 2004/0152701 A1 | 8/2004 | Reddy |
| 2005/0036951 A1 | 2/2005 | Henderson |
| 2005/0106151 A1 | 5/2005 | Shapiro |
| 2005/0139211 A1 | 6/2005 | Alston |
| 2005/0147567 A1 | 7/2005 | Kuo |
| 2005/0208124 A1 | 9/2005 | Araki |
| 2005/0235987 A1 | 10/2005 | Smaldone |
| 2005/0260099 A1 | 11/2005 | Xia |
| 2005/0288302 A1 | 12/2005 | Niddam-Hildesheim |
| 2006/0003944 A1 | 1/2006 | Glinka |
| 2006/0025355 A1 | 2/2006 | Duddu |
| 2006/0062738 A1 | 3/2006 | Hofmann |
| 2006/0223751 A1 | 10/2006 | Mygind |
| 2006/0258677 A1 | 11/2006 | Amir |
| 2006/0276416 A1 | 12/2006 | Sinclair |
| 2006/0276463 A1 | 12/2006 | Sharma |
| 2006/0276473 A1 | 12/2006 | Bostion |
| 2006/0276483 A1 | 12/2006 | Surber |
| 2006/0276563 A1 | 12/2006 | Osterod |
| 2006/0286574 A1 | 12/2006 | Romesberg |
| 2007/0003753 A1 | 1/2007 | Asgari |
| 2007/0071686 A1 | 3/2007 | Lintz |
| 2007/0155715 A1 | 7/2007 | Van Duzer |
| 2007/0197548 A1 | 8/2007 | Murthy |
| 2007/0248693 A1 | 10/2007 | Mazzio |
| 2008/0276935 A1 | 11/2008 | Wang |
| 2009/0025713 A1 | 1/2009 | Keller |
| 2009/0197212 A1 | 8/2009 | Masen |
| 2009/0247458 A1 | 10/2009 | Watson |
| 2010/0037890 A1 | 2/2010 | Surber |
| 2010/0040560 A1 | 2/2010 | Surber |
| 2010/0087386 A1 | 4/2010 | Dudley |
| 2010/0087416 A1 * | 4/2010 | Griffith ............... A61K 9/0078 |
| | | 514/210.15 |
| 2010/0158957 A1 | 6/2010 | Surber |
| 2010/0166673 A1 | 7/2010 | Surber |
| 2010/0204470 A1 | 8/2010 | Wieser |
| 2012/0035166 A1 | 2/2012 | Dudley |
| 2012/0121593 A1 | 5/2012 | Levy |
| 2012/0237564 A1 * | 9/2012 | Dudley ............... A61K 9/0078 |
| | | 424/400 |
| 2012/0276153 A1 | 11/2012 | Loutit |
| 2014/0066441 A1 | 3/2014 | Surber |
| 2014/0105985 A1 | 4/2014 | Dudley |
| 2014/0329810 A1 | 11/2014 | Griffith |
| 2016/0279138 A1 | 9/2016 | Surber |
| 2016/0287606 A1 | 10/2016 | Griffith |
| 2017/0029376 A1 | 2/2017 | Zankel |
| 2018/0085462 A1 | 3/2018 | Dudley |
| 2019/0321371 A1 | 10/2019 | Griffith |
| 2019/0381057 A1 | 12/2019 | Surber |

FOREIGN PATENT DOCUMENTS

| | | |
|---|---|---|
| CA | 2739897 A1 | 4/2010 |
| CA | 2773033 A1 | 3/2011 |
| CN | 1312076 C | 4/2007 |
| CN | 101222927 A | 7/2008 |
| EP | 0047005 B1 | 3/1982 |
| EP | 206283 A2 | 12/1986 |
| EP | 0211595 A2 | 2/1987 |
| EP | 0298650 A2 | 1/1989 |
| EP | 0347779 A2 | 12/1989 |
| EP | 0455463 A1 | 11/1991 |
| EP | 0467172 A1 | 1/1992 |
| EP | 0470667 A1 | 2/1992 |
| EP | 0855183 A2 | 7/1998 |
| EP | 1092430 A1 | 4/2001 |
| EP | 1319399 A1 | 6/2003 |
| EP | 1459739 A1 | 9/2004 |
| EP | 1223915 | 12/2005 |
| EP | 2344129 A1 | 7/2011 |
| EP | 2346509 | 7/2011 |
| GB | 901107 A | 7/1962 |
| JP | 60202822 A | 10/1985 |
| JP | 63188627 A | 8/1988 |
| JP | 2003513046 A | 4/2003 |
| JP | 2003300882 A | 10/2003 |
| JP | 2004277431 A | 10/2004 |
| JP | 2004535370 A | 11/2004 |
| JP | 2008540676 A | 11/2008 |
| JP | 2009526003 A | 7/2009 |
| JP | 2012505222 A | 3/2012 |
| JP | 2012505223 A | 3/2012 |
| JP | 2013502416 A | 1/2013 |
| JP | 2013502579 A | 1/2013 |
| JP | 2013503907 A | 2/2013 |
| JP | 6099609 B2 | 3/2017 |
| RU | 2126000 C1 | 2/1999 |
| SU | 628930 A1 | 10/1978 |
| WO | 8705213 A1 | 9/1987 |
| WO | 9007351 A1 | 7/1990 |
| WO | 9013327 A1 | 11/1990 |
| WO | 9209322 A1 | 6/1992 |
| WO | 9312831 A1 | 7/1993 |
| WO | 9324165 A1 | 12/1993 |
| WO | 9507271 A1 | 3/1995 |
| WO | 9511666 A1 | 5/1995 |
| WO | 9623485 A1 | 8/1996 |
| WO | 9703649 A1 | 2/1997 |
| WO | 9723217 A1 | 7/1997 |
| WO | 9803217 A1 | 1/1998 |
| WO | 1999059566 | 11/1999 |
| WO | 9962495 A2 | 12/1999 |
| WO | 2000018388 | 4/2000 |
| WO | 2001002024 | 1/2001 |
| WO | 2001032181 | 5/2001 |
| WO | 0224167 A1 | 3/2002 |
| WO | 2002018345 | 3/2002 |
| WO | 0227167 A2 | 4/2002 |
| WO | 2002072102 | 9/2002 |
| WO | 03030868 A1 | 4/2003 |
| WO | 2003035030 | 5/2003 |

(56) References Cited

FOREIGN PATENT DOCUMENTS

| WO | 2003066064 | | 8/2003 |
|---|---|---|---|
| WO | 2003075889 | | 9/2003 |
| WO | 2004019912 | A2 | 3/2004 |
| WO | 2004069253 | A1 | 8/2004 |
| WO | 2005035036 | | 4/2005 |
| WO | 2005037256 | A2 | 4/2005 |
| WO | 2005089738 | A2 | 9/2005 |
| WO | 2006011051 | A1 | 2/2006 |
| WO | 2006033713 | A2 | 3/2006 |
| WO | 2006078925 | A2 | 7/2006 |
| WO | 2006100875 | A1 | 9/2006 |
| WO | 2006125132 | A2 | 11/2006 |
| WO | 2007085057 | A1 | 8/2007 |
| WO | 2007090123 | A2 | 8/2007 |
| WO | 2007090646 | A1 | 8/2007 |
| WO | 2007095156 | A2 | 8/2007 |
| WO | 2007095187 | A2 | 8/2007 |
| WO | 2008025560 | A1 | 3/2008 |
| WO | 2009044202 | A1 | 4/2009 |
| WO | 2009140587 | A1 | 11/2009 |
| WO | 2010042549 | A1 | 4/2010 |
| WO | 2010042553 | A1 | 4/2010 |
| WO | 2010124141 | A1 | 10/2010 |
| WO | 2011022074 | A1 | 2/2011 |
| WO | 2011022075 | A1 | 2/2011 |
| WO | 2011029059 | A1 | 3/2011 |
| WO | 2014032184 | | 3/2014 |

OTHER PUBLICATIONS

"Hypersensitivity Pneumonitis," by the American Lung Association, Retrieved from the Internet at http://www.lung.org/lung-disease/hypersensitivity-pneumonitis; 1 page, 2015.
"Physician's Desk Reference", 52.sup.nd ed., Medical Economics, Montvale, N.J. (1998).
"Understanding Sarcoidosis" by the American Lung Association. Retrieved from the Internet at http://www.lung.org/lung-disease/sarcoidosis/understanding-sarcoidosis.ht-ml; 4 pages, 2015.
Abusriwil et al. "The interaction of host and pathogen factors in chronic obstructive pulmonary disease exacerbations and their role in tissue damage", Proc. Am. Thorac. Soc. (2007) 4(8):611-617.
Aggarwal et al., "Predictors of mortality and resource utilization in cirrhotic patients admitted to the medical ICU," Chest, vol. 119, No. 5, (May 2001), pp. 1489-1497.
Ambrose, et al., "Pharmacokinetics-Pharmacodynamics of Antimicrobial Therapy: It's Not Just for Mice Anymore," Antimicrobial Resistance, vol. 44, (Jan. 1, 2007); pp. 79-86.
Amsden, "Anti-Inflammatory Effects of Macrolides—an Underappreciated Benefit in the Treatment of Community-Acquired Respiratory Tract Infections and Chronic Inflammatory Pulmonry Conditions? ", Journal of Antimicrobial Chemotherapy, 55:10-21, (2005).
Anonymous, "Mpex Candidate, MP-376, Granted U.S. Orphan Drug Status for the Treatment of Cystic Fibrosis", Medical News Today, Internet Citation, Mar. 5, 2008, 3 pages, XP002560239, Retreived from the Internet: URL: http://www.medicalnewstoday.com/articles/99488.php.
Anonymous, "MPEX Pharmaceuticals Initiates Multi-Dose Clinical Trial in the U.S. with MP-376 in Patients with Cystic Fibrosis" Science Letter (2007) 2 pages.
Anonymous, MP-376 safe and effective for treatment of P. aeruginosa in CF patients, May 16, 2010 at http://www.eurekalert.org/pub.sub.--releases/2010-05/ats-msa051010.php; 2 pages.
Araujo, et al., "Effect of Moxifloxacin on Secretion of Cytokines by Human Monocytes Stimulated with Lipopolysaccharide", Clin. Microbial. Infect., 8:26-30, (2002).
Araujo, et al., "Gemifloxacin Inhibits Cytokine Secretion by Lipopolysaccharide Stimulated Human Monocytes at the Post-Transcriptional Level", Clin. Microbial. Infect., 10:213-9, (2004).
Arzte, Zeitung De, www.aerztezeitunq.de/extras/druckansicht/?sid=347342&pid=351267 (retrieved online Dec. 11, 2009), XP002560241. (Machine Translation Provided); 6 pages.

Atkins et al., "The Design and Development of Inhalation Drug Delivery Systems", Pharmaceutical Inhalation Aerosol Technology, Marcel Dekker, Inc., New York, NY (1992) 6: p. 155-185.
Australian Patent Examination Report No. 1, corresponding to Australian Patent Application No. 2010289326, dated May 7, 2014; 4 pages.
Australian Patent Examination Report No. 1, corresponding to Australian Patent Application No. 2014203364, dated Jul. 6, 2015; 4 pages.
Australian Patent Examination Report No. 1, dated May 5, 2014, corresponding to to Australian Patent Application No. 2010238765; 4 pages.
Australian Patent Examination Report No. 1, dated Jul. 25, 2014, corresponding to Australian Patent Application No. 2009302478; 4 pages.
Australian Patent Examination Report No. 1, dated Jun. 9, 2015, corresponding to Australian Patent Application No. 2013203605; 4 pages.
Baker, et al., "A Prodrug Approach Toward the Deveolpment of Water Soluble Fluoroquinolnes and Structure-Activity Relationships of Quinolone-3-Carboxylic Acids", J. Med. Chem., 47:4693-709, (2004).
Banerjee et al., "The treatment of respiratory pseudomonas infection in cystic fibrosis: what drug and which way?" Drugs (2000) 60(5):1053-64. (Abstract Only).
Barry, et al., "Novel Agents in the Management of Mycobacterium Tuberculosis Disease", Current Medical Chemistry (Netherlands), 14(18):2000-8, (2007), (Abstract only).
Bartlett, J., "Overview of Pneumonia", Merck Manual Home Edition article accessed at<http:// www.merckmanuals.com/home/lung-and-airway-disorders/pneumonia/overview-of-pneumonia>; 5 pages.
Bartlett, Clinical Microbiology, "Anaerobic bacterial infection of the lung," Anaerobe 18 (Elsevier) (2012); pp. 235-239.
Battram, et al., "In Vitro and In Vivo Pharmacological Characterization of 5-[(R)-2(5,6-diethyl-indian-2ylamino)-1-hydroxy-ethyl]-8-hydroxy-1H-quinolin-2-one (indacterol), a Novel Inhaled Beta(2) Adrenoceptor Agonist with a 25-h Duration of Action", J. Pharmacol. Exp. Ther., 317(2):762-70, (2006), (Abstract only).
Beasley, et al., "Adverse Reactions to the Non-Drug Constituents of Nebuliser Solutions", Br. J. din. Pharmac., 25:283-7, (1988).
Benko, et al., "Pharmacokinetics and Pharmacodynamics of Levofloxacin in Critically Ill Patients with Ventilator-Associted Pneumonia", International Journal of Antimicrobial Agents (Netherlands), 30(2)162-8, (2007), (Abstract only).
Berg, "Combination products are spotlighted at Drug/Device Summit," Pulmonary drug delivery systems,The BBI Newsletter (May 1, 2005); 2 pages.
Bide, et al., "Allometric Respiration/Body Mass DAta for Animals to be Used for Estimates of Inhalation Toxicity to Young Adult Humans," Journal of Applied Toxicology, (J. Appl. Toxicol.) vol. 20, (2000); pp. 273-290.
Blaser et al., "Influence of Medium and Method on the In Vitro Susceptibility of Pseudomonas Aeruginosa and Other Bacteria to Ciprofloxacin and Enoxacin Antimicrobial Agents and Chemotherapy", American Society for Microbiology (1986) 29(5):927-929.
Blau, et al., "Moxifloxacin but not Ciprofloxacin or Azithromycin Selectively Inhibits IL-8, IL-6,ERK1/2, JNK, and NF-κB Activation in a Cystic Fibrosis Epithelial Cell Line," American Journal of Physiology—Lung Cellular and Molecular, vol. 292, (Jan. 2007); pp. L343-L352.
Blitz, et al., "Aerosolized Magnesium Sulfate for Acute Asthma: A Systematic Review", Chest the Cardiopulmonary and Critical Care Journal, 128(1):337-44, (Jul. 2005).
Boehnke, et al., "High-dose riboflavin treatment is efficacious in migraine prophylaxis: an open study in a tertiary care centre," European Journal of Neurology, vol. 11, (2004); pp. 475-477.
Braga, et al., Chem. Commun., "Making Crystals from Crystals: A Green Route to Crystal Engineering and Polymorphism", 3635-45, (2005).
Brouillard, et al., "Antibiotic Selection and Resistance Issues with Flouroquinolones and Doxycycline Against Bioterrorism Agents", Pharmacotherapy, Special Article, United States, 26(1):3-14, (2006).

(56) References Cited

OTHER PUBLICATIONS

Bryskier, "Bacillue anthracis and antibacterial agents," Clinical Microbiology and Infection—the official publication of the European Society of Clinical Microbiology and Infectious Diseases (France), vol. 8, No. 8, (2002) pp. 467-478.
Burger, Am. Preclinical Screening for New Anticancer Agents. Springer. 2014, p. 23.
Calbo, E. et al., "Systemic expression of cytokine production in patients with severe pneumococcal pneumonia: Effects of treatment with a beta-lactam versus a fluoroquinolone", Antimicrobial Agents and Chemotherapy, (2008), 52(7):2395-402, ISSN 0066-4804, XP002560242.
Canadian Office Action and Examination Search Report dated Aug. 11, 2015, corresponding to Candian Patent Application No. 2,739,897; 3 pages.
Canadian Office Action dated Jul. 29, 2014, corresponding to Canadian Application No. 2,608,273; 2 pages.
Canadian Office Action dated Jul. 31, 2015, corresponding to Canadian Patent Application No. 2,739,893; 3 pages.
Carratala, et al., "Clinical Experience in the Management of Community-Acquired Pneumonia: Lessons from the Use of Fluoroquinolones", Clinical Microbiology and Infection—The Official Publication of the European Society of Clinical Microbiology and Infectious Diseases (France), 12(3):2-11, (2006), (Abstract only).
Cazzola, et al., "Delivering antibacterials to the lungs: considerations for optimizing outcomes", Am. J. Respir. Med. (2002) 1(4):261-272.
Celli et al., "The body-mass index, airflow obstruction, dyspnea, and exercise capacity index in chronic obstructive pulmonary disease", N Engl J Med. (2004) 350(10):1005-1012.
Chang et al., "Properties of the Drug Molecule in Nasal Systemic Drug Delivery," 1989, pp. 49-51, Chapter 3, Marcel Dekker, Inc.
Chhabra, et al., "Evaluation of Three Scales of Dyspnea in Chronic Obstructive Pulmonary Disease," Annals of Thoracic Medicine, vol. 4, No. 3, (2009); pp. 128-132.
Chien, Yie W., et al., "Propeties of the Drug Molecule in Nasal Systemic Drug Delivery", Chapter 3, pp. 63-8, Marcel Dekker, Inc., (1989).
Chilean Office Action (no English translation), dated Mar. 5, 2014, corresponding to Chilean Patent Application No. 2011-002649; 9 pages.
Chilean Office Action (with no English translation), corresponding to Chilean Patent Application No. 00586-2012, dated Dec. 5, 2014; 8 pages.
Chilean Office Action; 9 pages.
Chilean Second Examination Report (No English translation), dated Jun. 1, 2015, corresponding to Chilean Patent No. 00586-2012; 4pages.
Chilean Second Examination Report (No English translation), dated Nov. 3, 2014, corresponding to Chilean Patent Application No. 2011-02649; 6 pages.
Chinese First Office Action, (with English translation) dated Apr. 6, 2010, corresponding to Chinese Patent Application No. 200680026156.0; 9 total pages.
Chinese Office Action (no English translation), dated Dec. 10, 2014, corresponding to Chinese Patent Application No. 200980142471.3; 3 pages.
Chinese Office Action (No English Translation), dated Sep. 15, 2014, corresponding to Chinese Patent Application No. 201080018022.0; 5 pages.
Chinese Office Action (with English translation) dated Mar. 3, 2015, corresponding to Chinese Patent Application No. 200680026156.0; 14 pages.
Chinese Office Action (with English translation), dated Sep. 1, 2014, corresponding to Chinese Patent Application No. 200680026156.0; 7 pages.
Chinese Office Action (with no English translation), corresponding to Chinese Patent Application No. 201080048091.6, dated Jul. 25, 2014; 6 pages.
Chinese Office Action (with No English translation), dated Feb. 12, 2015, corresponding to Chinese Application No. 201080048091.6; 7 pages.
Chodosh S., "Clinical Significance of the Infection-Free Interval in the Management of Acute Bacterial Exacerbations of Chronic Bronchitis," Chest, 127(6):2231-6, (Jun. 2005).
Choi et al., "Effect of moxifloxacin on production of proinflammatory cytokines from human peripheral blood mononuclear cells", Antimicrobial Agents and Chemotherapy (Dec. 2003) 47(12):3704-3707.
Christ-Crain, M. et al., "Biomarkers in Respiratory Tract Infections: Diagnostic Guides to Antibiotic Prescription, Prognostic Markers and Mediators", Eur Respir J., 30(3):556-73, (2007).
Chung, K. et al., "Multifaceted Mechanisms in COPD: Inflammation, Immunity, and Tissue Repair and Destruction", Eur Respir J., 31(6):1334-56, (2008).
Cigana, et al., "Azithromycin Selectively Reduces Tumor Necrosis Factor Alpha Levels in Cystic Fibrosis Airway Epithelial Cells," Antimicrobial Agents and Chemotherapy, vol. 51, No. 3, (Mar. 2007); pp. 975-981.
Clancy, et al., "Results of a phase IIa study of VX-809, an investigational CFTR corrector compound, in subjects with cystic fibrosis homozygous for the F508del-CFTR mutation," Thorax 2012, vol. 67; pp. 12-18.
ClinicalTrials.gov archive, Linking patients to medical research, A service of the U.S. National Institutes of Health, "Phase II, Multi-Center, Randomized, Double-Blind, Placebo-Controlled, Study to Evaluate the Safety, Tolerability and Efficacy of Three Dosage Regimens of MP-376 Solution for Inhalation Given for 28 Days to Stable CF Patients," (May 13, 2008); 7 pages.
Conrad, "Mpex 204 Phase 2," Stanford School of Medicine (retrieved online Dec. 11, 2009), Sep. 3, 2008, pp. 1-7 (PCT ISR/WO provided a partial reference, and the full reference is no longer available); 4 pages.
Conte et al., "Intrapulmonary pharmacodynamics of high-dose levofloxacin in subjects with chronic bronchitis or chronic obstructuctive pulmonary disease", International Journal of Antimicrobial Agents, Elsevier Science, Amsterdam, NL (2007) 30:422-427.
Cooney, et al., "Absolute Bioavailability and Absorption Characteristics of Aerosolized Tobramycin in Adults with Cystic Fibrosis", The Journal of Clinical Pharmacology, 34:255-9, (1994).
Crombleholme, MD, William R. "Preeclampsia-Eclampsia" Ch. 18 Obstetrics In: Current Medical Treatment and Diagnosis. 37th edited by Tierney, Jr. Lawrence M., McPhee, Stephen J., Papadakis, Maxine A.; Appleton and Lange, Stamford, CT 1998 pp. 731-734, (1998); (PDF is from 2004 43rd edition).
Dal Negro et al., "Tobramycin Nebulizer Solution in Severe COPD Patients Colonized with Pseudomonas Aeruginosa: Effects on Bronchial Inflammation" Advances in Therapeutics (2008) vol. 20 pp. 1019-1030.
Dalhoff et al., "Immunomodulatory effects of quinolones," The Lancet Infectious Diseases, vol. 3, (Jun. 2003); pp. 359-371.
Dalhoff, "Immunomodulatory activities of fluoroquinolones", Infection (2005) 33(Suppl 2):55-70.
Den Hollander, et al., "Synergism Between Tobramycin and Ceftazidime Against a Resistant Pseudomonas aeruginosa Strain, Tested in an In Vitro Pharmacokinetic Model," Antimicrobial Agents and Chemotherapy, vol. 41, No. 1, (Jan. 1997); pp. 95-100.
Derbacher, et al., "Physical Properties of Nebulized Solutions", Poster (1994) 381-382 (English Translation included).
DeRyke, et al., "Pharmacodynamic target attainment of six beta-lactams and two fluoroquinolones against Pseudomonas aeruginosa, Acinetobacter baumannii, *Escherichia coli*, and Klebsiella species collected from United States intensive care units in 2004," Pharmacotherapy (United States), vol. 27, No. 3, (Mar. 2007), pp. 333-342; Abstract Only.
Deterding, R. et al., "Phase 2 Randomized Safety and Efficacy Trial of Nebulized Denufosol Tetrasodiumin Cystic Fibrosis", Am J Respir Crit Care Med, 176(4):362-9.
Diakov, et al., "The Chemotherapeutic Efficacy of Ciprofloxacin and Lomefloxacin in the Inhalation Method of Infecting White Mice with Tularemia., Khimioterapevticheskaia Effektivnost' Tsiprofloksatsina i Lomefloksatsina Pri Ingaliatsionnom Sposobe Zarazheniia Tuliaremiei

(56) References Cited

OTHER PUBLICATIONS

Belykh Myshei", Antibiotiki i Khimioterapii a = Antibiotcs and Chemotherapy sic/ Ministerstvo Meditsinskoi i Mikrobiologicheskoi Promoyshlennosti SSSR (Russia), 45(6):17-20, (2000), (Abstract only).

Djurdjevic et al, "Study of Solution Equilibria Between Gadolinium (III) Ion and Moxifloxacin" Acta Chim. Slov. 2010, 57, pp. 386-397.

Djurdjevic, P. et al., "Study of solution equilibria between aluminum(III) ion and ofloxacin", Journal of Pharmaceutical and Biomedical Analysis, vol. 19(3-4):501-510, (Mar 1999).

Donnarumma, et al., "Anti-inflammatory Effects of Moxifloxacin and Human Beta-Defensin 2 Association in Human Lung Epithelial Cell Line (A549) Stimulated with Lipopolysaccharide", Peptides, 28:2286-92, (2007).

Doring et al., "Antibiotic therapy against Pseudomonas aeruginosa in cystic fibrosis: a European consensus" [comment in Eur Respir J. Oct. 2000; 16(4):585-7], Euro Respir J. Oct. 2000; 16(4):749-67. (Abstract Only).

Drevensek, et al., "X-Ray Crystallographic, NMR and Antimicrobial Activity Studies of Magnesium Complexes of Flouroquinolones—Racemic Ofloxacin and it's S-form, Levofloxacin", Journal of Inorganic Biochemistry, 100:1755-63, (2006).

Drevensek, et al., "Influence of Copper(II) and Magnesium(II) ions on the Ciprofloxacin Binding to DNA," Journal of Inorganic Biochemistry, vol. 96, (2003); pp. 407-415.

Drusano et al., "Pharmacodynamics of a Fluoroquinolone Antimicrobial Agent in a Neutropenic Rat Model of Pseudomonas Sepsis" Antimicrob. Agents & Chemother. (Mar. 1993) 37(3):483-490.

Dudley, M.N. et al. (Dec. 2008, e-published Nov. 25, 2008). "Aerosol antibiotics: considerations in pharmacological and clinical evaluation," Curr Opin Biotechnol 19(6):637-643.

Elizur, et al., "Airway Inflammation in Cystic Fibrosis", Chest, 133:489-95, (2008).

English language translation of WO 2006/100875 A1 obtained on Dec. 17, 2012.

English translation of Israeli First Examination Report, corresponding to Israeli Applicaiton No. 218458, dated Dec. 8, 2014; 3 pages.

English Translation summary of Japanese Office Action, corresponding to Japanese Application No. 2012-528109, dated Aug. 19, 2014; 3 pages.

EPO, Office Action dated Oct. 20, 2010 from European Patent Application 06 760 146.8—2123 filed May 18, 2008.

European Communication dated, Jun. 11, 2015, corresponding to European Patent Application No. 06760146.8; 5 pages.

European Communication/Examination Report, dated Jul. 7, 2015, corresponding to European Patent Application No. 10814595.4; 4 pages.

European Communication/Examination Report, dated Jul. 17, 2015, corresponding to European Patent Application No. 10767800.5; 5 pages.

European Office Action (Decision to Refuse a European Patent Application), dated Jul. 15, 2014, corresponding to European Application No. 09 793 326.1; 12 pages.

European Search Report dated Nov. 6, 2013 and European Communication dated Dec. 9, 2013, corresponding to European Application No. 12007354.9; 6 total pages.

European Search Report, dated Dec. 17, 2012, corresponding to European Application No. 10810290.6; 5 pages.

European Search Report, dated, Oct. 4, 2013, corresponding to European Application No. 10810291.4; 6 pages.

Extended European Search Report, dated Jan. 8, 2014, corresponding to European Patent Application No. 10 76 7800.5; 5 pages.

Extended Supplemental European Search Report, dated Apr. 17, 2013, corresponding to European Application No. 10814595.4; 9 pages.

File, Jr., "A New Dosing Paradigm: High-Dose, Short-Course Fluoroquinolone Therapy for Community-Acquired Pneumonia," Clinical Cornerstone—Supplemental 3, (2003); pp. S21-S28.

Flume et al., "Cystic Fibrosis Pulmonary Guidelines: Chronic Medications for Maintenance of Lung Health," Am J Respir Crit Care Med (2007) 176:957-969.

Fuchs et al., "Effect of Aerosolized Recombinant Human DNase on Exacerbations of Respiratory Symptoms and on Pulmonary Function in Patients with Cystic Fibrosis" the New England Journal of Medicine, Sep. 8, 1994, vol. 331, No. 10 pp. 637-642.

Garrity et al., "Bergey's Manual of Systematic Bacteriology," Editor-in-chief: Garrity, George M. Boone, David R.; Castenholz, Richard W. (Eds.) Originally published by Williams & Wilkins, 1984, 2nd ed. (2001).

Gavilanes, et al., "Azithromycin Fails to Reduce Increased Expression of Neutrophil-Related Cytokines in Primary-Cultured Epithelial Cells from Cystic Fibrosis Mice", J. Cystic Fibrosis, 10(1016):1-8, (2009).

Geddes, D. M., "5. Bronchiectasis and Cystic Fibrosis" Airways Obstruction (published 1981 by MTP Press Ltd) pp. 40-50.

Geller et al., "Levofloxacin Inhalation Solution (MP-376) in Patients with Cystic Fibrosis with Pseudomonas aeruginosa", Am J Respir Crit Care Med, (20110000), vol. 183, pp. 1510 - 1516, XP055403234 [X] 7, (8-10)/7 * ; abstract, p. 1511, col. 1, para 4, p. 1511, col. 2, para 6 * [Y] (8-10)/ (1-6), 59.

Geller, D.E. et al. (2008). "A Phase 1 Safety, Tolerability and Pharmacokinetic (PK) Study of MP-376 (Levofloxacin Solution for Inhalation) in Stable Cystic Fibrosis (CF) Patients," Pediatr Pulmonol Suppl 31, Abstract 321, 2 pages.

Geller, D.E. et al., "Pharmacokinetics and Safety of MP-376 (Levofloxacin Inhalation Solution) in Cystic Fibrosis Subjects", Antimicrobial agents and chemotherapy, vol. 55, No. 6, Jun. 1, 2011, pp. 2636-2640, XP55031818, ISSN: 0066-4804, DOI: 10.1128/AAC.01744-10.

Gennaro, "Remington: Practice of the Science and Pharmacy", 19.sup.th ed., Williams & Williams, (1995).

Gibaldi et al., "Pharmacokinetics", 2nd Edition, Marcel Dekker: New York (1982).

Goh, et al., "Current Status of Topical Nasal Antimicrobial Agents," The Laryngoscope, vol. 110 (Jun. 2000); pp. 875-880.

Griese, et al., "Amphotericin B and Pulmonary Surfactant," European Journal of Medical Research,vol. 3, No. 8, (Aug. 18, 1998); pp. 383-386--(Abstract Only).

Griffith et al., "Pharmacodynamics of Levofloxacin Against Pseudomonas Aeruginosa with Reduced Susceptibility Due to Different Efflux Pumps: Do Elevated MICs Always Predict Reduced in Vivo Efficacy?" Antimicrobial Agents and Chemotherapy, May 2006, vol. 50 No. 5 pp. 1628-1632.

Griffith, D. et al, "Pharmacokinetics and Safety of MP 376 (Levofloxacin solution for inhalation) in Normal Healthy Volunteers and Cystic fibrosis Patients", Pediatr. Pulmonol., (Aug. 29, 2007), vol. 42, No. S30, p. 303, XP002560243.

Griffith, et al., "Efficacy of Fluoroquinolones Against Leptospira Interrogans in a Hamster Model", Antimicrobial Agents and Chemotherapy (United States), 51(7):2615-2617, (2007), (Abstract only).

Griffith, et al., (C1-1954) "In vitro Activity of Levofloxacin (LVX) and Other Antibiotics Administered by the Aerosol Route in Cystic Fibrosis (CF) Against Pseudomonas aeruginosa (Pa) Under Anaerobic Conditions," IDSA, Oct. 27, 2008; Abstract Only.

Griffith, et. al., "Single-Dose Pharmacokenetics of Aerosol MP-376 (Levofloxacin Solution for Inhalation) in Cystic Fibrosis Patients: PK-PD implacations", Journal of Cystic Fibrosis, (Jun. 2008), abstract 104(7):526, (abstract).

Guina, et al., "Quantitative Proteomic Analysis Indicates Increased Synthesis of a Quinolone by Pseudomonas Aeruginosa Isolates from Cystic Fibrosis Airways", PNAS, 100(5):2771-6, (Mar. 4, 2003).

Handbook of Pharmaceutical Excipients, published jointly by the American Pharmaceutical Association and the Pharmaceutical Society of Great Britain (The Pharmaceutical Press, 1986).

Hart et al., "Cross-over assessment of serum bactericidal activity of moxifloxacin and levofloxacin versus penicillin-susceptible and penicillin-resistant *Streptococcus pneumoniae* in healthy volunteers", Diagnostic Microbiology and Infectious Disease (United States) (Jul. 2007) 58(3):375-8. (Abstract Only).

(56) References Cited

OTHER PUBLICATIONS

Harutyunyan, "Mpex Pharmaceuticals Presents Data on MP-376 in Cystic Fibrosis" EmaxHealth Oct. 24, 2008 (http://www.emaxhealth.com/2/95/25752/mpex-pharmaceuticals-presents-data--mp-376-cystic-fibrosis.html).
Hashimoto, et al., "Grepafloxacin Inhibits Tumor Necrosis Factor-alpha-induced Interleukin-8 Expression in Human Airway Epithelial Cells," Life Sciences, vol. 66, No. 5, (2000); pp. 77-82—(Abstract Only).
Hecht, et al., "In Vitro Activities of 15 Antimicrobial Agents Against 110 Toxigenic Clostridium difficile Clinical Isolates Collected from 1983 to 2004," Antimicrobial Agents and Chemotherapy, vol. 51, No. 8, (Aug. 2007); pp. 2716-2719.
Heine, et al., Major Article, "Comparison of 2 Antibiotics That Inhibit Protein Synthesis for the Treatment of Infection with Yersinia pestis Delivered by Aerosol in a Mouse Model of Pneumonic Plague," Journal of Infectious Diseases, vol. 196, No. 5, (2007); pp. 782-787.
Hodson, "Antibiotic Treatment: Aerosol Therapy," Chest, vol. 94, (1988); pp. 156S-160S.
Hoffmann, et al., "Novel Mouse Model of Chronic Pseudomonas Aeruginosa Lung Infection Mimicking Cystic Fibrosis", Infect. Immun., 73(4):2504-14, (2005).
Honeybourne, "Antibiotic Penetration in the Respiratory Tract and Implications for the selection of Antimicrobial Therapy", Current Opinion of Pulmonary Medicine, 3(2):170-4, (1997), (Abstract only).
Hoogkamp-Korstanje, "In-Vitro Activities of Ciprofloxacin, Levofloxacin, lomefloxacin, Ofloxacin, Pefloxacin, Sparfloxacin and Travofloxacin Against Gram-Positive and Gram-Negative Pathogens from Respiratory Tract Infections", Journal of Antimicrobial Chemotherapy, 40:427-31, (1997).
Horiguchi, et al., "Usefulness of sparfloxacin against Chlamydia pneumoniae infection in patients with bronchial asthma," Journal of International Medical Research (England), vol. 33, No. 6, (Nov.-Dec. 2005); pp. 668-676, (Abstract Only).
Hrkach, et al., "Synthesis of poly(L-lactic acid-co-L-lysine) Graft Copolymers," Macromolecules, vol. 28, No. 13, (1995); pp. 4736-4739—(Abstract Only).
Huang et al., "Oxidation of fluoroquinolone antibacterials and structurally related amines with manganese oxide" National Meeting—American Chemical Society Division of Environmental Chemistry (2003) 43(2)(5):1257-1260.
Huang, H. et al., "Comparing the Protective Effects of Ciprofloxacin, Moxifloxacin and Levofloxacin in Mice with Lipopolysaccharide-Induced Acute Lung Injuries", Respirology, 13(6):47-52, (Jan. 2008).
Hung, et al., "Evaluation of Two Commercial Jet Nebulisers and Three Compressors for the Nebulisation of Antibiotics," Archives of Diesase in Childhood, 71(4):335-8, (Oct. 1994).
Hutschala, et al., "In Vivo Measurement of Levofloxacin Penetration into Lung Tissue: CPB versus OPCAB", European Journal of Anaesthesiology, 49(12):5107-11, (2005).
Indian First Examination Report (English translation only), dated Oct. 15, 2013, corresponding to Indian Patent Application No. 9505/DELNP/2007; 3 pages.
International Application No. PCT/US2016/044607; International Preliminary Report on Patentability dated Jan. 30, 2018; 9 pages.
International Application No. PCT/US2016/044607; International Search Report and Written Opinion of the International Search Authority, dated Dec. 12, 2016; 14 pages.
International Application No. PCT/US2017/016161; International Preliminary Report on Patentability (Ch I), dated Aug. 7, 2018; 9 pages.
International Application No. PCT/US2017/016161; International Search Report and Written Opinion of the International Search Authority, dated Jun. 9, 2017; 12 pages.
International Patent Application No. PCT/US2010/032128; International Preliminary Report on Patentability, dated Oct. 25, 2011; 8 pages.

International Patent Application No. PCT/US2010/032128; International Search Report and Written Opinion of the International Search Authority, dated Jul. 30, 2010; 11 pages.
International Preliminary Report on Patentability, dated Apr. 12, 2011 and Written Opinion of the International Searching Authority and International Search Report, dated Dec. 17, 2009, corresponding to International Patent Application No. PCT/US2009/059744; 15 total pages.
International Preliminary Report on Patentability, dated Aug. 19, 2008 and Written Opinion of the International Searching Authority and International Search Report, dated Oct. 25, 2007, corresponding to International Patent Application No. PCT/US2007/003649; 21 total pages.
International Preliminary Report on Patentability, dated Aug. 31, 2010 and Written Opinion of the International Searching Authority and International Search Report, dated Jan. 21, 2010, corresponding to International Patent Application No. PCT/US2009/059740; 18 total pages.
International Preliminary Report on Patentability, dated Feb. 21, 2012 and Written Opinion of the International Searching Authority and International Search Report, dated Oct. 20, 2010, corresponding to International Patent Application No. PCT/US2010/002307; 17 total pages.
International Preliminary Report on Patentability, dated Mar. 6, 2012 and Written Opinion of the International Searching Authority and International Search Report, dated Dec. 7, 2010, corresponding to International Patent Application No. PCT/US2010/047903; 23 total pages.
International Preliminary Report on Patentability, dated Nov. 20, 2007 and Written Opinion of the International Searching Authority and International Search Report, dated Oct. 20, 2006, corresponding to International Patent Application No. PCT/US2006/019351; 15 total pages.
International Search Report and Written Opinion corresponding to International Application No. PCT/US2010/002306, dated Nov. 8, 2010 by the Astralian Patent Office in its capacity as International Searching Authority; 10 total pages.
IPOS Search Report, Written Opinion and Invitation to Response to Written Opinion, dated Aug. 12, 2010 for Singapore Patent Application No. 200717702-5.
Israel Official Action (No English Translation), dated Dec. 8, 2013, corresponding to Israeli Patent Application No. 212190; 4 pages.
Israeli Examination Report (English translation only), dated Sep. 11, 2014, corresponding to Israeli Patent Application No. 215777; 2 pages.
Israeli Office Action (with No English tranlsation), dated Jan. 5, 2015, corresponding to Israeli Patent Application No. 212190; 3 pages.
Jacquot et al., "Airway epithelial cell inflammatory signalling in cystic fibrosis," The International Journal of Biochemistry & Cell Biology (2008) 40:1703-15.
Japanese Decision of Rejection (English translation only), dated Jun. 5, 2014, corresponding to Japanese Application No. 2011-531125; 3 pages.
Japanese Decision of Rejection (with English Translation), dated Apr. 15, 2015, corresponding to Japanese Patent No. 2012-528109; 5 pages.
Japanese Decision of Rejection (with English translation), dated Nov. 6, 2014, corresponding to Japanese Patent Application No. 2011-531126; 5 total pages.
Japanese Decision of Rejection with English translation, dated Jun. 1, 2015, corresponding to Japanese Patent Application No. 2012-507400; 4 total pages.
Japanese Notice of Reasons for Rejection (English Translation only), dated Dec. 24, 2013, corresponding to Japanese Patent Application No. 2011-531126; 6 pages.
Japanese Notice of Reasons for Rejection (with English translation), dated Apr. 27, 2015, corresponding to Japanese Patent Application No. 2014-095077; 10 total pages.
Japanese Office Action (with English translation), dated Jun. 10, 2014, corresponding to Japanese Patent Application No. 2012-507400; 5 pages.

(56) References Cited

OTHER PUBLICATIONS

Japanese Office Action dated Mar. 11, 2014 (with English translation), corresponding to Japanese Application No. 2013-002399; 7 total pages.
Japanese Office Action dated Oct. 20, 2014 (with English translation), corresponding to Japanese Application No. 2013-002399; 6 pages.
Jarraud, et al., "Legionnaires Disease (Legionellose)", Presse Medicale (Paris, France—1983) (France), 36(2 parts):279-87, (2007), (Abstract only).
Jensen, et al., "The efficacy and safety of ciprofloxacin and ofloxacin in chronic Pseudomonas aeruginosa infection in cystic fibrosis," Journal of Antimicrobial Chemotherapy, vol. 20, No. 4, (1987); pp. 585-594.
Jones and Helm, "Emerging Treatments in Cystic Fibrosis," Drugs 2009, vol. 69, No. 14; pp. 1903-1910.
Jones et al., "Quantifying of severity of exacerbations in chronic obstructive pulmonary disease: adaptations to the definition to allow quantification", Proc Am Thorac Soc. (2007) 4(8):597-601.
Jones, et al., "St. George's Respiratory Questionnaire Manual", St. George's University of London, (Jun. 2009), 17 pages.
Jumbe et al., "Application of a Mathematical Model to Prevent In Vivo Amplification of Antibiotic-Resistant Bacterial Populations During Therapy" The Journal of Clinical Investigation, Jul. 2003, vol. 112, No. 2, pp. 275-285.
Kays, et al., "Levofloxacin treatment failure in a patient with fluoroquinolone-resistant Streptococcus pneumoniae pneumonia", Pharmacotherapy, Mar. 2002, vol. 22, No. 3, pp. 395-399.
Kearns, et al., "Poster No. 88: Levofloxacin Pharmacokinetics (PK) after Administration of MP-376 (Levofloxacin Inhalation Solution; Aeroquin.RTM.) in Children with Cystic Fibrosis (CF)" 34th European Cystic Fibrosis Conference Jun. 8-11, 2011.
Khan, et al., "Effect of Travofloxacin on Production of Cytokines by Human Monocytes", Antimicrobial Agents and Chemotherapy, 42(7):1713-7, (1998).
Khan, et al., "Protection Against Lipopolysaccharide-Induced Death by Fluoroquinolones", Antimicrobial Agents and Chemotherapy, 44(11):3169-73, (2000).
King et al, "In Vitro Pharmacodynamics of Levofloxacin and Other Aerosolized Antibiotics under Multiple Conditions Relevant to Chronic Pulmonary Infection in Cystic Fibrosis" Antimicrobial Agents and Chemotherapy, Jan. 2010, vol. 54, No. 1, pp. 143-148.
King et al., "Effect of oxygen limitation on the in vitro activity of levofloxacin and other antibiotics administered by the aerosol route against Pseudomonas aeruginosa from cystic fibrosis patients", Diagn Microbiol Infect Dis. Feb. 2010;66(2)181-6. Epub Oct. 13, 2009.
Kitazawa, et al., "Biophasic Regulation of Levofloxacin on Lipopolysaccharide-Induced IL-1B Production", Life Sciences, 80:1572-7, (2007).
Kobayashi, et al., "Antibacterial Activity of Tosufloxacin Against Major Organisms Detected by Patients with Respiratory Infections", Japanese Journal of Antibiotics (Japan), 60(2):98-106, (2007), (Abstract only).
Kohyama et al., "Fourteen-member macrolides inhibit interleukin-8 release by human eosinophils from atopic donors," Antimicrobial Agents and Chemotherapy, vol. 43, No. 4, (Apr. 1999); pp. 907-911.
Korean Office Action (English translation only), dated Aug. 27, 2014, corresponding to Korean Patent Application No. 10-2007-7029629; 1 page.
Korean Office Action (with English translation) dated Aug. 29, 2014, corresponding to Korean Patent Application No. 10-2007-7016750; 7 pages.
Korean Office Action (with English translation) dated Mar. 28, 2014, corresponding to Korean Application No. 10-2007-7029629; 8 pages.
Korean Office Action, (No English translation), dated Oct. 31, 2014, corresponding to Korean Patent Applcation No. 10-2014-7002452; 3 pages.
Kraynack, et al., "Improving Care at Cystic Fibrosis Centers Through Quality Improvement", Seminars in Respiratory and Critical Care Medicine, 30(5):547-58, (2009).
Kuhn, "Formulation of aerosolized therapeutics", Chest, The Cardiopulmonary and Critical Care Journal (2001) 120(3):945-985. (Abstract Only).
Kurosaka et al., "DX-619, a novel Des-F(6)-quinolone: Pharmacodynamics (PD) Activity and Thereapeutic Efficacy in Animal Infection Models", 43rd Interscience Conference on Antimicrobial Agents and Chemotherapy (p. 241 43rd ICAAC Abstracts) ( Sep. 14-17, 2003) Chicago, Illinois.
Lacy et al, Drug Information Handbook American Pharmaceutical Association—1999-2000, Lexi-Comp Inc.: Hudson, Ohio pp. 589-590 and 749-750.
Lammerts Van Bueren et al.: "Structural and Thermodynamic Analyses of alpha-L-Fucosidase Inhibitors", Chembiochem, vol. 11, No. 14, Sep. 24, 2010 (Sep. 24, 2010), pp. 1971-1974, XP009168983, ISSN: 1439-4227 [retrieved on Jul. 27, 2010].
LaPlante, et al., "Fluoroquinolone resistance in Streptococcus pneumoniae: area under the concentration-time curve/MIC ratio and resistance development with gatifloxacin, gemifloxacin, levofloxacin, and moxifloxacin" Antimicrobial Agents and Chemotherapy (United States) (Apr. 2007), vol. 51, No. 4: pp. 1315-1320. (Abstract Only).
Le Conte, et al., "Lung Distribution and Pharmacokinetics of Aerosolized Tobramycin", American Review of Respiratory Disease, (1993) vol. 147, pp. 1279-1282.
Lee, et al., "Levofloxacin Pharmacokinetics in Adult Cystic Fibrosis", Chest, vol. 131, No. 3, (2007); pp. 796-802.
Legssyer, et al., "Azithromycin reduces spontaneous and induced inflammation in F508 cystic fibrosis mice," Respiratory Research, vol. 7, No. 134, (2006); pp. 1-13.
Leiva, et al., "Effects of Telithromycin in In Vitro and In Vivo Models of Lipopolysaccharide-Induced Airway Inflammation," Chest, vol. 134, No. 1, (Jul. 2008); pp. 20-29.
Leonard et al., "Topical Antibiotic Therapy for Recalcitrant Sinusitis," The Laryngoscope, vol. 109, No. 4, (Apr. 1999); pp. 668-670.
Lode, N. et al., "Levofloxacin Versus Clarithromycin in COPD Exacerbation: Focus on Exacerbation-Free Interval", European Respiratory Journal, 24(6):947-53, (2004).
Louie, et al., "Impact of Resistance Selection and Mutant Growth Fitness on the Relative Efficacies of the Streptomycin and Levofloxacin for Plague Therapy", Antimicrobial Agents and Chemotherapy, 51(8), (Aug. 2007), (Abstract only).
MacMillan Encyclopedia of Physics, vol. 4, Simon & Schuster: London, 1996, pp. 1677.
Mandell, et al., "Safety of fluoroquinolones: An update," The Canadian Journal of Infectious Diseases, vol. 13, No. 1, Jan.-Feb. 2002; pp. 54-61.
Martin, Physical Pharmacy (4th Edition), Physical Chemical Principles in the Pharmaceutical Sciences, Chapter II, Complexation and Protein Binding, pp. 261-263, and p. 265; Published by Lippincott Williams & Wilkins, Philadelphia, PA, 1993; 6 total pages.
Martinez et al, "Appropriate outpatient treatment of acute bacterial exacerbations of chronic bronchitis", American Journal of Medicine (Jul. 1, 2005), vol. 118, No. 7, ISSN 0002-9343, pp. 39-44, XP005148473.
Matthys, "Inhalation Delivery of Asthma Drugs", Lung., 168:645-52, (1990), (Abstract only).
Mazurek, H. et al, "Cystic Fibrosis lung disease: infection, inflammation, or both? Helicobacter pylori seroprevalence in patients with cystic fibrosis", European Respiratory Annual Congress 2006 as accessed Jan. 24, 2014 from http://www.ers-education.org/home/browse-all-content.aspx?idPar-ent=7958.
McCoy, et al., "Inhaled Aztreonam Lysine for Chronic Airway Pseudomonas Aeruginosa in Cystic Fibrosis", American Journal of Respiratory and Critical Care Medicine, 178:921-8, (2008).
McGraw-Hill Encyclopedia of Science & Technology, 9th edition, McGraw-Hill: New York, 2002, pp. 303.
MedlinePlus Medical Encyclopedia, "Cystic Fibrosis," at p. 1 accessed on Jul. 11, 2008 at www.nlm.nih.gov/medlineplus/ency/article/000107.htm.

(56) References Cited

OTHER PUBLICATIONS

Meguro, et al., "Development and Validation of an Improved, COPD-Specific Version of the St. George Respiratory Questionnaire," Chest, vol. 132, No. 2, (Aug. 2007); pp. 456-463.
Mexican Office Action (with English translation), dated Jan. 14, 2015, corresponding to Mexican Patent Application No. MX/a/2011/011190; 8 total pages.
Mexican Office Action (with No English tranlsation), corresponding to Mexican Patent Application No. MX/a/2011/003745, dated Dec. 1, 2014; 4 pages.
Mexican Office Action, dated Aug. 12, 2014 (no English translation), corresponding to Mexican Application No. MX/a/2011/007566; 2 pages.
Mexican Office Action, dated Jun. 11, 2014 (no English translation), corresponding to Mexican Application No. MX/a/2011/007566; 2 pages.
Mexican Official Action (no English Translation) dated May 27, 2014, corresponding to Mexican Patent Application No. Mx/a/2011/003745; 2 pages.
Miller, et al., "Standardisation of spirometry," American Thoracic Society/European Respiratory Society (ATS/ERS) Spirometry Standards, Eur Respir J 2005, vol. 26 No. 2; pp. 319-338.
Mohammed, et al., "Intravenous and Nebulised Magnesium Sulphate for Acute Asthma: Systematic Review and Meta-Analysis", Emergency Medicine Journal, 24:823-30, (2007).
Mori, et al., "Influence of Prescription days by Simultaneous Combined Use of New Quinolone and Drugs Containing Metal Cation", Japanese Society of Hospital Pharmacists Journal, 35(4):469-72, (1999).
Moss, "Administration of Aerosolized Antibiotics in Cystic Fibrosis Patients", Chest, 120(3):107S-13S, (2001), (Abstract only).
Movassaghi, M. et al. Total Synthesis and Absolute Stereochemical Assignment of (+)- and (-)-Galbulimima Alkaloid 13- Supplementary Information. JACS Communications. 2006, vol. 128, p. S54.
Movassaghi, M. et al. Total Synthesis and Absolute Stereochemical Assignment of (+)- and (-)-Galbulimima Alkaloid 13. JACS Communications. 2006, vol. 128, p. 8126.
Mpex Pharmaceuticals Presents New Data on MP-376 in Cystic Fibrosis, (http://www2.prnewswire.com/cgi-bin/stories.pl?ACCT=104&STORY=/www/story/-10-23 2008/0004910076&EDate=); Oct. 23, 2008; 4 pages.
Murphy, et al., "Pseudomonas Aeruginosa in Chronic Obstructive Pulmonary Disease", American Journal of Respiratory and Clinical Care Medicine, (177):853-60, (2008).
Murray, "Lung Inflammation Treatment," by eHow Health. [retrieved on Mar. 7, 2013]. Retrieved from the Internet at http://www.ehow.com/about.sub.--5417681.sub.--lung-inflammation-treatment-.html; 4 pages.
Nakanishi, et al., "A case of cystic fibrosis in a Japanese student", Nihon Kyobu Shikkan Gakkai Zasshi (Japan), vol. 33, No. 7, (1995); pp. 771-774--(Abstract Only).
Navarro, et al., "Oral Absorption of Ofloxacin Administered Together with Aluminum", Antimicrobial Agents and Chemotherapy, 1994, vol. 38, No. 10, p. 2510-2512.
NCBI Bookshelf Glossary, Appendix D, definition of "Microbe," accessed at http://www.ncbi.nlm.nih.gov/books/NBK54258/; 1 page, 2010.
Neu, "The Effects of Cations Upon the Activity of Quinolone Agents", Quinolones Bulletin, Reports on Gyrase Inhibitors (1985).
Neu, et al., "In Vitro Activity of S-Ofloxacin," Antimicrobial Agents and Chemotherapy, American Society for Microbiology, vol. 33, No. 7, (1989); pp. 1105-1107.
New Zealand First Examination Report, dated Sep. 30, 2014, corresponding to New Zealand Patent Application No. 631469; 2 pages.
New Zealand First Examination, dated Oct. 14, 2013, corresponding to New Zealand Patent Application No. 616438; 2 pages.
New Zealand First Examintion Report, dated Feb. 25, 2013, corresponding to New Zealand Patent Application No. 607408; 3 pages.
New Zealand Further Examination Report dated Dec. 10, 2014, corresponding to New Zealand Patent Application No. 616438, 2 pages.
New Zealand Further Examination Report, dated Sep. 5, 2014, corresponding to New Zealand Patent Application No. 607408; 3 pages.
Newman, "Aerosols and the Lung:Clinical and Experimental Aspects," Butterworth & Co. Ltd., London, England (1984); pp. 197-224.
Noel GJ, et al, Coparative Safety Profile of Levofloxacin in 2523 Children with a Focus on Four Specific Musculoskeletal Disorders. Pediatr. Infect Dis J. Oct. 2007; 26(10):879-91—Abstract only-found in the Internet Oct. 9, 2014—http://www.ncbi.nlm.nih.gov/pubmed/17901792.
Nouira Semir et al, "Once daily oral ofloxacin in chronic obstructive pulmonary disease exacerbation requiring mechanical ventilation: A randomised placebo-controlled trial", Lancet (North American Edition), (Dec. 15, 2001), vol. 358, No. 9298, ISSN 0099-5355, pp. 2020-2025, XP004805687.
O-Lee et al, "Fluoroquinolone-induced arthralgia and myalgia in the treatment of sinusitis", Am. J. Rhino!. (2005) 19(4):395-399.
Office Action dated Apr. 27, 2010 from Russian Patent Application No. 2007146972 filed on May 18, 2006.
Ono et al., "Effect of grepafloxacin on cytokine production in vitro", Journal of Antimicrobial Chemotherapy, (2000) 46:91-94.
Ortho-Mcneil Pharmaceutical, Inc., OMP Division, Text of Proposed Labeling for Levaquin.RTM. (2004) 1-52.
Ortho-McNeil Pharmaceutical, Inc., Package Insert for Levaquin. RTM., (2006) 15 pages.
Palmer, K. et al., "Membrane-Bound Nitrate Reductase is Required for Anaerobic Growth in Cystic Fibrosis Sputum", J Bacteriol., 189(12):4449-55, (2007).
Pavlinova et al., "Estimation of the Modern Mucolytic Therapy Efficacy in Children Suffering From Mucoviscidosis (two-year experience of dornase alfe application)," Voprosy Sovremennoi Pediatrii, vol. 2007, No. 2, (2007), pp. 102-106—(with English translation of relevant parts).
Pellegrino, et al., "Interpretative strategies for lung function tests," European Respiratory Journal, vol. 26, No. 5, (2005); pp. 948-968.
Perez, et al., "CFTR Inhibition Mimics the Cystic Fibrosis Inflammatory Profile", Am. J. Physiol. Lung Cell Mol Physiol, 292(2):383-95, (2007), (Abstract only).
Polenakovik, et al., "The use of ivacaftor in an adult with severe lung disease due to cystic fibrosis," Journal of Cystic Fibrosis, Elsevier, (2013); pp. 1 and 2.
Preston et al., "Pharmacodynamics of levofloxacin: a new paradigm for early clinical trials," Jama. (1998) 279(2):125-129.
Pringle, C., "Influenza," Merck Manual Home Edition article, accessed at http://www.merckmanuals.com/home/infections/viral-infections/influenza-flu; 8 pages.
Quan, et al., "A Two-Year Randomized, Placebo-Controlled Trial of Dornase Alfa in Young Patients with Cystic Fibrosis with Mild Lung Function Abnormalities", the Journal of Pediatrics, 139(6):813-20; (Dec. 2001).
Querol-Ribelles, et al., "Discrepancy Between Antibiotics Administered in Acute Exacerbations of Chronic Bronchitis and Susceptibility of Isolated Pathogens in Respiratory Samples: Multicentre Study in Primary Care Setting", International Journal of Antimicrobial Agents, 28(5):472-6, (Nov. 2006), (Abstract only).
Rapp, "Fluoroquinolone Positioning in Hospital Antimicrobial Stewardship Programs," U.S. Pharmacist, vol. 32, No. 12, (2007); pp. HS-10 to HS-17 (6 pages).
Ratcliffe et al., "Effects of Magnesium on the Activity of 4-Quinolone Antibacterial Agents", Journal of Pharmacy and Pharmacology, 1983, p. 61, vol. 35, Supplement Dec. 1983, The Pharmaceutical Society of Great Britain.
Reato, et al., "Immunomodulating effect on antimicrobial agents on cytokine production by human polymorphonuclear neutrophils," International Journal of Antimicrobial Agents, vol. 23, No. 2, (Feb. 2004); pp. 150-154—(Abstract Only).
Rennard, Stephen I. "COPD: Overview of Definitions, Epidemiology, and Factors Influencing Its Development" Chest / 113 / 4/ Apr. 1998 p. 235S-241S.

(56) References Cited

OTHER PUBLICATIONS

Romano et al., "[the use of ofloxacin in cystic fibrosis patients.] Uso dell'ofloxacin nei pazienti con fibrosi cistica", Minerva Pediatr. (Mar. 1992) 44(3):79-86. (Abstract Only).
Rosell, A. et al., "Microbiologic determinants of exacerbation in chronic obstructive pulmonary disease" Arch Intern Med 165: 2005, p. 891-897 (printed from http://archinte.jamanetwork.com/article.aspx?articleid=486514).
Rosenfeld et al, "Defining a Pulmonary Exacerbation in Cystic Fibrosis" The Journal of Pediatrics, Sep. 2001, vol. 139(3), pp. 359-365 (from http://ovidsp.tx.ovid.com/sp-3.7.1b/ovidweb.cgi).
Ross, et al., "Physicochemical properties of the fluoroquinolone antimicrobials V. effect of fluoroquinolone structure and pH on the complexation of various fluoroquinolones with magnesium and calcium ions," International Journal of Pharmaceutics, XP25565729 (1993) vol. 93; pp. 121-129.
Russian Office Action (with English translation), corresponding to Russian Patent Application No. 2012111458/15, dated Jan. 26, 2015; 9 pages.
Russian Office Action (with English translation), corresponding to Russian Patent Application No. 2012111458/15, dated Sep. 12, 2014; 16 total pages.
Russian Office Action (with English Translation), dated Apr. 23, 2015, corresponding to Russian Patent Application No. 2011118619/15; 8 total pages.
Sabet et al., "Efficacy of Aerosol MP-378, a levofloxacin inhalation solution, in models of mouse lung infection due to Pseudomonas aeruginosa, Antimicrobial Agents and Chemotherapy", (2009) 53(9):3923-3928.
Sabet et al., "In-Vivo Antibacterial Activity of Aerosol MP-376 in Mouse Models of Pulmonary Infection", #288 The 21st Annual North American Cystic Fibrosis Conference (2007) p. 304.
Sagel et al., "Sputum biomarkers of inflammation in cystic fibrosis lung disease", Proc. Am. Thorac. Soc. (2007) 4:406-417.
Saito, et al., "New drugs used for Infection Disease Synthetic Antibacterials Levofloxacin", Clinical and Drug Therapy, 13(2):187-92, (1994).
Sakai, et al., "Comparison of the complexation of fluoroquinolone antimicrobials with metal ions by nuclear magnetic resonance spectroscopy," Journal of Pharmaceutical and Biomedical Analysis, 18 (Elsevier) (1999); pp. 1057-1067.
Salvatore, D. et al. (Jul. 2002). "Effects of salmeterol on arterial oxyhemoglobin saturations in patients with cystic fibrosis," Pediatr Pulmonol 34(1):11-15.
Sandor, P.S., et al., "Prophylactic Treatment of Migraine With b-Blockers and Riboflavin: Differential Effects on the Intensity Dependence of Auditory Evoked Cortical Potentials" Headache 40(1), Jan. 2000, pp. 30-35.
Sato et al, "Antimicrobial Activity of DU-6859, a New Potent Fluoroquinolone, Against Clinical Isolates" Antimicrobial Agents and Chemotherapy, vol. 36, No. 7, Jul. 1992, p. 1491-1498.
Scheinberg, et al., "Nebulized Antibiotics for the Treatment of Acute Exacerbations of Chronic Rhinosinusitis," ENT--Ear, Nose & Throat Journal, vol. 81, No. 9, (Sep. 2002), pp. 648-652.
Schoenen, et al., "Effectiveness of high-dose riboflavin in migraine prophylaxis—A randomized controlled trial," American Accademy of Neurology, vol. 50, No. 2, (Feb. 1998); pp. 466-470.
Seddon, "Pseudopolymorph: a polemic", Crystal Growth & Design (2004) 4(6):1087, web release date Oct. 19, 2004.
Seeimungal, et al., "Long-term erythromycin therapy is associated with decreased chronic obstructive pulmonary disease exacerbations," American Journal of Respiratory and Critical Care Medicine, vol. 178, (2008), pp. 1139-1147.
Sethi, et al. "Poster No. 27964: A Phase 2 Study to Evaluate the Safety, Tolerability, and Efficacy of Levofloxacin Inhalation Solution (MP-376) Administered for 5 Days Every 28 Days to Prevent Acute Exacerbations in High Risk COPD Patients" American Thoracic Society 2012 International Conference, May 18-23, 2012; 1 page.
Sethi, et al., "New Strains of Bacteria and Exacerbations of Chronic Obstructive Pulmonary Disease," The New England Journal of Medicine, vol. 347, No. 7, (Aug. 15, 2002); pp. 465-471.
Shalit, et al., "Anti-Inflammatory Effects of Moxifloxacin on IL-8, IL-1B and TNF-a Secretion and NFκB and MAP-kinase Activation in Human Monocytes Stimulated with Aspergillus Fumigatus", Journal of Antibacterial Chemotherapy, 57:230-5, (2006).
Shalit, et al., "Immunomodulatory and protective effects of moxifloxacin against candida albicans-induced bronchopneumonia in mice injected with cyclophosphamide," Antimicrobial Agents and Chemotherapy, vol. 46, No. 8, (2002); pp. 2442-2449.
Shinkai et al., "Clarithromycin has an immunomodulatory effect on ERK-mediated inflammation induced by Pseudomonas aeruginosa flagellin", Journal of Antimicrobial Chemotherapy (2007) 59:1096-1101.
Shinkai, et al "Macrolide antibiotics as immunomodulatory medications: Proposed mechanisms of action," Pharmacology & Therapeutics, vol. 117, (2008); pp. 393-405.
Singapore Written Opinion and Search Report, dated Jun. 2, 2015, issued by the Intellectual Property Office of Singapore (IPOS), corresponding to Singapore Patent Application No. 201202482-4; 11 total pages.
Skauge et al., "Interaction Between Ciprofloxacin and DNA Mediated by Mg2+—ions", Inorganica Chimica Acta (2002) 339: 239-247.
Smith et al., "Chemistry and Mechanisms of Action of the Quinolone Antibacterials", Chapter 2 of "The Quinolones" Academic Press Limited, Harcourt Brace Janovich, Publishers (1988) pp. 23-82.
Smith, "Interactions Between 4-Quinolone Antibacterials and Multivalent Metal Ions," Microbiology Section, Department of Pharmaceutics, The School of Pharmacy, University of London, Brunswick Square, London, England. Journal of Chemotherapy (Florence, Italy) 1989, 1(4 Suppl): pp. 134-135.
Soler, N. et al, "Airway Inflammation and Bronchial Microbial Patterns in Patients with Stable Chronic Obstructive Pulmonary Diseae" European Respiratory Journal 14 (1999) p. 1015-1022.
Stephenson, "Applications of X-Ray Powder Diffraction in the Pharmaceutical Industry," The Rigaku Journal, vol. 22, No. 1, (2005); pp. 2-15.
Stockley, et al., "Relationship of Sputum Color to Nature and Outpatient Management of Acute Exacerbations of COPD", Chest 117(6):1638-45, (Jun. 2000).
Strieter, "Interleukin-8: A Very Important Chemokine of the Human Airway Epithelium", Journal of Physiology—Lung Cell Molecular Physiology, 283:L688-9, (2002).
Suman, et al., "Comparison of Nasal Deposition and Clearance of Aerosol Generated by a Nebulizer and an Aqueous Spray Pump", Pharmaceutical Research, 16(10):1648-52, (1999).
Suman, et al., "Validity of In Vitro Tests on Aqueous Spray Pumps as Surrogates for Nasal Deposition," Pharmaceutical Research, vol. 19, No. 1, (Jan. 2002); pp. 1-6—(Abstract Only).
Suri, R. et al. (Feb. 2007, e-published Jun. 27, 2006). "Assessing the usefulness of outcomes measured in a cystic fibrosis treatment trial," Respir Med 101(2):254-260.
Suzuki, et al., "Histopathological Study of the Effects of a Single Intratracheal Instillation of Surface Active Agents on Lung in Rats," The Journal of Toxicological Sciences, vol. 25, No. 1, (2000); pp. 49-55—(Abstract Only).
Tabaru, et al., P4677—"Various Aspects of Respiratory Epidemiology: Helicobacter pylori infection in COPD," accessed at http://lrp.ersnet.org/abstract.sub.--print.sub.--10/files/407.pdf; p. 858s, 2010.
Takeyama, et al., "The 6-Fluoro-8-Methoxy Quinolone Gatifloxacin Down-Regulates Interleukin-8 Production in Prostate Cell Line PC-3," Antimicrobial Agents and Chemotherapy, vol. 51, No. 1, (Jan. 2007); pp. 162-168.
Takizawa, et al., "Erthromycin Modulates IL-8 Expression in Normal and Inflamed Human Bronchial Epithelial Cells", American Journal of Respiratory and Clinical Care Medicine, (156):266-71, (1997).
Tanaka et al., "Antimicrobial Activity of DV-7751a, a New Fluoroquinolone" Antimicrobial Agents and Chemotherapy, Oct. 1993, vol. 37, No. 10, p. 2112-2118.

(56) References Cited

OTHER PUBLICATIONS

The Engineering ToolBox, "Dynamic, Absolute, Kinematic Viscosity" accessed online at http://www.engineeringtoolbox.com/dynamic-absolute-kinematic-vi-scosity-d.sub.--412.html (6 pages).

The Engineering Toolbox, "Surface Tension,"—accessed at http://www.engineeringtoolbox.com/surface-tension-d.sub.--962.html (3 pages), 2015.

Tirouvanziam, et al, Rapid Communication—"Inflammation and Infection in Naive Human Cystic Fibrosis Airway Grafts," American Journal of Respiratory Cell and Molecular biology, vol. 23, (2000); pp. 121-127.

Traczewski et al., "In Vitro Activity of Doripenem Against Pseudomonas aeruginosa and Burkholderia cepacia Isolates from Both Cystic Fibrosis and Non-Cystic Fibrosis Patients," Antimicrobial Agents and Chemotherapy, (Feb. 2006) 50:819-821.

Tsai, et al., "Azitromycin Blocks Neutrophil Recruitment in Pseudomonas Endobronchial Infection", Am. J. Respir Crit. Care Med., 170:1331-9, (2004).

Tsapis et al., "Direct lung delivery of para-aminosalicylic acid by aerosol particles" Tuberculosis (Edinburgh, Scotland) (England) (2003) 83(6):379-85. (Abstract Only).

Tu et al.: "Development of fucosyltransferase and fucosidase inhibitors", Chem. Soc. Rev., Apr. 15, 2013 (Apr. 15, 2013), pp. 1-17, XP009168995, ISSN: 0303-0012, DOI: 10.1039/c3cs60056d [retrieved on Apr. 15, 2013] p. 2, section 1; pp. 12-14, section 7, including figures 11 to 13. Cited as common general knowledge.

Turel et al., "Biological activity of some magnesium(II) complexes of quinolones", The Synthesis and Biological Activity of Some Magnesium (II) Complexes of Quinolones—Metal-Based Drugs (2000) 7(2):101-104.

Turel, "The Interactions of Metal Ions with Quinolone Antibacterial Agents", Coordinatuion Chemistry Reviews, 232:27-47, (Oct. 2002).

U.S. Appl. No. 13/278,706; Advisory Action dated Mar. 7, 2016; 4 pages.

U.S. Appl. No. 13/278,706; Advisory Action dated May 12, 2017; 3 pages.

U.S. Appl. No. 13/278,706; Applicant Initiated Interview Summary dated Dec. 12, 2012; 3 pages.

U.S. Appl. No. 13/278,706; Applicant Initiated Interview Summary dated Feb. 5, 2013; 3 pages.

U.S. Appl. No. 13/278,706; Declaration of Michael Dudley, David Griffith, and Olga Rodny Under 37 C.F.R. Section 1.132; signed Feb. 22, 2016; 2 pages.

U.S. Appl. No. 13/278,706; Examiner Initiated Interview Summary dated Sep. 22, 2014; 2 pages.

U.S. Appl. No. 13/278,706; Final Office Action dated Mar. 2, 2017; 24 pages.

U.S. Appl. No. 13/278,706; Final Office Action dated Nov. 2, 2015; 20 pages.

U.S. Appl. No. 13/278,706; Final Office Action dated Oct. 18, 2012; 31 pages.

U.S. Appl. No. 13/278,706; Non-Final Office Action dated Mar. 5, 2015; 15 pages.

U.S. Appl. No. 13/278,706; Non-Final Office Action dated May 23, 2012; 22 pages.

U.S. Appl. No. 13/278,706; Non-Final Office Action dated Sep. 21, 2106; 20 pages.

U.S. Appl. No. 13/278,706; Notice of Allowance dated Feb. 19, 2013; 9 pages.

U.S. Appl. No. 13/278,706; Notice of Appeal dated Aug. 31, 2017; 2 pages.

U.S. Appl. No. 13/278,706; Notice of Appeal dated Feb. 24, 2016; 1 page.

U.S. Appl. No. 15/623,168; Corrected Notice of Allowability, dated Dec. 5, 2018; 8 pages.

U.S. Appl. No. 15/623,168; Non-Final Office Action dated Mar. 12, 2018; 12 pages.

U.S. Appl. No. 15/623,168; Notice of Allowance dated Nov. 1, 2018; 22 pages.

U.S. Appl. No. 13/412,423; Non-Final Office Action dated Apr. 1, 2015; 25 pages.

U.S. Appl. No. 13/412,423; Non-Final Office Action dated May 11, 2016; 18 pages.

U.S. Appl. No. 13/412,423; Notice of Allowance dated Mar. 6, 2017; 4 pages.

U.S. Appl. No. 13/412,423; Notice of Allowance dated Mar. 3, 2017; 8 pages.

U.S. Appl. No. 12/574,666; Applicant Initiated Interview Summary dated Jun. 12, 2013; 3 pages.

U.S. Appl. No. 12/574,666; Final Office Action dated May 17, 2012; 22 pages.

U.S. Appl. No. 12/574,666; Non-Final Office Action dated Mar. 13, 2013; 23 pages.

U.S. Appl. No. 12/574,666; Non-Final Office Action dated Nov. 29, 2011; 21 pages.

U.S. Appl. No. 12/574,666; Notice of Allowance dated Sep. 23, 2013; 12 pages.

U.S. Appl. No. 11/436,875; Applicant Initiated Interview Summary dated Apr. 30, 2010; 1 page.

U.S. Appl. No. 11/436,875; Applicant Initiated Interview Summary dated Jul. 27, 2010; 3 pages.

U.S. Appl. No. 11/436,875; Examiner Interview Summary Report dated Apr. 21, 2010; 4 pages.

U.S. Appl. No. 11/436,875; Examiner Interview Summary Report dated Aug. 5, 2010; 2 pages.

U.S. Appl. No. 11/436,875; Non-Final Office Action dated Feb. 5, 2010; 29 pages.

U.S. Appl. No. 11/436,875; Notice of Allowance dated Aug. 5, 2010; 4 pages.

U.S. Appl. No. 11/436,875; Notice of Allowance dated Aug. 5, 2010; 5 pages.

U.S. Appl. No. 12/574,680; Final Office Action dated Jun. 5, 2012; 26 pages.

U.S. Appl. No. 12/574,680; Non-Final Office Action dated Nov. 4, 2011; 21 pages.

U.S. Appl. No. 12/574,680; Notice of Allowance dated Jun. 17, 2014; 9 pages.

U.S. Appl. No. 12/604, 324; Final Office Action dated Nov. 5, 2012; 16 pages.

U.S. Appl. No. 12/604, 324; Non-Final Office Action dated Apr. 12, 2012; 27 pages.

U.S. Appl. No. 12/604, 324; Notice of Allowance dated Jan. 25, 2013; 8 pages.

U.S. Appl. No. 12/604, 324; Notice of Allowance dated May 1, 2013; 9 pages.

U.S. Appl. No. 12/604,340; Non-Final Office Action dated Jan. 7, 2013; 16 pages.

U.S. Appl. No. 12/604,340; Non-Final Office Action dated Sep. 26, 2012; 11 pages.

U.S. Appl. No. 12/604,340; Notice of Allowance dated Jun. 3, 2013; 7 pages.

U.S. Appl. No. 12/604,347; Applicant Initiated Interview Summary dated Jan. 22, 2013; 3 pages.

U.S. Appl. No. 12/604,347; Non-Final Office Action dated Oct. 12, 2012; 14 pages.

U.S. Appl. No. 12/604,347; Notice of Allowance dated Apr. 30, 2013; 10 pages.

U.S. Appl. No. 12/604,347; Notice of Allowance dated Jan. 14, 2013; 10 pages.

U.S. Appl. No. 12/695,981; Final Office Action dated Jul. 5, 2012; 18 pages.

U.S. Appl. No. 12/695,981; Non-Final Office Action dated Nov. 16, 2011; 36 pages.

U.S. Appl. No. 12/695,981; Notice of Allowance dated Nov. 18, 2012; 7 pages.

U.S. Appl. No. 13/412,423; Advisory Action dated Apr. 7, 2016; 3 pages.

U.S. Appl. No. 13/412,423; Final Office Action dated Dec. 17, 2015; 29 pages.

U.S. Appl. No. 13/412,423; Final Office Action dated Oct. 16, 2014; 27 pages.

(56) References Cited

OTHER PUBLICATIONS

U.S. Appl. No. 13/412,423; Final Office Action dated Oct. 22, 2013; 21 pages.
U.S. Appl. No. 13/412,423; Non-Final Office Action dated Mar. 22, 2013; 22 pages.
U.S. Appl. No. 14/012,307; Advisory Action dated Feb. 2, 2016; 3 pages.
U.S. Appl. No. 14/012,307; Final Office Action dated Oct. 7, 2015; 26 pages.
U.S. Appl. No. 14/012,307; Non-Final Office Action dated Jun. 16, 2016; 26 pages.
U.S. Appl. No. 14/012,307; Non-Final Office Action dated May 20, 2015; 19 pages.
U.S. Appl. No. 14/012,307; Notice of Appeal dated Jan. 19, 2016; 1 page.
U.S. Appl. No. 14/134,348; Advisory Action dated May 9, 2016; 5 pages.
U.S. Appl. No. 14/134,348; Applicant Initiated Interview Summary dated Sep. 2, 2016; 3 pages.
U.S. Appl. No. 14/134,348; Final Office Action dated Mar. 4, 2016; 13 pages.
U.S. Appl. No. 14/134,348; Final Office Action dated Oct. 13, 2016; 10 pages.
U.S. Appl. No. 14/134,348; Non-Final Office Action dated Jul. 15, 2015; 17 pages.
U.S. Appl. No. 14/134,348; Non-Final Office Action dated Jul. 29, 2016; 11 pages.
U.S. Appl. No. 14/134,348; Notice of Appeal dated Apr. 11, 2017; 1 page.
U.S. Appl. No. 14/333,583; Examiner Initiated Interview Summary dated Mar. 21, 2016; 1 page.
U.S. Appl. No. 14/333,583; Non-Final Office Action dated Nov. 12, 2015; 11 pages.
U.S. Appl. No. 14/333,583; Notice of Allowance dated Mar. 21, 2016; 10 pages.
U.S. Appl. No. 15/132,122; Non-Final Office Action dated Oct. 4, 2016; 16 pages.
U.S. Appl. No. 15/132,122; Notice of Allowance dated Mar. 28, 2017; 9 pages.
U.S. Appl. No. 15/173,372; Final Office Action dated Jul. 17, 2018; 26 pages.
U.S. Appl. No. 15/173,372; Non-Final Office Action dated Nov. 13, 2017; 13 pages.
U.S. Appl. No. 15/225,188; Examiner Initiated Interview Summary dated Dec. 13, 2017; 2 pages.
U.S. Appl. No. 15/225,188; Non-Final Office Action dated Jul. 21, 2017; 15 pages.
U.S. Appl. No. 15/225,188; Notice of Allowance dated Dec. 13, 2017; 9 pages.
U.S. Appl. No. 15/635,818; Non-Final Office Action dated Mar. 28, 2018; 8 pages.
U.S. Appl. No. 15/729,930; Non-Final Office Action dated Mar. 20, 2019; 67 pages.
U.S. Appl. No. 16/194,954; Application as filed dated Nov. 19, 2018; 76 pages.
U.S. Appl. No. 16/250,520; Application as filed dated Jan. 17, 2019; 196 pages.
U.S. Appl. No. 13/412,423; Final Office Action dated Oct. 20, 2016; 16 pages.
U.S. Appl. No. 13/278,706; Non-Final Office Action, dated Dec. 12, 2018; 44 pages.
U.S. Appl. No. 13/412,423; Non-Final Office Action dated Feb. 20, 2014; 20 pages.
Urban C. et al., "Fluoroquinolone-Resistant *Streptococcus pneumoniae* Associated with Levofloxacin Therapy", The Journal of Infectious Diseases, 2001, vol. 184, No. 6, pp. 794-798.
Vaughan, "Nebulization of Antibiotics in Management of Sinusitis", Current Infectious Disease Reports, 6(3):187-90, (2004), (Abstract only).
Vaughan, et al., "Use of Nebulized Antibiotics for Acute Infections in Chronic Sinusitis", Otolaryngology—Head and Neck Surgery, 127:558-68, (2002).
Villeneuve, et al., "Nebulized Magnesium Sulfate in the Management of Acute Exacerbations of Asthma," The Annals of Pharmacotherapy, vol. 40, (Jun. 2006); p. 1118—(Abstract Only).
Vippagunta, et al. "Crystalline Solids," Advanced Drug Delivery Reviews, May 16, 2001, vol. 48, No. 1; pp. 3-26—(Abstract Only).
Wacker, J. et al., "Riboflavin deficiency and preeclampsia", Obstet Gynecol. 2000;96(1):38-44.
Wada et al., "Immunomodulatory Effect of Gatifloxacin on Mouse Peritoneal Macrophages in vitro and in Models of Endotoxin-Induced Rat Conjunctivitis and Rabbit Bacterial Keratitis," Opthalmic Research, vol. 40, (2008); pp. 54-60.
Wagner et al., (Clin Rev Allerg Immunol 2008, 35, 124-134).
Wahl et al. "New Medical Management Techniques for Acute Exacerbations of Chronic Rhinosinusitis", Current Opinion in Otolaryngology & Head and Neck Surgery (2003) 11:27-32.
Wang et al. "Synthesis and crystal structure of a new copper (II) complex containing fluoroquinolone", Inter'l Symposium on Solid State Chemistry in China; Frontiers of Solid State Chemistry, World Scientific (2002) 327-332.
Wang et al.: "Synthesis and Biological Evaluation of Glycosidase Inhibitors: gem—Difluoromethylenated Nojirimycin Analogues", J. Med. Chem., vol. 49, No. 10, May 1, 2006 pp. 2989-2997, XP55301961, US ISSN: 0022-2623, DOI: 10.1021/jm060066q p. 2989, left column, paragraphs 1-2; table 1: compound 41.
Weber A. et.al., "Effect of Nebulizer Type and Antibiotic Concentration on Device Performance", Pediatric Pulmonology, 23(4):249-60, (Apr. 1997).
Weber et al., "Nebulizer Delivery of Tobramycin to the Lower Respiratory Tract", Pediatric Pulmonology, Wiley-Liss, Inc. (1994) 17: p. 331-339.
Weiss, et al., "Anti-Inflammatory Effects of Moxifloxacin on Activated Human Monocytic Cells: Inhibition of NF-.kappa.B and Mitogen-Activated Protein Kinase Activation and of Synthesis of Proinflammatory Cytokines", Antimicrobial Agents and Chemotherapy, 48(6):1974-82, (2004).
Werber, et al., "Moxifloxacin Cytokine-Induced MAP Kinase and NF-.kappa.B Activation as well as Nitric Oxide Synthesis in a Human Respiratory Epithelial Cell Line", Journal of Antimicrobial Chemotherapy, 55(3):293-300, (2005).
Wilkinson, et al., "Airway Bacterial Load and FEV1 Decline in Patients with Chronic Obstructive Pulmonary Disease", American Journal of Respiratory and Critical Care Medicine, 167:1090-5, (2003).
Wilkinson, et al., "Effect of Interactions Between Lower Airway Bacterial and Rhinoviral Infection in Exacerbations of COPD," Chest, vol. 129, No. 2, (Feb. 2006); pp. 317-324.
Williams, Jr., "Fluoroquinolones for respiratory infections: too valuable to overuse", Chest (2001) 120(6):1771-5.
Wise, R., Merck online Manual Home Edition article, entitled, "Chronic Obstructive Pulmonary Disease," accessed on Mar. 21, 2010 at www.merck.com/mmhe/print/sec04/ch045/ch045a.html.
Wu et al.: "Rapid Diversity-Oriented Synthesis in Microtiter Plates for In Situ Screening: Discovery of Potent and Selective [alpha]-Fucosidase Inhibitors", Angew. Chem. Int. Ed., vol. 42, No. 38, 6 Oct. 6, 2003, pp. 4661-4664, XP055301569, DE ISSN: 1433-7851, DOI: 10.1002/anie, left column, paragraph 2; schemes 1 and 2; table 1.
Wu et al.: "Structural basis of alpha-fucosidase inhibition by iminocyclitols with K(i) values in the micro- to picomolar range", Angew. Chem. Int. Ed., vol. 49, No. 2, Jan. 8, 2010 (Jan. 8, 2010), pp. 337-340, XP009168699, ISSN: 1521-3773 [retrieved on Dec. 3, 2009].
Yamamoto, et al., "Treatment of respiratory and urinary tract infections in elderly inmates at a nursing home by selective antimicrobial agents based on the sensitivity of the isolated bacteria," Nippon Ronen Igakkai Zasshi, Japanese Journal of Geriatrics, vol. 44, No. 3, (2007); pp. 359-366-(Abstract Only).
Zach, M., "Discussion", Chest, vol. 94, No. 2, (Aug. 1988); pp. 160S-162S.

(56) References Cited

OTHER PUBLICATIONS

Zhang, et al., "Besifloxacin, A Novel Fluoroquinolone Antimicrobial Agent, Exhibits Potent Inhibition of Pro-Inflammatory Cytokines in Human THP-1 Monocytes", Journal of Antimicrobial Chemotherapy, 61:111-6, (2008).

Zhao, et al., "Description and Clinical Treatment of an Early Outbreak of Severe Acute Respiratory Syndrome (SARS) in Guangzhou, PR China," Journal of Medical Microbiology, vol. 52, No. 8, (2003); pp. 715-720.

Zheng, et al., "Pulmonary delivery of a dopamine D-1 agonist, ABT-431, in dogs and humansm" International Journal of Pharmaceutics, vol. 191, No. 2, (Nov. 30, 1999); pp. 131-140—(Abstract Only).

Zimmermann, et al., "Anti-Inflammatory Effects of Antibacterials on Human Bronchial Epithelial Cells", Respiratory Research, 10(89)1-8, (2009).

Zolkina, T.D. et al, "Cytochemical indicators of lymphocytes after inhalation of riboflavin-nucleotide and calcium pantothenate in children with bronchial asthma" Pediatriia, vol. 8 (1987) pp. 108-109.

Heeckeren, A. et al., "Excessive Inflammatory Response of Cystic Fibrosis Mice to Bronchopulmonary Infection with Pseudomonas Aeruginosa", J Clin Invest., 100(11):2810-15, (1997).

Mogayzel, P. et al., "Pulmonary and Critical Care Updates: Update in Cystic Fibrosis 2009", Am J Respir Cult Care Med., 181(6):539-544, (2010).

U.S. Appl. No. 15/729,930; Final Office Action, dated Oct. 25, 2019; 29 pages.

U.S. Appl. No. 16/194,954; Non-Final Office Action, dated Aug. 29, 2019; 43 pages.

U.S. Appl. No. 161194,954; Notice of Allowance, dated Mar. 17, 2020; 8 pages.

U.S. Appl. No. 16/796,525; Application as filed, dated Feb. 20, 2020; 14 pages.

\* cited by examiner

USE OF AEROSOLIZED LEVOFLOXACIN FOR TREATING CYSTIC FIBROSIS

RELATED APPLICATIONS

This application is a continuation of U.S. application Ser. No. 15/623,168, filed Jun. 14, 2017, issued as U.S. Pat. No. 10,231,975, which is a continuation of U.S. application Ser. No. 13/412,423 filed Mar. 5, 2012, issued as U.S. Pat. No. 9,700,564, which is a continuation of PCT International Application No. PCT/US2010/047903 filed Sep. 3, 2010, which claims priority to U.S. Application No. 61/240,092 filed Sep. 4, 2009, and U.S. Application No. 61/249,231 filed Oct. 6, 2009, which are hereby expressly incorporated by reference in their entireties.

FIELD OF THE INVENTION

Methods and compositions for treating cystic fibrosis are provided. In particular, compositions and methods for the use of aerosolized levofloxacin for treating cystic fibrosis are provided.

BACKGROUND

Patients with cystic fibrosis (CF) suffer from chronic infections of the lower respiratory tract that can be caused by bacteria, including *Pseudomonas aeruginosa*. *Pseudomonas aeruginosa* has been particularly problematic to eradicate and has been implicated as the major cause of morbidity and mortality in CF patients.

Aerosol delivery of antibiotics directly to the lungs has the potential to increase the local concentration of antibiotic at the site of infection, thereby, enhancing bacterial killing compared with systemic administration. Currently, tobramycin solution for inhalation is the only aerosol antibiotic approved for the management of CF patients with bacteria such as *P. aeruginosa*. Because of the development of resistance to tobramycin and the limited effect on reducing bacterial density in sputum, there is a need for improved therapies to treat CF patients with pulmonary infections caused by multidrug resistant bacteria, including *P. aeruginosa*.

SUMMARY

Some embodiments of the present invention relate to compositions, use of such compositions, and methods for treating cystic fibrosis. Some such embodiments include compositions and methods for the use of aerosolized levofloxacin for treating cystic fibrosis.

Some embodiments include methods for treating cystic fibrosis in a human in which the human has a pulmonary infection comprising *P. aeruginosa*. In some such embodiments, the methods includes administering to said human in need thereof an aerosol of a solution comprising levofloxacin or ofloxacin and a divalent or trivalent cation to achieve a reduction in the density of the *P. aeruginosa* in the sputum of said human by at least 40%, at least 44%, at least 70%, at least 900/% and at least 97%. Some such embodiments include achieving a reduction in the density of the *P. aeruginosa* in the sputum of said human by at least 0.25 $\log_{10}$ CFU/g sputum, at least 0.50 $\log_{10}$ CFU/g sputum, at least 1.0 $\log_{10}$ CFU/g sputum, at least 1.5 $\log_{10}$ CFU/g sputum, and at least 1.8 $\log_{10}$ CFU/g sputum.

Some embodiments include methods for treating cystic fibrosis in a human that include administering to the human in need thereof an aerosol of a solution comprising levofloxacin or ofloxacin and a divalent or trivalent cation to achieve an increase in $FEV_1$ of at least 2% and an increase in FEF 25-75 of at least 5%, an increase in $FEV_1$ of at least 5% and an increase in FEF 25-75 of at least 10%, an increase in $FEV_1$ of at least 7% and an increase in FEF 25-75 of at least 15%, and an increase in $FEV_1$ of at least 10%, and an increase in FEF 25-75 of at least 20%.

Some embodiments include achieving an increase in $FEV_1$ of at least 0.05 L and an increase in FEF 25-75 of at least 0.05 L, an increase in $FEV_1$ of at least 0.10 L and an increase in FEF 25-75 of at least 0.10 L, an increase in $FEV_1$ of at least 0.15 L and an increase in FEF 25-75 of at least 0.15 L, an increase in $FEV_1$ of at least 0.20 L and an increase in FEF 25-75 of at least 0.20 L, and an increase in $FEV_1$ of at least 0.25 L and an increase in FEF 25-75 of at least 0.25 L. Some embodiments include achieving an increase in FEF 25-75 of at least 0.27 L.

Some embodiments include methods for treating cystic fibrosis in a human that include administering to said human in need thereof an aerosol of a solution comprising levofloxacin or ofloxacin and a divalent or trivalent cation to achieve a hazard ratio less than 1.0, wherein the hazard ratio is indicative of a decreased need for other anti-pseudomonal antimicrobials. In some such embodiments, the hazard ratio is less than 0.8, less than 0.6, less than 0.4, and less than 0.3.

Some embodiments include methods of treating cystic fibrosis in a human who is being administered an agent by inhalation selected from the group consisting of one or more of dornase alpha, azithromycin, salbutamol, pancrelipase, sodium chloride, seretide, and ADEK, comprising administering to said human an aerosol of a solution comprising levofloxacin or ofloxacin and a divalent or trivalent cation. In some embodiments, the agent is selected from the group consisting of salbutamol, pancrelipase, seretide, and ADEK. In some embodiments, the human has a pulmonary infection comprising *P. aeruginosa*. Some embodiments include achieving a reduction in the density of the *P. aeruginosa* in the sputum of said human by at least 0.25 $\log_{10}$ CFU/g sputum, at least 0.50 $\log_{10}$ CFU/g sputum, and at least 1.0 $\log_{10}$ CFU/g sputum.

Some embodiments include methods for treating cystic fibrosis in a human in which the human has a pulmonary infection comprising *P. aeruginosa*. Some such embodiments include repeatedly administering to said human in need thereof an aerosol of a solution comprising levofloxacin or ofloxacin and a divalent or trivalent cation, wherein said repeated administration does not result in a greater than 16-fold increase in minimum inhibitory concentration (MIC) of the *P. aeruginosa* strain in said human having the highest MIC relative to other *P. aeruginosa* strains. In some embodiments, the repeated administration does not result in a greater than 8-fold increase in minimum inhibitory concentration (MIC) of the *P. aeruginosa* strain in said human having the highest MIC relative to other *P. aeruginosa* strains. In some embodiments, repeated administration does not result in a greater than 4-fold increase in minimum inhibitory concentration (MIC) of the *P. aeruginosa* strain in said human having the highest MIC relative to other *P. aeruginosa* strains.

Some embodiments include methods for treating cystic fibrosis in a human in which the human has a pulmonary infection comprising *P. aeruginosa*. Some such embodiments include repeatedly administering to said human in need thereof an aerosol of a solution comprising levofloxacin or ofloxacin and a divalent or trivalent cation to achieve an increase in a CFQ-R respiratory domain greater than 1, greater than 2, greater than 3, greater than 4, and greater than 5.

Some embodiments include methods of decreasing small airway resistance in a human with cystic fibrosis, comprising administering to said human in need thereof an aerosol of a solution comprising levofloxacin or ofloxacin and a divalent or trivalent cation to achieve an increase in FEF 25-75 of at least 5%, at least 10%, at least 15%, and at least 20%. Some embodiments include, achieving an increase in FEF 25-75 of at least 0.05 L, at least 0.10 L, at least 0.15 L, at least 0.20 L, at least 0.25 L, and at least 0.27 L.

Some embodiments include methods of administering levofloxacin or ofloxacin to a human, comprising repeatedly administering to said human an aerosol of a solution comprising levofloxacin or ofloxacin and a divalent or trivalent cation, wherein said repeated administration does not result in an incidence of arthralgia. In some methods, administering is repeated at least once daily for 14 days, at least once daily for 28 days, and at least once daily for 35 days. In some such methods, administering is repeated at least twice daily for 14 days, at least twice daily for 28 days, and at least twice daily for 35 days.

Some embodiments include methods for treating cystic fibrosis in a human in which the human has a pulmonary infection comprising P. aeruginosa and said human has a body surface area less than 1.5 m². Some such methods include administering to said human in need thereof an aerosol of a solution comprising levofloxacin or ofloxacin and a divalent or trivalent cation to achieve a dose-normalized serum AUC at least 20 (ng·h/L)/mg Dose. In some embodiments, the administering is repeated daily for at least 14 days the aerosol comprises an amount of levofloxacin or ofloxacin of at least 80 mg, 120 mg, 180 mg, and 240 mg. Some embodiments include achieving a dose-normalized serum AUC at least 20 (ng·h/L)/mg Dose, at least 40 (ng·h/L)/mg Dose, at least 60 (ng·h/L)/mg Dose, at least 80 (ng·h/L)/mg Dose, and at least 100 (ng·h/L)/mg Dose.

Some embodiments include methods for treating cystic fibrosis in a human in which the human has a pulmonary infection comprising P. aeruginosa and the human has a body surface area less than 1.5 m$_2$. Some such methods include administering to said human in need thereof an aerosol of a solution comprising levofloxacin or ofloxacin and a divalent or trivalent cation to achieve a dose-normalized serum $C_{max}$ greater than 2 µg/L/mg administered dose greater than 4 µg/L/mg administered dose, greater than 6 µg/L/mg administered dose, greater than 8 µg/L/mg administered dose, and greater than 14 µg/L/mg administered dose. In some embodiments, the human is less than 15 years of age, less than 12 years of age, less than 10 years of age. In some embodiments, the human comprises a mass less than 55 kg, less than 45 kg, less than 35 kg, less than 25 kg.

In some of the foregoing embodiments, the solution consists essentially of levofloxacin or ofloxacin and the divalent or trivalent cation.

In some of the foregoing embodiments, the solution comprises no lactose.

In some of the foregoing embodiments, the solution comprises a divalent or trivalent cation concentration from about 50 mM to about 400 mM, and a levofloxacin or ofloxacin concentration from between about 50 mg/ml to about 200 mg/ml.

In some of the foregoing embodiments, the solution comprises a divalent or trivalent cation concentration from about 100 mM to about 300 mM, and a levofloxacin or ofloxacin concentration from between about 75 mg/ml to about 150 mg/ml.

In some of the foregoing embodiments, the solution comprises a divalent or trivalent cation concentration from about 150 mM to about 250 mM, and a levofloxacin or ofloxacin concentration from between about 90 mg/ml to about 125 mg/ml.

In some of the foregoing embodiments, wherein the solution comprises an osmolality from about 300 mOsmol/kg to about 500 mOsmol/kg, and a pH from about 5 to about 8.

In some of the foregoing embodiments, the solution comprises an osmolality from about 350 mOsmol/kg to about 425 mOsmol/kg, and a pH from about 5 to about 6.5.

In some of the foregoing embodiments, the solution comprises a pH from about 5.5 to about 6.5.

In some of the foregoing embodiments, the divalent or trivalent cation is selected from magnesium, calcium, zinc, copper, aluminum, and iron.

In some of the foregoing embodiments, the solution comprises magnesium chloride.

In some of the foregoing embodiments, the solution comprises a levofloxacin or ofloxacin concentration between about 90 mg/ml to about 110 mg/ml, a magnesium chloride concentration between about 175 mM to about 225 mM, a pH between about 5 to about 7; an osmolarity of between about 300 mOsmol/kg to about 500 mOsmol/kg, and lacks lactose.

In some of the foregoing embodiments, the aerosol comprises a mass median aerodynamic diameter from about 2 microns to about 5 microns with a geometric standard deviation less than or equal to about 2.5 microns.

In some of the foregoing embodiments, the aerosol comprises a mass median aerodynamic diameter from about 2.5 microns to about 4.5 microns with a geometric standard deviation less than or equal to about 1.8 microns.

In some of the foregoing embodiments, the aerosol comprises a mass median aerodynamic diameter from about 2.8 microns to about 4.3 microns with a geometric standard deviation less than or equal to about 2 microns.

Some of the foregoing embodiments also include producing the aerosol with a vibrating mesh nebulizer. In some such embodiments, the vibrating mesh nebulizer is a PARI E-FLOW® nebulizer.

In some of the foregoing embodiments, the amount of levofloxacin or ofloxacin administered to the lung is at least about 20 mg, at least about 100 mg, at least about 125 mg, and at least about 150 mg.

In some of the foregoing embodiments, at least about 100 mg the aerosol is administered to the lung in less than about 10 minutes, less than about 5 minutes, less than about 3 minutes, less than about 2 minutes.

Some of the foregoing embodiments also include co-administering an additional active agent selected from the group consisting of antibiotics, bronchodilators, anticholinergics, glucocorticoids, eicosanoid inhibitors, and combinations thereof.

In some embodiments, the antibiotic can include tobramycin, aztreonam, ciprofloxacin, azithromycin, tetracycline, quinupristin, linezolid, vancomycin, and chloramphenicol, colisitin and combinations thereof. In some embodiments, the bronchodilator can include salbutamol, levosalbuterol, terbutaline, fenoterol, terbutlaine, pirbuterol, procaterol, bitolterol, rimiterol, carbuterol, tulobuterol, reproterol, salmeterol, formoterol, arformoterol, bambuterol, clenbuterol, indacterol, theophylline, roflumilast, cilomilast, and combinations thereof. In some embodiments, the anticholinergic can include ipratropium, tiotropium, and combinations thereof. In some embodiments, the glucocorticoid can include prednisone, fluticasone, budesonide, mometasone, ciclesonide, beclomethasone, and combinations thereof in some embodiments, the eicosanoid can include montelukast, pranlukast, zafirlukast, zileuton, ramatroban, seratrodast, and combinations thereof. In some embodiments, co-administering comprises inhaling the additional active agent.

Some of the foregoing embodiments include administering the aerosol once daily.

Some of the foregoing embodiments administering the aerosol twice daily.

In some of the foregoing embodiments, the pulmonary infection further comprises one or more bacteria that can include *Pseudomonas fluorescens, Pseudomonas acidovorans, Pseudomonas alcaligenes*, and *Pseudomonas putida, Stenotrophomonas maltophilia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolvticus, Haemophilus ducreyi. Pasteurella multocida, Pasteurella haemolytica, Helicobacter pylori, Campylobacter fetus, Campylobacter jejuni, Campylobacter coli, Borrelia burgdorferi, Vibrio cholera, Vibrio parahaemolyticus, Legionella pneumophila, Listeria monocytogenes, Neisseria gonorrhoeae, Neisseria meningitidis, Burkholderia cepacia, Francisella tularensis, Kingella*, and *Morarella*.

In some of the foregoing embodiments, the pulmonary infection further comprises a gram-negative anaerobic bacteria.

In some of the foregoing embodiments, the pulmonary infection further comprises one or more of the bacteria that can include *Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii*, and *Bacteroides splanchnicus*.

In some of the foregoing embodiments, the pulmonary infection further comprises a gram-positive bacteria.

In some of the foregoing embodiments, the pulmonary infection further comprises one or more of the bacteria that can include *Corynebacterium diphtheriae, Corynebacterium ulcerans, Streptococcus pneumoniae, Streptococcus agalactiae. Streptococcus pyogenes, Streptococcus milleri; Streptococcus* (Group G); *Streptococcus* (Group C/F); *Enterococcus faecalis, Enterococcus faecium, Staphylococcus aureus, Staphylococcus epidermidis, Staphylococcus saprophyticus. Staphylococcus intermedius, Staphylococcus hyicus* subsp. *hyicus, Staphylococcus haemolyticus, Staphylococcus hominis*, and *Staphylococcus saccharolyticus*.

In some of the foregoing embodiments, the pulmonary infection further comprises a gram-positive anaerobic bacteria.

In some of the foregoing embodiments, the pulmonary infection further comprises one or more bacteria that can include *Clostridium difficile, Clostridium perfringens. Clostridium tetini*, and *Clostridium botulinum*.

In some of the foregoing embodiments, the pulmonary infection further comprises an acid-fast bacteria.

In some of the foregoing embodiments, the pulmonary infection further comprises one or more bacteria that can include *Mycobacterium tuberculosis, Mycobacterium avium, Mycobacterium intracellulare*, and *Mycobacterium leprae*.

In some of the foregoing embodiments, the pulmonary infection further comprises an atypical bacteria.

In some of the foregoing embodiments, the pulmonary infection further comprises one or more bacteria that can include *Chlamydia pneumoniae* and *Mycoplasma pneumoniae*.

BRIEF DESCRIPTION OF THE DRAWINGS

FIGS. 1A and 1B show graphs using linear axes and semi-logarithmic axes, respectively, of the arithmetic mean serum concentrations of levofloxacin after administration of single 180 mg doses as a 50 mg/ml and 100 mg/ml solution for inhalation and after administration of 240 mg as a 100 mg/ml solution for inhalation once daily for 7 days to patients with CF.

FIGS. 2A and 2B show graphs using linear axes and semi-logarithmic axes, respectively, of the arithmetic mean sputum concentrations of levofloxacin after administration of single 180 mg doses as a 50 mg/ml and 100 mg/ml solution for inhalation and after administration of 240 mg as a 100 mg/ml solution for inhalation once daily for 7 days to patients with CF.

FIG. 3 shows a graph of the mean change in *P. aeruginosa* (log 10 CFU/g sputum) over time for various treatment arms in an EE patient population. Patients were administered: levofloxacin 120 mg QD, levofloxacin 240 mg QD, levofloxacin 240 mg BID, or placebo.

FIG. 4 shows a graph of change in *P. aeruginosa* (log 10 CFU/g sputum) over time for various treatment arms in a MITT patient population. Patients were administered: levofloxacin 120 mg QD, levofloxacin 240 mg QD, levofloxacin 240 mg BID, or placebo.

FIG. 5 shows a graph of survival distribution function over time for various treatment groups in an EE population. The x-axis is the Time to Need for Anti-Pseudomonal Antimicrobials in days. The y-axis is the Survival Distribution Function.

FIG. 6 shows a graph of survival distribution function over time for various treatment groups in a MITT population. The x-axis is the Time to Need for Anti-Pseudomonal Antimicrobials in days. The y-axis is the Survival Distribution Function.

FIG. 7 shows a graph of percent change in $FEV_1$(L) at Day 28 for the EE population treated with placebo, 120 mg QD, 240 mg QD, or 240 mg BID.

FIG. 8 shows a graph of percent change in $FEV_1$(L) vs. placebo at Day 28 for the EE population treated with 120 mg QD, 240 mg QD, or 240 mg BID. *p=0.0102.

FIG. 9 shows a graph of the categorical change in percent predicted $FEV_1$ at Day 28 for the EE population treated with 120 mg QD, 240 mg QD, or 240 mg BID. *p=0.0370, **p=0.0037.

FIG. 10 shows a graph of dose normalized serum AUC (ng·h/L/mgDose) vs. pediatric CF patient body weight (■ 180 mg (n=7); ♦ 240 mg (n=18)). The mean value is shown for serum levofloxacin AUC in adult CF patients studied in another clinical trial (not shown) and based on a mean weight of 71 kg (▲; +/−standard deviation).

Figure 11A:
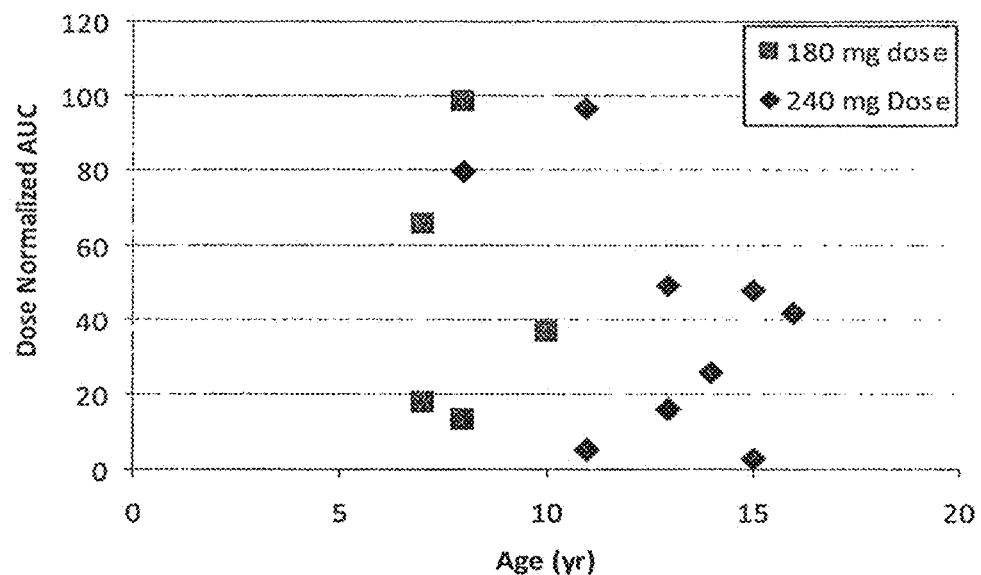
Figure 11B:
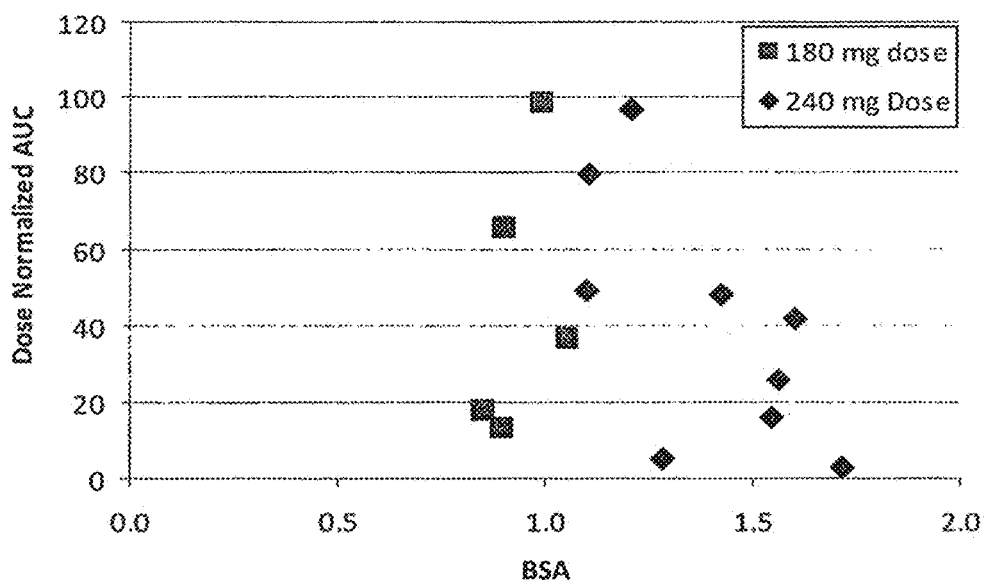
Figure 11C:
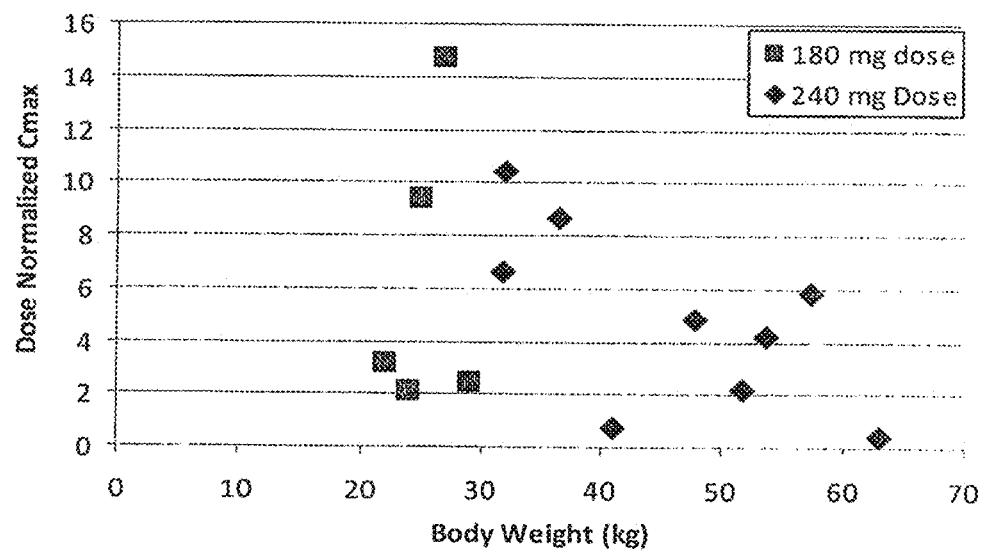
Figure 11D:
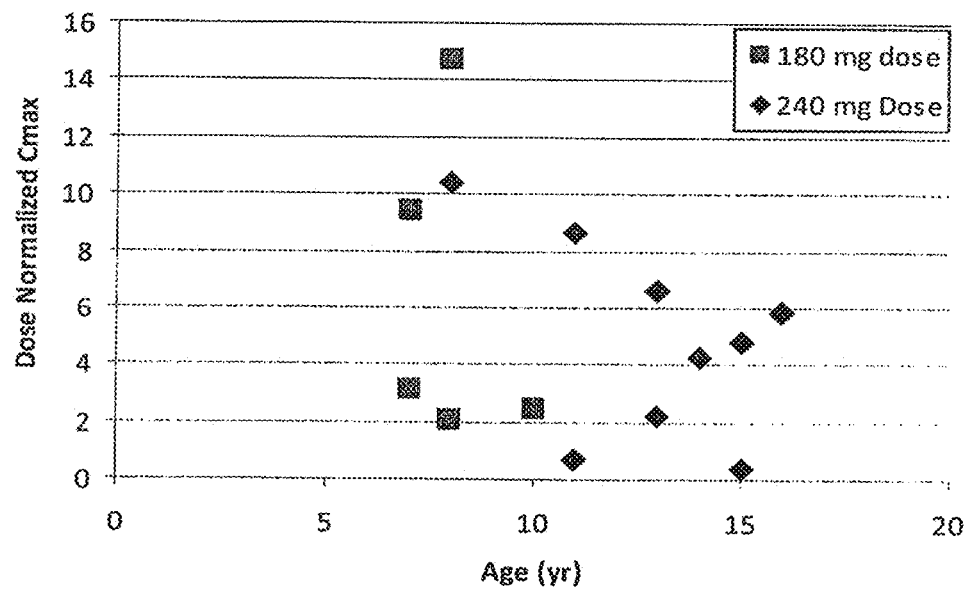
Figure 11E:
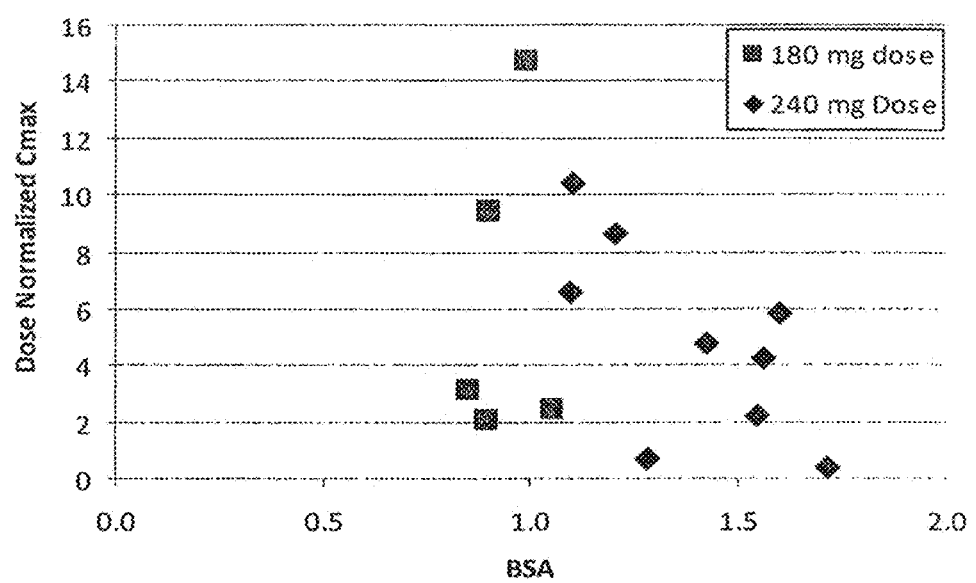

FIG. 11A shows a graph of dose normalized serum AUC (ng·h/L/mgDose) vs. pediatric CF patient age (■ 180 mg; ◆ 240 mg). FIG. 11B shows a graph of dose normalized serum AUC (ng·h/L/mg Dose) vs. BSA (body surface area) (■ 180 mg; ◆ 240 mg). FIG. 11C shows a graph of dose normalized serum $C_{max}$ (µ/L/mg administered dose) vs. pediatric CF patient body weight (■ 180 mg; ◆ 240 mg). FIG. 11D shows a graph of dose normalized serum $C_{max}$ (µ/L/mg administered dose) vs. pediatric CF patient age (■ 180 mg; ◆ 240 mg). FIG. 11E shows a graph of dose normalized serum $C_{max}$ (µg/L/mg administered dose) vs. BSA (■ 180 mg; ◆ 240 mg).

DETAILED DESCRIPTION

The present invention relates to the use of particular formulations of levofloxacin solutions for inhalation and particular dosage and administration regimens for the treatment of cystic fibrosis. In some embodiments, treatment of cystic fibrosis includes treatment of pulmonary infections associated with cystic fibrosis, such as *P. aeruginosa, S. pneumoniae, H influenzae, Burkholderia* sp., *Staphylococcus aureus, Stenotrophomonas* sp., and *M. catarrhalis*. Methods described herein for treating cystic fibrosis can include administering formulations of levofloxacin. In some embodiments, methods for treating cystic fibrosis can also include achieving a reduction in the density of particular pathogens in the lungs of a subject. In some embodiments, methods for treating cystic fibrosis can also include improving pulmonary characteristics of a subject that can be measured with parameters such as $FEV_1$, FEF 25-72, and the like.

The present invention provides several advantages. For example, aerosol levofloxacin provides high doses of drug directly to the lung. High doses are advantageous in reducing the development of resistant strains. In addition, the present invention provides formulations with reduced adverse effects typically associated with fluoroquinolones, such as arthralgia. Some embodiments provide methods for treating cystic fibrosis that decrease the risk of acute exacerbations in CF patients at risk for exacerbations. More embodiments provide methods for increasing the airflow in the lungs of CF patients. In various embodiments, the above methods are achieved by administering aerosolized levofloxacin or ofloxacin in dosages and administration schedules sufficient to achieve the recited result.

Definitions

The term "administration" or "administering" refers to a method of giving a dosage of an antimicrobial pharmaceutical composition to a vertebrate. The preferred method of administration can vary depending on various factors, e.g., the components of the pharmaceutical composition, the site of the potential or actual bacterial infection, the microbe involved, and the severity of an actual microbial infection. In some embodiments, administration can include loading an instrument to deliver a drug to a subject. In some such embodiments, administering can include loading a nebulizer with a drug to be delivered to a patient. Thus, the dosage administered may be the dosage loaded into the instrument (e.g., nebulizer).

A "carrier" or "excipient" is a compound or material used to facilitate administration of the compound, for example, to increase the solubility of the compound. Solid carriers include, e.g., starch, lactose, dicalcium phosphate, sucrose, and kaolin. Liquid carriers include, e.g., sterile water, saline, buffers, non-ionic surfactants, and edible oils such as oil, peanut and sesame oils. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, incorporated by reference herein in its entirety.

A "diagnostic" as used herein is a compound, method, system, or device that assists in the identification and characterization of a health or disease state. The diagnostic can be used in standard assays as is known in the art.

The term "mammal" is used in its usual biological sense. Thus, it specifically includes humans, cattle, horses, dogs, and cats, but also includes many other species.

The term "microbial infection" refers to the undesired proliferation or presence of invasion of pathogenic microbes in a host organism. This includes the excessive growth of microbes that are normally present in or on the body of a mammal or other organism. More generally, a microbial infection can be any situation in which the presence of a microbial population(s) is damaging to a host mammal. Thus, a microbial infection exists when excessive numbers of a microbial population are present in or on a mammal's body, or when the effects of the presence of a microbial population(s) is damaging the cells or other tissue of a mammal.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "pharmaceutically acceptable salt" refers to salts that retain the biological effectiveness and properties of the compounds of this invention, and which are not biologically or otherwise undesirable. In many cases, the compounds of this invention are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, naphtoic acid, oleic acid, palmitic acid, pamoic (emboic) acid, stearic acid, glycolic acid, pyruvic acid, oxalic acid, maleic acid, malonic acid, succinic acid, fumaric acid, tartaric acid, citric acid, ascorbic acid, glucoheptonic acid, glucuronic acid, lactic acid, lactobioic acid, tartaric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, histidine, arginine, lysine, benethamine, N-methyl-glucamine, and ethanolamine. Other acids include dodecylsufuric acid, naphthalene-1,5-disulfonic acid, naphthalene-2-sulfonic acid, and saccharin.

"Solvate" refers to the compound formed by the interaction of a solvent and fluoroquinolone antimicrobial, a metabolite, or salt thereof. Suitable solvates are pharmaceutically acceptable solvates including hydrates.

In the context of the response of a microbe, such as a bacterium, to an antimicrobial agent, the term "susceptibility" refers to the sensitivity of the microbe for the presence of the antimicrobial agent. So, to increase the susceptibility means that the microbe will be inhibited by a lower concentration of the antimicrobial agent in the medium surrounding the microbial cells. This is equivalent to saying that the microbe is more sensitive to the antimicrobial agent. In most cases the minimum inhibitory concentration (MIC) of that antimicrobial agent will have been reduced. The $MIC_{90}$ can include the concentration to inhibit growth in 90% of organisms.

By "therapeutically effective amount" or "pharmaceutically effective amount" is meant a fluoroquinolone antimicrobial agent, as disclosed for this invention, which has a therapeutic effect. The doses of fluoroquinolone antimicrobial agent which are useful in treatment are therapeutically effective amounts. Thus, as used herein, a therapeutically effective amount means those amounts of fluoroquinolone antimicrobial agent which produce the desired therapeutic effect as judged by clinical trial results and/or model animal infection studies. In particular embodiments, the fluoroquinolone antimicrobial agent are administered in a pre-determined dose, and thus a therapeutically effective amount would be an amount of the dose administered. This amount and the amount of the fluoroquinolone antimicrobial agent can be routinely determined by one of skill in the art, and will vary, depending on several factors, such as the particular microbial strain involved. This amount can further depend upon the patient's height, weight, sex, age and medical history. For prophylactic treatments, a therapeutically effective amount is that amount which would be effective to prevent a microbial infection.

A "therapeutic effect" relieves, to some extent, one or more of the symptoms of the infection, and includes curing an infection. "Curing" means that the symptoms of active infection are eliminated, including the total or substantial elimination of excessive members of viable microbe of those involved in the infection to a point at or below the threshold of detection by traditional measurements. However, certain long-term or permanent effects of the infection may exist even after a cure is obtained (such as extensive tissue damage). As used herein, a "therapeutic effect" is defined as a statistically significant reduction in bacterial load in a host, emergence of resistance, or improvement in infection symptoms as measured by human clinical results or animal studies.

"Treat," "treatment," or "treating," as used herein refers to administering a pharmaceutical composition for prophylactic and/or therapeutic purposes. The term "prophylactic treatment" refers to treating a patient who is not yet infected, but who is susceptible to, or otherwise at risk of, a particular infection such that there is a reduced onset of infection. The term "therapeutic treatment" refers to administering treatment to a patient already suffering from an infection. Thus, in preferred embodiments, treating is the administration to a mammal (either for therapeutic or prophylactic purposes) of therapeutically effective amounts of a fluoroquinolone antimicrobial agent.

Pharmacokinetics (PK) is concerned with the time course of antimicrobial concentration in the body. Pharmacodynamics (PD) is concerned with the relationship between pharmacokinetics and the antimicrobial efficacy in vivo. PK/PD parameters correlate antimicrobial exposure with antimicrobial activity. The rate of killing by antimicrobial is dependent on antimicrobial mode of action and is determined by either the length of time necessary to kill (time-dependent) or the effect of increasing concentrations (concentration-dependent). To predict the therapeutic efficacy of antimicrobials with diverse mechanisms of action different PK/PD parameters may be used. PK/PD parameters may be used to determine the bioavailability of antimicrobial compositions, for example, bioavailability of a composition in the pulmonary system, and/or bioavailability of a composition in plasma/serum.

"AUC/MIC ratio" is one example of a PK/PD parameter. AUC is defined as the area under the plasma/serum or site-of-infection concentration-time curve of an antimicrobial agent in vivo (in animal or human). For example, the site of infection and/or the site where concentration is measured can include portions of the pulmonary system, such as bronchial fluid and/or sputum. Accordingly, AUC may include serum AUC, and pulmonary AUC. $AUC_{(0-t)}$ can include the area under curve for time zero to a specific time 't.' $AUC_{(0-inf)}$ can include the area under curve from time zero to infinity. AUC/MIC ratio is determined by dividing the 24-hour-AUC for an individual antimicrobial by the MIC for the same antimicrobial determined in vitro. Activity of antimicrobials with the dose-dependent killing (such as fluoroquinolones) is well predicted by the magnitude of the AUC/MIC ratio.

"$C_{max}$:MIC" ratio is another PK:PD parameter. It describes the maximum drug concentration in plasma or tissue relative to the MIC. Fluoroquinolones and aminoglycosides are examples where $C_{max}$:MIC may predict in vivo bacterial killing where resistance can be suppressed.

"Time above MIC" (T>MIC) is another PK/PD parameter. It is expressed as a percentage of a dosage interval in which the plasma or site-of-infection level exceeds the MIC. Activity of antimicrobials with the time-dependent killing (such as beta-lactams or oxazolidinones) is well predicted by the magnitude of the T>MIC ratio.

The term "dosing interval" refers to the time between administrations of the two sequential doses of a pharmaceutical's during multiple dosing regimens. For example, in the case of orally administered ciprofloxacin, which is administered twice daily (traditional regimen of 400 mg b.i.d) and orally administered levofloxacin, which is administered once a day (500 mg or 750 mg q.d.), the dosing intervals are 12 hours and 24 hours, respectively.

As used herein, the "peak period" of a pharmaceutical's in vivo concentration is defined as that time of the pharmaceutical dosing interval when the pharmaceutical concentration is not less than 50% of its maximum plasma or site-of-infection concentration. In some embodiments, "peak period" is used to describe an interval of antimicrobial dosing.

The "respirable delivered dose" is the amount of drug inhaled during the inspiratory phase of the breath simulator that is equal to or less than 5 microns using a simulator programmed to the European Standard pattern of 15 breaths per minute, with an inspiration to expiration ratio of 1:1.

Pharmaceutical Compositions

For purposes of the method described herein, a fluoroquinolone antimicrobial agent formulated with a divalent or trivalent cation having improved pulmonary bioavailability may be administered using an inhaler. In some embodiments, a fluoroquinolone antimicrobial disclosed herein is produced as a pharmaceutical composition suitable for aerosol formation, good taste, storage stability, and patient safety and tolerability. In some embodiments, the isoform content of the manufactured fluoroquinolone may be optimized for tolerability, antimicrobial activity and stability.

Formulations can include a divalent or trivalent cation. The divalent or trivalent cation can include, for example, magnesium, calcium, zinc, copper, aluminum, and iron. In some embodiments, the solution comprises magnesium chloride, magnesium sulfate, zinc chloride, or copper chloride. In some embodiments, the divalent or trivalent cation concentration can be from about 25 mM to about 400 mM, from about 50 mM to about 400 mM, from about 100 mM to about 300 mM, from about 100 mM to about 250 mM, from about 125 mM to about 250 mM, from about 150 mM to about 250 mM, from about 175 mM to about 225 mM, from about 180 mM to about 220 mM, and from about 190 mM to about 210 mM. In some embodiments, the magnesium chloride, magnesium sulfate, zinc chloride, or copper chloride can have a concentration from about 5% to about 25%, from about 10% to about 200/%, and from about 15% to about 20%. In some embodiments, the ratio of fluoroquinolone to divalent or trivalent cation can be 1:1 to 2:1 or 1:1 to 1:2.

Non-limiting fluoroquinolones for use as described herein include levofloxacin, ofloxacin, ciprofloxacin, enoxacin, gatifloxacin, gemifloxacin, lomefloxacin, moxifloxacin, norfloxacin, pefloxacin, sparfloxacin, garenoxacin, sitafloxacin, and DX-619.

The formulation can have a fluoroquinolone concentration, for example, levofloxacin or ofloxacin, greater than about 50 mg/ml, about 60 mg/ml, about 70 mg/ml, about 80 mg/ml, about 90 mg/ml, about 100 mg/ml, about 110 mg/ml, about 120 mg/ml, about 130 mg/ml, about 140 mg/ml, about 150 mg/ml, about 160 mg/ml, about 170 mg/ml, about 180 mg/ml, about 190 mg/ml, and about 200 mg/ml. In some embodiments, the formulation can have a fluoroquinolone concentration, for example, levofloxacin or ofloxacin, from about 50 mg/ml to about 200 mg/ml, from about 75 mg/ml to about 150 mg/ml, from about 80 mg/ml to about 125 mg/ml, from about 80 mg/ml to about 120 mg/ml, from about 90 mg/ml to about 125 mg/ml, from about 90 mg/ml to about 120 mg/ml, and from about 90 mg/ml to about 110 mg/ml.

The formulation can have an osmolality from about 300 mOsmol/kg to about 500 mOsmol/kg, from about 325 mOsmol/kg to about 450 mOsmol/kg, from about 350 mOsmol/kg to about 425 mOsmol/kg, and from about 350 mOsmol/kg to about 400 mOsmol/kg. In some embodiments, the osmolality of the formulation is greater than about 300 mOsmol/kg, about 325 mOsmol/kg, about 350 mOsmol/kg, about 375 mOsmol/kg, about 400 mOsmol/kg, about 425 mOsmol/kg, about 450 mOsmol/kg, about 475 mOsmol/kg, and about 500 mOsmol/kg.

The formulation can have a pH from about 4.5 to about 8.5, from about 5.0 to about 8.0, from about 5.0 to about 7.0, from about 5.0 to about 6.5, from about 5.5 to about 6.5, and from 6.0 to about 6.5.

The formulation can comprise a conventional pharmaceutical carrier, excipient or the like (e.g., mannitol, lactose, starch, magnesium stearate, sodium saccharine, talcum, cellulose, sodium crosscarmellose, glucose, gelatin, sucrose, magnesium carbonate, and the like), or auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate, and the like). In some embodiments, the formulation can lack a conventional pharmaceutical carrier, excipient or the like. Some embodiments include a formulation lacking lactose. Some embodiments comprise lactose at a concentration less than about 10%, 5%, 1%, or 0.1%. In some embodiments, the formulation can consist essentially of levofloxacin or ofloxacin and a divalent or trivalent cation.

In some embodiments, a formulation can comprise a levofloxacin concentration between about 75 mg/ml to about 150 mg/ml, a magnesium chloride concentration between about 150 mM to about 250 mM, a pH between about 5 to about 7; an osmolality of between about 300 mOsmol/kg to about 500 mOsmol/kg, and lacks lactose.

In some embodiments, a formulation comprises a levofloxacin concentration about 100 mg/ml, a magnesium chloride concentration about 200 mM, a pH about 6.2 an osmolality about 383 mOsmol/kg, and lacks lactose. In some embodiments, a formulation consists essentially of a levofloxacin concentration about 100 mg/ml, a magnesium chloride concentration about 200 mM, a pH about 6.2 an osmolality about 383 mOsmol/kg, and lacks lactose. In some embodiments, a formulation consists of a levofloxacin concentration about 100 mg/ml, a magnesium chloride concentration about 200 mM, a pH about 6.2 an osmolality about 383 mOsmol/kg, and lacks lactose.

In some embodiments, the aerosol fluoroquinolone therapy may be administered as a treatment or prophylaxis in combination or alternating therapeutic sequence with other aerosol, oral or parenteral antibiotics. By non-limiting example this may include tobramycin and/or other aminoglycoside, aztreonam, carumonam and tigemonam and/or other beta or mono-bactam, ciprofloxacin and/or other fluoroquinolones, azithromycin and/or other macrolides or ketolides, tetracycline and/or other tetracyclines, quinupristin and/or other streptogramins, linezolid and/or other oxazolidinones, vancomycin and/or other glycopeptides, and chloramphenicol and/or other phenicols, and colisitin and/or other polymyxins. In more embodiments, the antibiotic can include quinolones, tetracyclines, glycopeptides, aminoglycosides, β-lactams, rifamycins, macrolides/ketolides, oxazolidinones, coumermycins, chloramphenicol, streptogramins, trimethoprim, sulfamethoxazole, or polymyxins. In particular embodiments, an antibiotic of the above classes can be, for example, one of the following. In some embodiments, any of the foregoing antibiotics can be administered by any acceptable method or route, for example, by aerosol, orally or parenterally.

Beta-Lactam Antibiotics

Beta-lactam antibiotics include, but are not limited to, imipenem, meropenem, biapenem, cefaclor, cefadroxil, cefamandole, cefatrizine, cefazedone, cefazolin, cefixime, cefmenoxime, cefodizime, cefonicid, cefoperazone, ceforanide, cefotaxime, cefotiam, cefpimizole, cefpiramide, cefpodoxime, cefsulodin, ceftazidime, cefteram, ceftezole, ceftibuten, ceftizoxime, ceftriaxone, cefuroxime, cefuzonam, cephaacetrile, cephalexin, cephaloglycin, cephaloridine, cephalothin, cephapirin, cephradine, cefmetazole, cefoxitin, cefotetan, azthreonam, carumonam, flomoxef, moxalactam, amidinocillin, amoxicillin, ampicillin, azlocillin, carbenicillin, benzylpenicillin, carfecillin, cloxacillin, dicloxacillin, methicillin, mezlocillin, nafcillin, oxacillin, penicillin G, piperacillin, sulbenicillin, temocillin, ticarcillin, cefditoren, SC004, KY-020, cefdinir, ceftibuten, FK-312, S-1090, CP-0467, BK-218, FK-037, DQ-2556, FK-518, cefozopran, ME1228, KP-736, CP-6232, Ro 09-1227, OPC-20000, and LY206763.

Macrolides

Macrolides include, but are not limited to, azithromycin, clarithromycin, erythromycin, oleandomycin, rokitamycin, rosaramicin, roxithromycin, and troleandomycin.

Ketolides

Ketolides include, but are not limited to, telithromycin and cethrimycin.

Quinolones

Quinolones include, but are not limited to, amifloxacin, cinoxacin, ciprofloxacin, enoxacin, fleroxacin, flumequine, lomefloxacin, nalidixic acid, norfloxacin, ofloxacin, levofloxacin, oxolinic acid, pefloxacin, rosoxacin, temafloxacin, tosufloxacin, sparfloxacin, clinafloxacin, moxifloxacin; gemifloxacin; garenofloxacin; PD131628, PD138312, PD140248, Q-35, AM-1155, NM394, T-3761, rufloxacin, OPC-17116, DU-6859a (see, e.g., Sato, K. et al., 1992, Antimicrob Agents Chemother. 37:1491-98), and DV-7751a (see, e.g., Tanaka, M. et al., 1992, Antimicrob. Agents Chemother. 37:2212-18).

Tetracyclines, Glycylcyclines and Oxazolidinones

Tetracyclines, glycylcyclines, and oxazolidinones include, but are not limited to, chlortetracycline, demeclocycline, doxycycline, lymecycline, methacycline, minocycline, oxytetracycline, tetracycline, tigecycline, linezolide, and eperozolid.

Aminoglycosides

Aminoglycosides include, but are not limited to amikacin, arbekacin, butirosin, dibekacin, fortimicins, gentamicin, kanamycin, meomycin, netilmicin, ribostamycin, sisomicin, spectinomycin, streptomycin, and tobramycin.

Lincosamides

Lincosamides include, but are not limited to, clindamycin and lincomycin.

Streptogramins

Streptogramins include, but are not limited to quinupristin.

Glycopeptides

Glycopeptides include, but are not limited to vancomycin.

Polymyxins

Polymyxins include but are not limited to colisitin.

More examples include fosfomycin, penicillins, cephalosporins, carbapenems, penems, and carbacephems.

In some embodiments, a formulation can include a fluoroquinolone in combination with an additional active agent. As discussed herein, some such additional active agents can include antibiotics. More additional active agents can include bronchodilators, anticholinergics, glucocorticoids, eicosanoid inhibitors, and combinations thereof. Examples of bronchodilators include salbutamol, levosalbuterol, terbutaline, fenoterol, terbutlaine, pirbuterol, procaterol, bitolterol, rimiterol, carbuterol, tulobuterol, reproterol, salmeterol, formoterol, arformoterol, bambuterol, clenbuterol, indacterol, theophylline, roflumilast, cilomilast. Examples of anticholinergics include pratropium, and tiotropium. Examples of glucocorticoids include prednisone, fluticasone, budesonide, mometasone, ciclesonide, and beclomethasone. Examples of eicosanoids include montelukast, pranlukast, zafirlukast, zileuton, ramatroban, and seratrodast. More additional active agents can include pulmozyme, hypertonic saline, agents that restore chloride channel function in CF, inhaled beta-agonists, inhaled antimuscarinic agents, inhaled corticosteroids, and inhaled phosphodiesterase inhibitors. In some embodiments, the aerosol antibiotic therapy administered as a treatment or prophylaxis may be used in combination or alternating therapeutic sequence with an additional active agent. In more embodiments, the additional active agent may be administered as a treatment, alone, co-formulated, or administered with the aerosol antibiotic therapy.

Administration

The fluoroquinolone antimicrobials formulated with divalent or trivalent cations may be administered at a therapeutically effective dosage, e.g., a dosage sufficient to achieve the outcomes described herein. Similarly, the manner and schedule of administration may be selected to achieve the outcomes described herein. For example, in some embodiments, the respirable dose administered to the lungs can be from about 20 mg to about 170 mg, from about 30 mg to about 160 mg, from about 40 mg to about 150 mg, from about 50 mg to about 140 mg, and from about 65 mg to about 130 mg. In some embodiments, the loaded dose can be from about 80 mg to about 280 mg from about 90 mg to about 270 mg from about 100 mg to about 260 mg from about 110 mg to about 250 mg, and from about 120 mg to about 240 mg. In particular embodiments a dose can be administered daily, or twice daily. In some embodiments, therapy is administered for at least 28 days.

Administration of the fluoroquinolone antimicrobial agents disclosed herein or the pharmaceutically acceptable salts thereof can be via any of the accepted modes of administration for agents that serve similar utilities including, but not limited to, aerosol inhalation. Methods, devices and compositions for delivery are described in U.S. Patent Application Publication No. 2006-0276483, incorporated by reference in its entirety.

Pharmaceutically acceptable compositions include solid, semi-solid, liquid and aerosol dosage forms, such as, for example, powders, liquids, suspensions, complexations, liposomes, particulates, or the like. Preferably, the compositions are provided in unit dosage forms suitable for single administration of a precise dose.

The fluoroquinolone antimicrobial agent can be administered either alone or in some alternatives, in combination with a conventional pharmaceutical carrier, excipient or the like (e.g., mannitol, lactose, starch, magnesium stearate, sodium saccharine, talcum, cellulose, sodium crosscarmellose, glucose, gelatin, sucrose, magnesium carbonate, and the like). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate, and the like). Generally, depending on the intended mode of administration, the pharmaceutical formulation will contain about 0.005% to 95%, preferably about 0.5% to 50% by weight of a compound of the invention. Actual methods of preparing such dosage forms are known, or will be apparent, to those skilled in this art; for example, see Remington's Pharmaceutical Sciences, Mack Publishing Company, Easton, Pa.

In one preferred embodiment, the compositions will take the form of a unit dosage form such as vial containing a liquid, solid to be suspended, dry powder, lyophilate, or other composition and thus the composition may contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like.

Liquid pharmaceutically administrable compositions can, for example, be prepared by dissolving, dispersing, etc. an active compound as defined above and optional pharmaceutical adjuvants in a carrier (e.g., water, saline, aqueous dextrose, glycerol, glycols, ethanol or the like) to form a solution or suspension. Solutions to be aerosolized can be prepared in conventional forms, either as liquid solutions or suspensions, as emulsions, or in solid forms suitable for dissolution or suspension in liquid prior to aerosol production and inhalation. The percentage of active compound contained in such aerosol compositions is highly dependent on the specific nature thereof, as well as the activity of the compound and the needs of the subject. However, percentages of active ingredient of 0.01% to 90% in solution are employable, and will be higher if the composition is a solid, which will be subsequently diluted to the above percentages. In some embodiments, the composition will comprise 1.0%-50.0 of the active agent in solution.

In some embodiments of the methods, compositions, and uses provided herein, the duration of a therapy, e.g., an aerosolized antibiotic therapy can include at least about 1 day/month, at least about 2 days/month, at least about 3 days/month, at least about 4 days/month, at least about 5 days/month, at least about 6 days/month, at least about 7 days/month, at least about 8 days/month, at least about 9 days/month, at least about 10 days/month, at least about 11 days/month, at least about 12 days/month, at least about 13 days/month, at least about 14 days/month, at least about 15 days/month, at least about 16 days/month, at least about 17 days/month, at least about 18 days/month, at least about 19 days/month, at least about 20 days/month, at least about 21 days/month, at least about 22 days/month, at least about 23 days/month, at least about 24 days/month, at least about 25 days/month, at least about 26 days/month, at least about 27 days/month, at least about 28 days/month, at least about 29 days/month, at least about 30 days/month, and at least about 31 days/month.

Compositions described herein can be administered with a frequency of about 1, 2, 3, 4, or more times daily, 1, 2, 3, 4, 5, 6, 7 or more times weekly, 1, 2, 3, 4, 5, 6, 7, 8, 9, 10 or more times monthly. In particular embodiments, the compositions are administered twice daily.

Aerosol Delivery

For pulmonary administration, the upper airways are avoided in favor of the middle and lower airways. Pulmonary drug delivery may be accomplished by inhalation of an aerosol through the mouth and throat. Particles having a mass median aerodynamic diameter (MMAD) of greater than about 5 microns generally do not reach the lung; instead, they tend to impact the back of the throat and are swallowed and possibly orally absorbed. Particles having diameters of about 2 to about 5 microns are small enough to reach the upper- to mid-pulmonary region (conducting airways), but are too large to reach the alveoli. Smaller particles, i.e., about 0.5 to about 2 microns, are capable of reaching the alveolar region. Particles having diameters smaller than about 0.5 microns can also be deposited in the alveolar region by sedimentation, although very small particles may be exhaled.

In one embodiment, a nebulizer is selected on the basis of allowing the formation of an aerosol of a fluoroquinolone antimicrobial agent disclosed herein having an MMAD predominantly between about 2 to about 5 microns. In one embodiment, the delivered amount of fluoroquinolone antimicrobial agent provides a therapeutic effect for respiratory infections. The nebulizer can deliver an aerosol comprising a mass median aerodynamic diameter from about 2 microns to about 5 microns with a geometric standard deviation less than or equal to about 2.5 microns, a mass median aerodynamic diameter from about 2.5 microns to about 4.5 microns with a geometric standard deviation less than or equal to about 1.8 microns, and a mass median aerodynamic diameter from about 2.8 microns to about 4.3 microns with a geometric standard deviation less than or equal to about 2 microns. In some embodiments, the aerosol can be produced using a vibrating mesh nebulizer. An example of a vibrating mesh nebulizer includes the PART E-FLOW® nebulizer. More examples of nebulizers are provided in U.S. Pat. Nos. 4,268,460; 4,253,468; 046,146; 3,826,255; 4,649,911; 4,510,929; 4,624,251; 5,164,740; 5,586,550; 5,758,637; 6,644,304; 6,338,443; 5,906,202; 5,934,272; 5,960,792; 5,971,951; 6,070,575; 6,192,876; 6,230,706; 6,349,719; 6,367,470; 6,543,442; 6,584,971; 6,601,581; 4,263,907; 5,709,202; 5,823,179; 6,192,876; 6,644,304; 5,549,102; 6,083,922; 6,161,536; 6,264,922; 6,557,549; and 6,612,303 all of which are hereby incorporated by reference in their entireties. More commercial examples of nebulizers that can be used with the formulations described herein include Respirgard II®, Aeroneb®, Aeroneb® Pro, and Aeroneb® Go produced by Aerogen; AERx® and AERx® Essence™ produced by Aradigm; Porta-Neb®, Freeway Freedom™, Sidestream Ventstream and I-neb produced by Respironics, Inc.; and PARI LC-Plus®, PARI LC-Star®, produced by PART, GmbH. By further non-limiting example, U.S. Pat. No. 6,196,219, is hereby incorporated by reference in its entirety.

The amount of levofloxacin or ofloxacin that can be administered (as a respirable dose, nebulizer loaded dose, and/or deposited dose) can include at least about 20 mg, about 30 mg, about 40 mg, about 50 mg, about 60 mg, about 70 mg, about 80 mg, about 90 mg, about 100 mg, about 110 mg, about 120 mg, about 125 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, about 710 mg, about 720 mg, about 730 mg, about 740 mg, about 750 mg, about 760 mg, about 770 mg, about 780 mg, about 790 mg, and about 800 mg.

The aerosol can be administered to the lungs in less than about 10 minutes, about 5 minutes, about 4 minutes, about 3 minutes, about 2 minutes, and about 1 minute.

Indications

Methods and compositions described herein can be used to treat pulmonary infections and disorders, for example, cystic fibrosis. Some embodiments include treating an infection comprising one or more bacteria that can include *Pseudomonas aeruginosa, Pseudomonas fluorescens, Pseudomonas acidovorans, Pseudomonas alcaligenes, Pseudomonas putida, Stenotrophomonas* sp., e.g., *Stenotrophomonas maltophilia, Aeromonas hydrophilia, Escherichia coli, Citrobacter freundii, Salmonella typhimurium, Salmo-* nella typhi, Salmonella paratyphi, Salmonella enteritidis. Shigella dysenteriae. Shigella flexneri, Shigella sonnei, Enterobacter cloacae, Enterobacter aerogenes, Klebsiella pneumoniae, Klebsiella oxytoca, Serratia marcescens, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi. Pasteurella multocida, Pasteurella haemolytica, Helicobacter pylori, Campylobacter fetus, Campylobacter jejuni, Campylobacter coli, Borrelia burgdorferi, Vibrio cholera, Vibrio parahaemolyticus, Legionella pneumophila, Listeria monocytogenes, Neisseria gonorrhoeae, Neisseria meningitidis, Burkholderia sp., e.g., Burkholderia cepacia, Francisella tularensis, Kingella, and Moraxella. In some embodiments, the pulmonary infection can include a gram-negative anaerobic bacteria. In more embodiments, the pulmonary infection can include one or more of the bacteria selected from the group consisting of Bacteroides fragilis, Bacteroides distasonis, Bacteroides 3452A homology group, Bacteroides vulgatus, Bacteroides ovalus, Bacteroides thetaiotaomicron, Bacteroides uniformis, Bacteroides eggerthii, and Bacteroides splanchnicus. In some embodiments, the pulmonary infection can include a gram-positive bacteria. In some embodiments, the pulmonary infection can include one or more of the bacteria selected from the group consisting of Corynebacterium diphtheriae, Corynebacterium ulcerans, Streptococcus pneumoniae, Streptococcus agalactiae, Streptococcus pyogenes, Streptococcus milleri; Streptococcus (Group G); Streptococcus (Group C/F); Enterococcus faecalis, Enterococcus faecium, Staphylococcus aureus, Staphylococcus epidermidis, Staphylococcus saprophyticus, Staphylococcus intermedius. Staphylococcus hyicus subsp. hyicus, Staphylococcus haemolyticus, Staphylococcus hominis, and Staphylococcus saccharolyticus. In some embodiments, the pulmonary infection can include a gram-positive anaerobic bacteria. In some embodiments, the pulmonary infection can include one or more bacteria selected from the group consisting of Clostridium difficile, Clostridium perfringens, Clostridium tetini, and Clostridium botulinum. In some embodiments, the pulmonary infection can include an acid-fast bacteria. In some embodiments, the pulmonary infection can include one or more bacteria selected from the group consisting of Mycobacterium tuberculosis, Mycobacterium avium, Mycobacterium intracellulare, and Mycobacterium leprae. In some embodiments, the pulmonary infection can include an atypical bacteria. In some embodiments, the pulmonary infection can include one or more bacteria selected from the group consisting of Chlamydia pneumoniae and Mycoplasma pneumoniae. In some embodiments, the pulmonary infection can comprise a non-fermenting gram-negative bacteria (NFGNB). Examples of NFGNB can include Burkholeria spp., stenotrophomonas spp., acinetobacter spp., pseudomonas spp., and Achromobacter spp. More example of bacteria useful in the methods and compositions provided herein can be found in 'Bergey's Manual of Systematic Bacteriology,' Editor-in-chief: Garrity, George M. Boone, David R.; Castenholz, Richard W. (Eds.) Originally published by Williams & Wilkins, 1984, 2nd ed., (2001), incorporated by reference in its entirety.

Some methods and compositions provided here can be especially appropriate for the treatment of pulmonary infections and disorders that include microbial strains that can be difficult to treat using an antimicrobial agent delivered parenterally due to the need for high parenteral dose levels, which can cause undesirable side effects, or due to lack of any clinically effective antimicrobial agents. For example, administration of an aerosol fluoroquinolone antimicrobial directly to the site of infection may reduce systemic exposure and can maximize the amount of antimicrobial agent to the site of microbial infection. Such methods can be appropriate for treating infections involving microbes that are susceptible to fluoroquinolone antimicrobials as a way of reducing the frequency of selection of resistant microbes.

In some embodiments, the aerosol fluoroquinolone antimicrobial agent formulated with divalent or trivalent cations is administered at a level sufficient to overcome the emergence resistance in bacteria or increase killing efficiency such that resistance does not have the opportunity to develop.

Some embodiments of the methods and compositions described herein include achieving a reduction in a pulmonary infection. A reduction in a pulmonary infection can be measured using a variety of different methods. For example, in a pulmonary infection comprising one or more organisms, a reduction in the density of the organism can be measured. In some embodiments, treatment can achieve a reduction in the density of an organism by at least about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 100%. In some embodiments, treatment can achieve a reduction in the density of an organism by at least about 85%, about 86%, about 87%, about 88%, about 89%, about 90%, about 91%, about 92%, about 93%, about 94%, about 95%, about 96%, about 97%, about 98%, about 99%, and about 100%.

The density of an organism can be measured in a sample taken from a subject, for example, bronchial alveolar lavage, sputum, and serum. In some embodiments the density of an organism can be reduced by at least about 0.1, about 0.2, about 0.3, about 0.4, about 0.5, about 0.6, about 0.7, about 0.8, about 0.8, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5 $\log_{10}$ CFU/g sputum, or more.

Some embodiments of the methods and compositions described herein can include achieving an improvement in a pulmonary function parameter. Examples of such parameters can include FEV (forced expiratory volume), $FEV_1$ (forced expiratory volume in 1 second), and FEF 25-75 (forced expiratory flow 25-75%). In some embodiments, the $FEV_1$ of a subject can be increased using the methods and compositions described herein, by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, and more. In some embodiments, the FEVI of a subject can be increased using the methods and compositions described herein, by at least about 0.01 L, 0.02 L, 0.03 L, 0.04 L, and 0.05 L, and by at least about 0.1 L, 0.2 L, 0.3 L, 0.4 L, 0.5 L, 0.6 L, 0.7 L, 0.8 L, 0.9 L, 1.0 L, and more.

In some embodiments, the FEF 25-75 of a subject can be increased using the methods and compositions described herein, by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, and 25%. In some embodiments, the FEF 25-75 of a subject can be increased using the methods and compositions described herein, by at least about 0.01 L, 0.02 L, 0.03 L, 0.04 L, and 0.05 L, and by at least about 0.1 L, 0.2 L, 0.3 L, 0.4 L, 0.5 L, 0.6 L, 0.7 L, 0.8 L, 0.9 L, 1.0 L, and more.

Some embodiments of the methods and compositions described herein can include reducing the need for a subject to need other inhaled or systemic antibiotics, such as antipseudomonal antimicrobials. Such a reduction can be measured by a variety of methods, for example, by the increase in time to need other inhaled or systemic antibiotics. A reduction in such a need can be measured by a variety of statistical means. For example, hazard ratios may be used in a survival analysis. In some embodiments, the hazard ratio is less than about 1.0, 0.9, 0.8, 0.7, 0.6, 0.5, 0.4, 0.3, 0.2, 0.1, and less.

Some embodiments of the methods and compositions described herein can include decreasing the frequency of exacerbations, the severity of exacerbations, the duration of exacerbations, or the likelihood that an exacerbation will occur. An exacerbation can be defined by any of several methods and criteria provided by such methods. In some embodiments, a patient can concurrently meet at least 4 symptoms/signs of the Fuchs definition of an exacerbation (Fuchs H J, et al. Effect of aerosolized recombinant human DNase on exacerbations of respiratory symptoms and on pulmonary function in patients with cystic fibrosis. N Engl J Med 1994; 331:637-642, incorporated by reference in its entirety). The symptoms/signs defined by the Fuchs criteria include: change in sputum; new or increased hemoptysis; increased cough; increased dyspnea; malaise, fatigue or lethargy; temperature above 38° C.; anorexia or weight loss; sinus pain or tenderness; change in sinus discharge; change in physical examination of the chest; decrease in pulmonary function by 10% or more from a previously recorded value; and radiographic changes indicative of pulmonary infection.

In some embodiments, a patient with an improved exacerbation profile can have at least 1, at least 2, at least 3, and at least 4 of the following signs/symptoms, where changes can be relative to a patient's typical experience, for example daily experience, and weekly experience. (1) Change in sputum, e.g., for sputum production: patients have no change, a little less or much less amounts of sputum when coughing up, or for change in sputum appearance: for sputum thickness, patients have a little thinner or much thinner sputum; for sputum color, patients have a better color of sputum (better increases from brown→green→yellow→clear). (2) Hemoptysis, e.g., patients have a little decrease or a large decrease in the amount of blood coughed up. (3) Cough, e.g., for intensity of cough, patients have a little lighter, or much lighter coughs; for frequency of cough, patients cough a little less often or much less often. (4) Dyspnea, e.g., for dyspnea with exertion, patients breathe a little easier or much easier when performing daily activities. (5) Malaise, fatigue or lethargy, e.g., patients have a little more energy or much more energy, and/or patients perform daily activities, e.g., climbing stairs, a little easier, or much easier. (6) Temperature, e.g., patients have normal healthy temperature e.g., about 37° C., or patients have no recent history of fever. (7) Anorexia or weight loss, e.g., patients have no change in weight, or a little weight gain, and/or patients have a little increase in appetite (8) Sinus pain or tenderness, e.g., patient has no sinus pain or tenderness, or less sinus pain or tenderness. (9) Change in sinus discharge, e.g., patients have better sinus discharge (a decrease in thickness and/or better color). (10) Change in physical examination of the chest, e.g., patients have improved signs on examination of the chest and may report for example, a little decrease chest congestion, or a large decrease in chest congestion. (11) Pulmonary function by 10% or more from a previously recorded value, e.g., patients have improved pulmonary function in pulmonary function tests. (12) Radiographic changes indicative of pulmonary infection, e.g. patients show improved radiographic changes indicating reduced pulmonary infection.

In some embodiments, exercise tolerance and/or absenteeism from scheduled events, e.g., school or work can be measured as signs/symptoms of exacerbations.

Table 1 summarizes a variety of methods useful to measure exacerbations.

TABLE 1

| Sign/Symptom | Method/Protocol | | | | | | |
|---|---|---|---|---|---|---|---|
| | Fuchs | Ramsey | CFF | Rosenfeld (Seattle)[A] | Kraynack[B] | Rabin | Blummer |
| Cough | X | X | X | X | X | X | X |
| Sputum | X | X | X | X | X | X | X |
| Hemoptysis | X | | | | X | X | |
| Dyspnea | X | | | | X | | X |
| Exercise Tolerance | | | X | X | X | | X |
| Absenteeism | | X | X | X | | X | |
| Fatigue | X | | | | X | | X |
| Fever | X | X | X | | X | | |
| Decreased/Loss Appetite | X | X | X | X | X | X | |
| Sinus pain | X | X | | | | | |
| Sinus discharge | X | | | | | | |
| Chest exam | X | | X | X | X | | X |
| Tachypnea | | X | X | | | | X |
| Lung function | X | X | X | (X) | X | X | X |
| CXR | X | | X | | X | | X |
| SaO2 | | | X | | X | | |
| Neutrophila | | X | | | | | |
| Criteria | 4/12 plus antibiotics | 2/3 plus 1/3 | 3/11 | Score | Score | 3/4 | 3/4 |

[A]Rosenfeld M. et al., Defining a pulmonary exacerbation in cystic fibrosis. J. of Pediatrics 139:359-365 (2001), incorporated by reference in its entirety.
[B]Kraynack N. C. et al., Improving care at cystic fibrosis centers through quality improvement. Semin Respir Crit Care Med. 2009 October; 30(5):547-58), incorporated by reference in its entirety.

Some embodiments of any of the above methods include administering levofloxacin or ofloxacin in combination with a divalent or trivalent cation in a dosage amount, administration schedule, and/or method of administration sufficient to achieve the above recited outcomes.

Pediatric Patient Populations

Some embodiments provided herein relate to the use of the compositions provided herein to treating cystic fibrosis in a human. In some embodiments, the human is a pediatric patient. In some embodiments, the human has an age less than about 18 years, less than about 17 years, less than about 16 years, less than about 15 years, less than about 14 years, less than about 13 years, less than about 12 years, less than about 11 years, less than about 10 years, less than about 9 years, less than about 8 years, less than about 7 years, less than about 6 years, less than about 5 years, less than about 4 years, less than about 3 years, less than about 2 years, and less than about 1 year.

Dosages of aerosol therapeutic agents for pediatric subjects can be less than the dosage for an adult subject. In some embodiments, dosage can be determined, in part, due to the weight of a subject. For example, a subject having a weight from about 14 kg to about 21 kg can receive a dose of about 120 mg, a subject having a weight from about 22 kg to about 30 kg can receive a dose of about 180 mg dose, and a subject having a weight more than about 30 kg can receive a dose of about 240 mg. In some embodiments, the aerosol therapeutic agent can be administered daily, or twice daily. In some embodiments, the aerosol therapeutic agent can be administered for a period of at least about 1 day, 3 days, 5 days, 10 days, 15 days, 20 days, and 30 days. In some embodiments, the aerosol therapeutic agent can be administered for about 14 days. In particular embodiments the aerosol therapeutic agent is administered daily for 14 days.

In some embodiments, the human has a body weight less than about 70 kg, less than about 60 kg, less than about 50 kg, less than about 40 kg, less than about 30 kg, less than about 20 kg, and less than about 10 kg.

In some embodiments, the human has a body surface area less than about 1.8 m$^2$, less than about 1.6 m$^2$, less than about 1.4 m$^2$, less than about 1.2 m$^2$, less than about 1.0 m$^2$, less than about 0.8 m$^2$, less than about 0.6 m$^2$, and less than about 0.4 m$^2$.

In some embodiments, treating one of the above humans comprises achieving a dose-normalized serum AUC at least about 5 (ng·h/L)/mg Dose, at least about 10 (ng·h/L)/mg Dose, at least about 20 (ng·h/L)/mg Dose, at least about 40 (ng·h/L)/mg Dose, at least about 60 (ng·h/L)/mg Dose, at least about 80 (ng·h/L)/mg Dose, and at least about 100 (ng·h/L)/mg Dose.

In some embodiments, treating one of the above humans comprises achieving a dose-normalized serum $C_{max}$ greater than about 1 µg/L/mg administered dose, greater than about 2 µg/L/mg administered dose, greater than about 3 µg/L/mg administered dose, greater than about 4 µg/L/mg administered dose, greater than about 5 µg/L/mg administered dose, greater than about 6 µg/L/mg administered dose, greater than about 7 µg/L/mg administered dose, greater than about 8 µg/L/mg administered dose, greater than about 9 µg/L/mg administered dose, greater than about 10 µg/L/mg administered dose, greater than about 11 µg/L/mg administered dose, greater than about 12 µg/L/mg administered dose, greater than about 13 µg/L/mg administered dose, greater than about 14 µg/L/mg administered dose, greater than about 15 µg/L/mg administered dose, and greater than about 16 µg/L/mg administered dose.

Some embodiments of any of the above methods for treating the recited humans include administering levofloxacin or ofloxacin in combination with a divalent or trivalent cation in a dosage amount, administration schedule, and/or method of administration sufficient to achieve the recited outcomes.

EXAMPLES

Example 1—Phase 1b Clinical Study with Levofloxacin

A Phase 1 b single-blind, placebo-control, dose-escalating multicenter study was carried out to evaluate the safety, tolerability, and pharmacokinetic (PK) profile of aerosolized levofloxacin administered to stable CF patients. All patients had had *P. aeruginosa* cultured from sputum within the previous 24 months and at the screening visit. Study drug was administered twice daily for up to 14 days at three doses by aerosol using a PART eFlow device. Respirable delivered doses (RDD) were approximately 40 mg, 80 mg, and 120 mg per treatment, corresponding to loaded doses of 78 mg, 175 mg, and 260 mg, respectively. Thus, the estimated total daily RDDs were 80 mg, 160 mg, and 240 mg. Study drugs were administered at 30 mg/ml (for 40 mg dose) or 50 mg/ml (for 80 mg and 120 mg doses). Table 2 shows the formulations of the study drugs.

TABLE 2

|  | 30 mg/ml Levofloxacin solution | 50 mg/ml Levofloxacin solution | Placebo |
|---|---|---|---|
| Levofloxacin, mg/ml mM) | 30 (81.6) | 50 (136) | 0 |
| Magnesium, mg/ml (mM) | 1.5 (60) | 2.4 (100) | 2.4 (100) |
| Chloride, mg/ml (mM) | 4.3 (120) | 7.1 (200) | 7.1 (200) |
| Lactose, mg/ml (mM) | 51.4 (150) | 51.4 (150) | 51.4 (150) |
| pH | 6.3 | 6.3 | 6.5 |
| Osmolality, mOsm/kg | 314 | 400 | 424 |

All patients used at least 1 concomitant medication during the study. Concomitant medications are those medications taken after the first dose of Study Drug regardless of medication start date. Concomitant medications used by at least 20% of patients included Salbutamol, Dornase alfa, Azithromycin, Seretide, Pancrelipase, Adeks, Hypertonic solutions, and Nortase.

Efficacy Results

Table 3 summarizes the results for pulmonary function tests for $FEV_1$ measurements. The greatest relative improvement in $FEV_1$ after 7 and 14 days of dosing was observed in the 120 mg RDD (260 mg loaded) levofloxacin cohort, with a mean improvement of 14.79% and 17.58%, respectively. A mean improvement of 8.90% persisted over the 2 weeks to the follow-up visit. In addition, there appeared to be a dose response in patients receiving levofloxacin with patients in the 80 mg and 120 mg dose groups having an improvement in the $FEV_1$, while those in the 40-mg dose group did not. All 9 patients in the 120 mg dose group had a relative increase in $FEV_1$, with 4 of 9 patients having at least a 20% increase.

TABLE 3

Median FEVi change (%) for each Treatment Group

| Time point | Placebo | 40 mg RDD Levofloxacin | 80 mg RDD Levofloxacin | 120 mg. RDD Levofloxacin |
|---|---|---|---|---|
| Day 7 | n = 10 | n = 10 | n = 10 | n = 9 |
|  | 5.75 | −0.75 | 6.15 | 10.20 |
| Day 14 | n = 8 | n = 10 | n = 10 | n = 9 |
|  | 1.20 | −1.55 | 2.95 | 16.90 |

Table 4 show the relative changes from baseline across visits (Day 1, 2, 7, 14, and 21) in pulmonary function tests for $FEV_1$. In Table 3, relative change from baseline (CBG) was calculated as 'Result' $FEV_1$ minus 'Baseline' $FEV_1$ divided by 'Baseline' $FEV_1$.

TABLE 4

$FEV_1$ (L) for each Treatment Group

| Time point | Placebo N = 10 | 40 mg RDD Levofloxacin N = 10 | 80 mg RDD Levofloxacin N = 10 | 120 mg. RDD Levofloxacin N = 10 |
|---|---|---|---|---|
| Day 1 Predose Baseline |  |  |  |  |
| n | 10 | 10 | 10 | 10 |
| Mean (SD) | 2.62 (1.150) | 2.26 (0.534) | 2.06 (0.649) | 2.56 (1.121) |
| Median | 2.46 | 2.30 | 1.95 | 2.23 |
| Minimum, maximum | 1.31, 4.90 | 1.58, 3.50 | 1.17, 3.19 | 1.43, 4.71 |
| Day 2 Predose Result |  |  |  |  |
| n | 10 | 10 | 10 | 10 |
| Mean (SD) | 2.75 (1.310) | 2.31 (0.594) | 2.10 (0.709) | 2.73 (1.132) |
| Median | 2.43 | 2.32 | 2.00 | 2.38 |
| Minimum, maximum | 1.33, 5.50 | 1.57, 3.60 | 1.13, 3.46 | 1.40, 4.72 |
| Day 2 Relative CFB (%) |  |  |  |  |
| n | 10 | 10 | 10 | 10 |
| Mean (SD) | 3.85 (6.627) | 1.92 (8.315) | 1.57 (5.149) | 7.29 (10.081) |
| Median | 2.00 | −0.30 | 1.90 | 6.60 |
| Minimum, maximum | −7.10, 12.20 | −6.30, 21.70 | −7.60, 8.90 | −4.70, 23.90 |
| Day 7 Result |  |  |  |  |
| n | 10 | 10 | 10 | 9 |
| Mean (SD) | 2.82 (1.361) | 2.30 (0.544) | 2.26 (0.831) | 3.07 (1.220) |
| Median | 2.35 | 2.30 | 2.08 | 2.40 |
| Minimum, maximum | 1.39, 5.20 | 1.49, 3.48 | 1.20, 3.79 | 1.79, 4.99 |
| Day 7 Relative CFB (%) |  |  |  |  |
| n | 10 | 10 | 10 | 9 |
| Mean (SD) | 5.86 (10.196) | 1.60 (6.985) | 9.42 (18.911) | 14.79 (12.865) |
| Median | 5.75 | −0.75 | 6.15 | 10.20 |
| Minimum, maximum | −6.50, 29.40 | −5.70, 17.90 | −7.40, 59.90 | 3.40, 37.70 |
| Day 14 Predose Result |  |  |  |  |
| n | 8 | 10 | 10 | 9 |
| Mean (SD) | 2.99 (1.272) | 2.26 (0.524) | 2.09 (0.616) | 3.12 (1.173) |
| Median | 3.11 | 2.30 | 2.10 | 2.57 |
| Minimum, maximum | 1.47, 5.20 | 1.55, 3.38 | 1.19, 3.21 | 1.74, 4.78 |
| Day 14 Relative CFB (%) |  |  |  |  |
| n | 8 | 10 | 10 | 9 |
| Mean (SD) | 2.00 (5.529) | 0.21 (8.440) | 2.69 (10.125) | 17.58 (15.089) |
| Median | 1.20 | −1.55 | 2.95 | 16.90 |
| Minimum, maximum | −6.70, 8.80 | −8.70, 23.10 | −19.40, 19.10 | 1.50, 41.50 |
| Day 21/ET Result |  |  |  |  |
| n | 10 | 10 | 10 | 10 |
| Mean (SD) | 2.75 (1.327) | 2.16 (0.517) | 2.03 (0.632) | 2.75 (1.155) |
| Median | 2.28 | 2.07 | 2.04 | 2.48 |
| Minimum, maximum | 1.17, 5.10 | 1.46, 3.42 | 1.06, 2.82 | 1.49, 4.87 |

TABLE 4-continued

<table>
<tr><td rowspan="2">Time point</td><td colspan="4">FEV₁ (L) for each Treatment Group</td></tr>
<tr><td>Placebo<br>N = 10</td><td>40 mg RDD<br>Levofloxacin<br>N = 10</td><td>80 mg RDD<br>Levofloxacin<br>N = 10</td><td>120 mg. RDD<br>Levofloxacin<br>N = 10</td></tr>
<tr><td colspan="5">Day 21/ET Relative CFB (%)</td></tr>
<tr><td>n</td><td>10</td><td>10</td><td>10</td><td>10</td></tr>
<tr><td>Mean (SD)</td><td>3.20 (10.157)</td><td>−4.25 (7.092)</td><td>−1.03 (8.880)</td><td>8.90 (15.789)</td></tr>
<tr><td>Median</td><td>1.75</td><td>−5.80</td><td>−3.10</td><td>10.10</td></tr>
<tr><td>Minimum, maximum</td><td>−10.70, 20.60</td><td>−12.70, 11.80</td><td>−11.60, 12.90</td><td>−15.90, 38.70</td></tr>
</table>

ET = early termination.

Colony-forming units of *P. aeruginosa* at Day 1 were compared with colony-forming units at Day 7 and 14. Table 5 summarizes the percentage change in sputum *P. aeruginosa* (log CFU/g) in treatment groups. Declines in sputum *P. aeruginosa* were observed over all days of dosing.

TABLE 5

<table>
<tr><td rowspan="2">Time<br>point</td><td colspan="2">Median Change in sputum *P. aeruginosa* (log CFU/g) for Treatment Group</td></tr>
<tr><td>Placebo</td><td>Levofloxacin solution</td></tr>
<tr><td>Day 7</td><td>0.04 (n = 9)</td><td>−0.50 (n = 21)</td></tr>
<tr><td>Day 14</td><td>0.04 (n = 9)</td><td>−1.23 (n = 21)</td></tr>
</table>

Safety Results

No study drug-related serious adverse events were reported. Most adverse events were mild or moderate in severity and self-limiting. The majority of adverse events were mild, with taste complaints, cough and headache as the most commonly observed adverse events. No patients receiving levofloxacin solution for inhalation met drug intolerability criteria. Adverse events reported in more than 1 patient receiving levofloxacin included abdominal pain, cough, disease progression (acute exacerbation), dysgeusia (bad taste), haemoptysis, headache, nasal congestion, nasopharyngeal pain (sore throat), respiratory tract congestion, and wheezing. Table 6 summarizes adverse events observed in more than one CF patient receiving levofloxacin. Accordingly, these results demonstrated the safety and tolerability of levofloxacin with multiple doses over 14 days.

TABLE 6

<table>
<tr><td rowspan="2">Adverse event</td><td colspan="4">Treatment group</td></tr>
<tr><td>40 mg<br>Levofloxacin<br>(N = 10)</td><td>80 mg<br>Levofloxacin<br>(N = 10)</td><td>120 mg.<br>Levofloxacin<br>(N = 10)</td><td>Placebo<br>(N = 10)</td></tr>
<tr><td>Abdominal pain</td><td>1 (10%)</td><td>—</td><td>1 (10%)</td><td>—</td></tr>
<tr><td>Alopecia</td><td>—</td><td>1 (10%)</td><td>—</td><td>—</td></tr>
<tr><td>Blood blister</td><td>—</td><td>—</td><td>1 (10%)</td><td>—</td></tr>
<tr><td>Breath sounds abnormal</td><td>—</td><td>—</td><td>1 (10%)</td><td>—</td></tr>
<tr><td>Chest discomfort</td><td>—</td><td>1 (10%)</td><td>—</td><td>1 (10%)</td></tr>
<tr><td>Cough</td><td>—</td><td>4 (40%)</td><td>4 (40%)</td><td>1 (10%)</td></tr>
<tr><td>Diarrhoea</td><td>1 (10%)</td><td>—</td><td>—</td><td>—</td></tr>
<tr><td>Disease progression</td><td>—</td><td>—</td><td>2 (20%)</td><td>1 (10%)</td></tr>
<tr><td>Drooling</td><td>—</td><td>1 (10%)</td><td>—</td><td>—</td></tr>
<tr><td>Dysguesia</td><td>3 (30%)</td><td>6 (60%)</td><td>5 (50%)</td><td>1 (10%)</td></tr>
<tr><td>Dyspnoea</td><td>1 (10%)</td><td>—</td><td>—</td><td>—</td></tr>
<tr><td>Fatigue</td><td>—</td><td>1 (10%)</td><td>—</td><td>—</td></tr>
<tr><td>Flank pain</td><td>1 (10%)</td><td>—</td><td>—</td><td>—</td></tr>
<tr><td>Forced expired volume decreased</td><td>—</td><td>1 (10%)</td><td>—</td><td>1 (10%)</td></tr>
<tr><td>Hemoptysis</td><td>—</td><td>1 (10%)</td><td>1 (10%)</td><td>—</td></tr>
<tr><td>Headache</td><td>—</td><td>2 (20%)</td><td>2 (20%)</td><td>—</td></tr>
<tr><td>Migraine</td><td>—</td><td>1 (10%)</td><td>—</td><td>—</td></tr>
<tr><td>Nasal congestion</td><td>—</td><td>1 (10%)</td><td>1 (10%)</td><td>—</td></tr>
<tr><td>Non-cardiac chest pain</td><td>—</td><td>1 (10%)</td><td>—</td><td>—</td></tr>
<tr><td>Oral candidiasis</td><td>—</td><td>1 (10%)</td><td>—</td><td>—</td></tr>
<tr><td>Paraethesia oral</td><td>—</td><td>—</td><td>1 (10%)</td><td>—</td></tr>
<tr><td>Pharyngolaryngeal pain</td><td>—</td><td>—</td><td>2 (20%)</td><td>—</td></tr>
<tr><td>Pulmonary function test decreased</td><td>—</td><td>—</td><td>1 (10%)</td><td>—</td></tr>
<tr><td>Pyrexia</td><td>—</td><td>—</td><td>1 (10%)</td><td>—</td></tr>
<tr><td>Rash erythematous</td><td>—</td><td>—</td><td>1 (10%)</td><td>—</td></tr>
<tr><td>Respiratory tract congestion</td><td>—</td><td>—</td><td>2 (20%)</td><td>—</td></tr>
<tr><td>Retching</td><td>—</td><td>1 (10%)</td><td>—</td><td>—</td></tr>
<tr><td>Rhinorrhoea</td><td>—</td><td>1 (10%)</td><td>—</td><td>—</td></tr>
<tr><td>Thirst</td><td>—</td><td>1 (10%)</td><td>—</td><td>—</td></tr>
<tr><td>Upper respiratory tract infection</td><td>1 (10%)</td><td>—</td><td>—</td><td>1 (10%)</td></tr>
<tr><td>Wheezing</td><td>1 (10%)</td><td>—</td><td>1 (10%)</td><td>—</td></tr>
</table>

Example 2—Phase 2 Clinical Study with Levofloxacin

A phase 2, multi-center, randomized, double-blind, placebo-controlled study was carried out to evaluate the safety, tolerability and efficacy of three dosage regimens of levofloxacin formulated with $MgCl_2$ administered for 28 days to stable CF patients. The following dosage regimens (as nebulizer loaded doses) were evaluated: 120 mg QD (daily); 240 mg QD (daily); and 240 mg BID (twice daily). Based on aerosol characterization studies of the 100 mg/ml formulation, these loaded doses of 120 and 240 mg correspond estimated respirable delivered doses (RDDs) using a PART eFlow nebulizer of about 65 and 130 mg, respectively. The plasma levofloxacin Cm. and AUC with all dosage regimens chosen for this study should provide concentrations in pulmonary tissues well in excess of those associated with bactericidal activity against CF pathogens (data not shown).

The formulation of levofloxacin solution and placebo is shown in Table 7. Study drug was administered by aerosol using the PARI eFlow® device with a mesh to deliver a particle size smaller than approximately 3.5 μm-4.0 μm.

TABLE 7

|  | Levofloxacin | Placebo |
| --- | --- | --- |
| Levofloxacin, mg/ml (mM) | 100 (272) | 0 |
| Mg, mg/ml (mM) | 5.0 (200) | 0 |
| Cl, mg/ml (mM) | 14.4 (400) | 0 |
| pH | 5-7 | 6-8 |
| Osmolality, mOsm/kg | 350-500 | 300-500 |
| Saline | — | 0.9% |

Patient inclusion criteria included: (1) at least 16 years of age; (2) clinically diagnosed with CF; (3) able to elicit an $FEV_1 \geq 25\%$ but $\leq 85\%$ predicted value at Screening; (4) received at least 3 courses of inhaled antimicrobials over the preceding 12 months and had received at least 1 course of inhaled tobramycin/(TOB®)/colistin in the 2 months prior to Visit 1 (Day 1), but none in the 28 days prior to Visit 1 (Day 1); (5) had a sputum specimen at Screening positive for P. aeruginosa and a history of at least 1 positive sputum culture positive for P. aeruginosa within the last 18 months; and (6) clinically stable with no significant changes in health status within the last 30 days.

Patient exclusion criteria included: (1) use of an investigational agent within 30 days prior to Visit 1 (Day 1); (2) use of any nebulized or systemic antibiotics active against P. aeruginosa within 28 days prior to Visit 1 (Day 1), other than maintenance oral azithromycin, which must have been initiated at least 30 days prior to Visit 1 (Day 1); (3) hypersensitivity to fluoroquinolones or excipients of levofloxacin formulated with $MgCl_2$; (4) intolerance to bronchodilators or unwilling to use a bronchodilator during the study; (5) use of oral corticosteroids in doses exceeding the equivalent of 10 mg prednisone/day or 20 mg prednisone every other day; (6) changes in physiotherapy technique or schedule within 14 days prior to Visit 1 (Day 1); (7) changes in medical regimen for treatment of CF (e.g., introduction, dose escalation, or elimination of therapies such as dornase alfa, nonsteroidal anti-inflammatory agents, azithromycin, hypertonic saline, or inhaled corticosteroids) within 30 days of Visit 1 (Day 1); (8) history of lung transplantation; (9) evidence of acute upper respiratory tract infection within 10 days or lower respiratory tract infection within 30 days prior to Visit 1 (Day 1); (10) pregnancy, breastfeeding, or unwilling to practice birth control or abstinence during participation in the study (women only); (11) history of seizures or low seizure threshold (e.g., epilepsy); (12) renal dysfunction (calculated creatinine clearance [CrCl]<50 mL/min) at Screening; (13) aspartate aminotransferase (AST), alanine aminotransferase (ALT), or total bilirubin≥3×upper limit of normal (ULN) at Screening or evidence of severe liver disease (e.g., cirrhosis, portal hypertension); (14) history of human immunodeficiency virus (HIV), hepatitis B, or hepatitis C infection/seropositivity; (15) history of hemoptysis ≥30 mL over any 24-hour period during the 30 days prior to Visit 1; (16) oxygen saturation <90% on room air at Screening or Visit 1 (Day 1); and (17) >15% relative decline in $FEV_1(L)$ from Screening to Visit 1 (Day 1).

Patients were assessed on Day 1, 7, 14, and 28, and then up to 28 days after completion of study drug, namely, Days 42 and 56. The formulation of study drug, i.e., levofloxacin, is shown in Table 7. The end of the study was defined as the last visit of the last patient. Study populations included: (1) safety/modified intent to treat (MITT) population which included all patients enrolled in the study that receive at least one dose of study drug; (2) efficacy evaluable (EE) population which included all patients enrolled in the study without major protocol violations that receive at least 80% of study drug doses during the 28 days of study drug therapy; and (3) pharmacokinetic (PK) population which included all patients that receive at least one dose of study drug and have at least one PK blood sample collected.

Approximately 32 patients per treatment arm provided 80°% power to detect a difference between treatment arms using a 2-sided analysis of covariance (ANCOVA), with a 5% alpha, assuming a standard deviation (SD) of 1.5 and a mean log CFU change in P. aeruginosa of 0.75 decrease, 0.75 decrease, no change and 0.25 increase for the levofloxacin 240 mg BID, levofloxacin 240 mg QD, levofloxacin 120 mg QD, and placebo treatment arms, respectively. Sample size calculations assumed a 10% discontinuation rate from the study; therefore patients who discontinue the study were not replaced.

Efficacy was evaluated by microbiologic assessment of sputum samples, time to need for anti-pseudomonal antimicrobials, the Cystic Fibrosis Questionaire-Revised (CFQ-R), and pulmonary function tests. In addition, a primary efficacy comparison tested Ho: the average decline in log CFUs of P. aeruginosa from the start of levofloxacin or placebo administration (Day 1) to four weeks later is equal for all four groups, versus $H_1$: the average decline in log CFUs is different for at least one of the four groups using a repeated-measures mixed effects model adjusting for baseline levofloxacin minimum inhibitory concentration (MIC) as a continuous variable (log base 2 transformed), baseline lung function, and geographical region (U.S. versus ex-U.S.). Pair-wise comparisons between all the treatment arms were conducted as secondary analyses.

Efficacy endpoints including clinical endpoints, pulmonary function tests, and additional microbiological parameters were assessed as change from Day 1 to subsequent visits where the endpoint data was collected. Time to need for intravenous/oral/inhaled anti-pseudomonal antimicrobials were assessed from Day 1 until final visit using survival analysis. The primary population for efficacy analysis was the EE population, but efficacy endpoints were also analyzed using the MITT population.

Patients enrolled in the study had a median of 5 courses of aerosolized antibiotics over the previous 12 months. The baseline $FEV_1$ (as percent predicted) was 53% across the entire study and not different among groups. The median baseline MICs of all isolates of Pseudomonas aeruginosa recovered from all patients (n=592) to levofloxacin was 4 mg/L and the MIC90 was 16, also similar across all groups. These MICs are indicative of baseline non-susceptibility/resistance to levofloxacin, as defined by CLSI reference methods and the US FDA.

Concomitant medication used by patients during the study included Dornase alfa, Azithromycin, Salbutamol, Pancrelipase, hypertonic sodium chloride, Seretide, and ADEK, and are summarized for the EE population in Table 8. Table 9 summarizes patient disposition in the study. The results of the study showed were statistically significant advantages of aerosol levofloxacin compared to the placebo in several clinical and microbiological measures, despite the use of concomitant medications, resistance to levofloxacin, and previous use of other aerosolized antibiotics, including tobramycin and colistin.

TABLE 8

| Medication | Placebo (N = 37) | Levofloxacin 120 mg QD (N = 38) | Levofloxacin 240 mg QD (N = 37) | Levofloxacin 240 mg BID (N = 39) | Total (N = 151) |
|---|---|---|---|---|---|
| Dornase alpha | 31 (83.8%) | 27 (71.1%) | 33 (89.2%) | 29 (74.4%) | 120 (79.5%) |
| Azithromycin | 25 (67.6%) | 29 (76.3%) | 26 (70.3%) | 32 (82.1%) | 112 (74.2%) |
| Salbutamol | 25 (67.6%) | 29 (76.3%) | 25 (67.6%) | 23 (59.0%) | 102 (67.5%) |
| Pancrelipase | 9 (51.14%) | 21 (55.3%) | 22 (59.5%) | 21 (53.8%) | 83 (55.0%) |
| Sodium chloride | 22 (59.5%) | 13 (34.2%) | 13 (35.1%) | 22 (56.4%) | 70 (46.4%) |
| Seretide | 9 (51.14%) | 20 (52.6%) | 16 (43.2%) | 15 (38.5%) | 70 (46.4%) |
| ADEK | 10 (27.0%) | 13 (34.2%) | 10 (27.0%) | 13 (33.3%) | 46 (30.5%) |

TABLE 9

| Disposition | | Placebo | Levonoxacin 120 mg. QD | Levofloxacin 240 mg QD | Levofloxacin 240 mg BID | Levofloxacin Total | Total |
|---|---|---|---|---|---|---|---|
| Patients Enrolled | | 37 | 38 | 37 | 39 | | 151 |
| Safety/MITT population | | 37 (100.0%) | 38 (100.0%) | 37 (100.0%) | 39 (100.0%) | 151 (100.0%) | |
| Efficacy Evaluable population | | 32 (86.5%) | 35 (92.1%) | 35 (94.6%) | 34 (87.2%) | 136 (90.1%) | |
| PK population | | 37 (100.0%) | 37 (97.4%) | 37 (100.0%) | 39 (100.0%) | 150 (99.3%) | |
| Completed Study | | 35 (94.6%) | 37 (97.4%) | 35 (94.6%) | 36 (92.3%) | 143 (94.7%) | |
| Discontinued from Study | | 2 (5.4%) | 1 (2.6%) | 2 (5.4%) | 3 (7.7%) | 8 (5.3%) | |
| Primary Reason for Discontinuation from Study | Adverse Event | 2 (5.4%) | 1 (2.6%) | 1 (2.7%) | 2 (5.1%) | 6 (4.0%) | |
| | Withdrawal of consent | 0 (0.0%) | 0 (0.0%) | 1 (2.7%) | 0 (0.0%) | 1 (0.7%) | |
| | Other | 0 (0.0%) | 0 (0.0%) | 0 (0.0%) | 1 (2.6%) | 1 (0.7%) | |
| Primary Reason for Study Drug Discontinuation[a] | | 5 (13.5%) | 3 (7.9%) | 1 (2.7%) | 2 (5.1%) | 11 (7.3%) | |
| | Adverse Event[a] | 4 (10.8%) | 3 (7.9%) | 1 (2.7%) | 2 (5.1%) | 10 (6.6%) | |
| | Other | 1 (2.7%) | 0 (0.0%) | 0 (0.0%) | 0 (0.0%) | 1 (0.7%) | |

[a]Patients could be included in both discontinuation from study and Study Drug categories.

Microbiological Evaluations

Changes in *P. aeruginosa* density (log lo CFU/g sputum) for sputum samples taken from the EE and MITT populations are summarized in Tables 10 and 11, respectively (SD=standard deviation). Changes in MIC for *P. aeruginosa* density ($\log^{10}$ CFU/g sputum) to levofloxacin (all organisms) for EE and MITT populations are shown in Tables 12 and 13, respectively. In addition, changes in the highest MIC values for *P. aeruginosa* isolates to levofloxacin were determined for EE and MITT populations, and are summarized in Tables 14 and 15, respectively. Tables 16 and 17 summarize the percentage of EE and MITT populations, respectively, with categorical changes in highest MIC values for *P. aeruginosa* isolates to levofloxacin. Tables 18 and 19 summarize changes in non-fermenting gram negative bacilli density (NFGNB), excluding *P. aeruginosa*, with only patients with positive NFGNB counts at baseline, for EE and MITT populations, respectively. Tables 20 and 21 summarize changes for presumptive *S. aureus* density ($\log_{10}$ CFU/g sputum) for only patients with positive *S. aureus* counts at baseline, for EE and MITT populations, respectively.

TABLE 10

EE population—*P. aeruginosa* density ($\log_{10}$ CFU sputum)

| | | Placebo (N = 32) | Levofloxacin 120 mg. QD (N = 35) | Levofloxacin 240 mg QD (N = 35) | Levofloxacin 240 mg BID (N = 34) | Combined Levofloxacin 240 mg QD and BID (N = 69) |
|---|---|---|---|---|---|---|
| Day 1 | Mean (SD) | 7.49 (1.674) | 7/43 (1.622) | 7.16 (1.597) | 7.26 (1.433) | 7.21 (1.508) |
| | Median | 8.11 | 8.17 | 7.97 | 7.84 | 7.90 |
| Day 7 | Mean (SD) | 7.37 (1.746) | 6.64 (1.818) | 6.94 (1.783) | 6.23 (1.850) | 6.59 (1.838) |
| | Median | 8.14 | 6.86 | 7.15 | 6.52 | 6.77 |
| Change from Baseline to Day 7 | Mean (SD) | −0.12 (1.422) | −0.76 (1.263) | −0.25 (1.789) | −1.03 (1.921) | −0.64 (1.833) |
| | Median | 0.09 | −0.58 | −0.18 | −0.88 | −0.37 |
| | P-value | | 0.0277 | 0.5892 | 0.0051 | 0.0533 |
| Day 14 | Mean (SD) | 7.48 (1.616) | 7.32 (1.643) | 6.69 (1.628) | 6.43 (1.725) | 6.56 (1.669) |
| | Median | 7.85 | 8.00 | 6.46 | 6.81 | 6.78 |
| Change from Baseline | Mean (SD) | 0.03 (1.355) | −0.10 (1.240) | −0.47 (1.905) | −0.83 (1.901) | −0.65 (1.898) |
| | Median | −0.01 | 0.00 | −0.11 | −0.91 | −0.46 |

TABLE 10-continued

EE population—*P. aeruginosa* density (log₁₀ CFU sputum)

|  |  | Placebo (N = 32) | Levofloxacin 120 mg. QD (N = 35) | Levofloxacin 240 mg QD (N = 35) | Levofloxacin 240 mg BID (N = 34) | Combined Levofloxacin 240 mg QD and BID (N = 69) |
|---|---|---|---|---|---|---|
| to Day 14 | P-value |  | 0.3929 | 0.0998 | 0.0047 | 0.0105 |
| Day 28 | Mean (SD) | 7.85 (1.050) | 7.25 (1.431) | 6.78 (1.896) | 6.65 (1.440) | 6.72 (1.683) |
|  | Median | 8.28 | 7.78 | 7.38 | 6.40 | 6.90 |
| Change from Baseline | Mean (SD) | 0.36 (1.329) | −0.31 (1.050) | −0.38 (1.780) | −0.74 (1.488) | −0.55 (1.645) |
|  | Median | 0.00 | −0.20 | −0.52 | −0.68 | −0.58 |
| to Day 28 | P-Value |  | 0.0093 | 0.0075 | 0.0002 | 0.0002 |

TABLE 11

MITT population—*P. aeruginosa* density (log₁₀ CTU/g sputum)

|  |  | Placebo (N = 37) | Levofloxacin 120 mg. QD (N = 38) | Levofloxacin 240 mg QD (N = 37) | Levofloxacin 240 mg BID (N = 39) | Combined Levofloxacin 240 mg QD and BID (N = 76) |
|---|---|---|---|---|---|---|
| Day 1 | Mean | 7.45 | 7.43 | 7.08 | 7.17 | 7.12 |
|  | (SD) | (1.656) | (1.571) | (1.742) | (1.726) | (1.723) |
|  | Median | 8.10 | 8.16 | 7.97 | 7.90 | 7.91 |
| Day 7 | Mean | 7.21 | 6.68 | 6.79 | 6.16 | 6.47 |
|  | (SD) | (1.750) | (1.778) | (1.854) | (1.969) | (1.927) |
|  | Median | 7.97 | 6.98 | 6.95 | 6.53 | 6.69 |
| Change from Baseline | Mean | −0.24 | −0.70 | −0.31 | −0.97 | −0.65 |
|  | (SD) | (1.429) | (1.257) | (1.823) | (1.846) | (1.852) |
|  | Median | 0.00 | −0.53 | −0.18 | −0.76 | −0.35 |
| to Day 7 | P-value |  | 0.1091 | 0.6986 | 0.0124 | 0.0956 |
| Day 14 | Mean | 7.33 | 7.33 | 6.63 | 6.32 | 6.48 |
|  | (SD) | (1.651) | (1.602) | (1.744) | (1.875) | (1.806) |
|  | Median | 7.85 | 8.00 | 6.46 | 6.70 | 6.61 |
| Change from Baseline | Mean | 0.07 | −0.07 | −0.44 | −0.81 | −0.63 |
|  | (SD) | (1.373) | (1.213) | (1.855) | (1.838) | (1.843) |
|  | Median | −0.02 | 0.00 | −0.10 | −0.79 | −0.40 |
| to Day 14 | P-value |  | 0.7941 | 0.1972 | 0.0091 | 0.0251 |
| Day 28 | Mean | 7.66 | 7.26 | 6.82 | 6.58 | 6.70 |
|  | (SD) | (1.236) | (1.394) | (1.869) | (1.704) | (1.781) |
|  | Median | 8.26 | 7.78 | 7.38 | 6.48 | 6.90 |
| Change from Baseline | Mean | 0.21 | −0.27 | −0.25 | −0.66 | −0.46 |
|  | (SD) | (1.377) | (1.035) | (1.857) | (1.422) | (1.658) |
|  | Median | 0.00 | −0.20 | −0.39 | −0.56 | −0.5 |
| to Day 28 | P-Value |  | 0.0728 | 0.0698 | 0.0014 | 0.0039 |

TABLE 12

EE population—MIC of *P. aeruginosa* to levofloxacin (all organisms) (μg/ml)

|  |  | Placebo (N = 37) | Levofloxacin 120 mg. QD | Levofloxacin 240 mg QD | Levofloxacin 240 mg BID | Combined Levofloxacin 240 mg QD and BID |
|---|---|---|---|---|---|---|
| Day 1 | N | 124 | 140 | 140 | 136 | 276 |
|  | Mean (SD) | 6.0 (5.00) | 11.5 (21.98) | 6.3 (8.85) | 6.8 (8.80) | 6.5 (8.82) |
|  | MIC$_{50}$ | 4 | 4 | 4 | 4 | 4 |
|  | MIC$_{90}$ | 16 | 32 | 16 | 16 | 16 |
| Day 7 | N | 124 | 136 | 132 | 132 | 264 |
|  | Mean (SD) | 6.6 (6.73) | 9.9 (17.28) | 6.8 (16.13) | 8.8 (17.28) | 7.8 (16.71) |
|  | Min, Max | 0.25, 32 | 0.13, 128 | 0.13, 128 | 0.13, 128 | 0.13, 128 |
|  | MIC$_{50}$ | 4 | 4 | 2 | 4 | 4 |
|  | MIC$_{90}$ | 8 | 16 | 16 | 16 | 16 |

TABLE 12-continued

EE population—MIC of *P. aeruginosa* to levofloxacin (all organisms) (µg/ml)

|  |  | Placebo (N = 37) | Levofloxacin 120 mg. QD | Levofloxacin 240 mg QD | Levofloxacin 240 mg BID | Combined Levofloxacin 240 mg QD and BID |
|---|---|---|---|---|---|---|
| Day 14 | N | 120 | 140 | 136 | 132 | 268 |
|  | Mean (SD) | 5.6 (6.79) | 13.0 (29.34) | 6.6 (9.44) | 8.4 (14.47) | 7.5 (12.19) |
|  | $MIC_{50}$ | 4 | 4 | 4 | 4 | 4 |
|  | $MIC_{90}$ | 8 | 37 | 16 | 16 | 16 |
| Day 28 | N | 128 | 132 | 136 | 124 | 260 |
|  | Mean (SD) | 5.0 (3.97) | 8.9 (13.47) | 6.0 (7.57) | 10.1 (16.32) | 8.0 (12.67) |
|  | $MIC_{50}$ | 4 | 4 | 4 | 4 | 4 |
|  | $MIC_{90}$ | 8 | 16 | 16 | 32 | 16 |

TABLE 13

MITT population—MIC of *P. aeruginosa* to levofloxacin (all organisms) (µg/ml)

|  |  | Placebo | Levofloxacin 120 mg. QD | Levofloxacin 240 mg QD | Levofloxacin 240 mg BID | Combined Levofloxacin 240 mg QD and BID |
|---|---|---|---|---|---|---|
| Day 1 | N | 140 | 152 | 148 | 157 | 300 |
|  | Mean (SD) | 6.1 (5.40) | 11.0 (21.17) | 6.1 (8.64) | 6.8 (8.47) | 6.4 (8.55) |
|  | $MIC_{50}$ | 4 | 4 | 4 | 4 | 4 |
|  | $MIC_{90}$ | 16 | 32 | 16 | 16 | 16 |
| Day 7 | N | 136 | 144 | 140 | 140 | 780 |
|  | Mean (SD) | 6.8(7.33) | 9.6 (16.83) | 6.7 (15.69) | 8.6 (16.82) | 7.6 (16.27) |
|  | $MIC_{50}$ | 4 | 4 | 4 | 4 | 4 |
|  | $MIC_{90}$ | 16 | 16 | 16 | 16 | 16 |
| Day 14 | N | 128 | 144 | 144 | 140 | 284 |
|  | Mean (SD) | 5.8 | 12.9 (28.95) | 6.5 (9.23) | 8.2 (14.11) | 7.3 (11.90) |
|  | $MIC_{50}$ | 4 | 6 | 4 | 4 | 4 |
|  | $MIC_{90}$ | 16 | 32 | 16 | 16 | 16 |
| Day 28 | N | 137 | 136 | 140 | 137 | 272 |
|  | Mean (SD) | 4.9 (3.97) | 8.8 (13.32) | 5.9 (750) | 9.9 (15.98) | 7.9 (12.51) |
|  | $MIC_{50}$ | 4 | 4 | 4 | 4 | 4 |
|  | $MIC_{90}$ | 8 | 16 | 16 | 32 | 16 |

TABLE 14

EE population—MIC of *P. aeruginosa* to levofloxacin (all organisms) (µg/ml)

|  |  | Placebo (N = 32) | Levofloxacin 120 mg. QD (N = 35) | Levofloxacin 240 mg QD (N = 35) | Levofloxacin 240 mg BID (N = 34) | Combined Levofloxacin 240 mg QD and BID (N = 69) |
|---|---|---|---|---|---|---|
| Day 1 | Mean (SD) | 8.79 (6.661) | 14.98 (22.383) | 9.35 (12.991) | 11.58 (13.399) | 10.46 (13.144) |
|  | $MIC_{50}$ | 8 | 8 | 4 | 6 | 4 |
|  | $MIC_{90}$ | 16 | 32 | 32 | 32 | 32 |
| Day 7 | Mean (SD) | 8.77 (7.455) | 15.71(22.523) | 10.86 (22.222) | 13.05 (22.838) | 11.95 (22.385) |
|  | $MIC_{50}$ | 8 | 8 | 4 | 4 |  |
|  | $MIC_{90}$ | 16 | 32 | 16 | 32 | 32 |
| Day 14 | Mean (SD) | 8.42 (11.437) | 21.16 (43.639) | 9.56 (12.409) | 15.18 (25.541) | 12.33 (20.032) |
|  | $MIC_{50}$ | 6 | 8 | 8 | 4 | 8 |
|  | $MIC_{90}$ | 16 | 32 | 16 | 32 | 3 |
| Day 28 | Mean (SD) | 7.31 (4.961) | 12.91 (15.669) | 9.42 (11.658) | 17.97 (26.008) | 13.56 (20.252) |
|  | $MIC_{50}$ | 8 | 8 | 8 | 8 | 8 |
|  | $MIC_{90}$ | 16 | 32 | 16 | 32 | 32 |

TABLE 15

MITT population—Highest MIC of *P. aeruginosa* to levofloxacin (μg/ml)

|  |  | Placebo (N = 37) | Levofloxacin 120 mg. QD (N = 38) | Levofloxacin 240 mg QD (N = 37) | Levofloxacin 240 mg BID (N = 39) | Combined Levofloxacin 240 mg QD and BID (N = 76) |
|---|---|---|---|---|---|---|
| Day 1 | Mean (SD) | 9.04 (7.593) | 14.32 (21.583) | 9.06 (12.685) | 11.41 (12.816) | 10.25 (12.720 |
|  | $MIC_{50}$ | 8 | 8 | 4 | 6 | 4 |
|  | $MIC_{90}$ | 16 | 32 | 32 | 32 | 32 |
| Day 7 | Mean (SD) | 9.06 (8.203) | 15.17 (21.991) | 10.53 (21.615) | 12.96 (21.902) | 11.76 (21.639) |
|  | $MIC_{50}$ | 8 | 8 | 4 | 6 | 4 |
|  | $MIC_{90}$ | 16 | 32 | 16 | 32 | 16 |
| Day 14 | Mean (SD) | 8.78 (11.554) | 20.34 (42.555) | 9.28 (12.136) | 14.86 (24.522) | 12.07 (19.415) |
|  | $MIC_{50}$ | 6 | 8 | 8 | 6 | 8 |
|  | $MIC_{90}$ | 16 | 16 | 16 | 32 | 32 |
| Day 28 | Mean (SD) | 7.78 (6.334) | 12.74 (15.286) | 9.17 (11.389) | 17.91 (25.067) | 13.48 (19.734) |
|  | $MIC_{50}$ | 8 | 8 | 8 | 8 | 8 |
|  | $MIC_{90}$ | 16 | 32 | 16 | 16 | 32 |

TABLE 16

EE population—Categorical change in highest MIC of *P. aeruginosa* to levofloxacin (% population)

|  |  | Placebo (N = 32) | Levofloxacin 120 mg. QD (N = 35) | Levofloxacin 240 mg QD (N = 35) | Levofloxacin 240 mg BID (N = 34) | Combined Levofloxacin 240 mg QD and BID (N = 69) |
|---|---|---|---|---|---|---|
| Change from Baseline to Day 7 | >=4 fold increase | 6.5% | 2.9% | 12.1% | 9.1% | 10.6% |
|  | <4 fold increase | 93.5% | 97.1% | 87.9% | 90.9% | 89.4% |
| Change from Baseline to Day 14 | >=4 fold increase | 10.0% | 11.4% | 5.9% | 18.2% | 11.9% |
|  | <4 fold increase | 90.0% | 88.6% | 94.1% | 81.8% | 88.1% |
| Change from Baseline to Day 28 | >=4 fold increase | 9.4% | 9.1% | 8.8% | 15.6% | 10.6% |
|  | <4 fold increase | 90.6% | 90.9% | 91.2% | 84.4% | 87.9% |
| Change from Baseline to Day 56/Early Term | >=4 fold increase | 22.6% | 6.2% | 5.7% | 15.2% | 10.3% |
|  | <4 fold increase | 77.4% | 93.6% | 94.3% | 84.8% | 89.7% |

TABLE 17

MITT population—Categorical change in highest MIC of *P. aeruginosa* to levofloxacin (% population)

|  |  | Placebo (N = 37) | Levofloxacin 120 mg. QD (N = 38) | Levofloxacin 240 mg QD (N = 37) | Levofloxacin 240 mg BID (N = 39) | Combined Levofloxacin 240 mg QD and BID (N = 76) |
|---|---|---|---|---|---|---|
| Change from Baseline to Day 7 | >=4 fold increase | 5.7% | 2.8% | 11.4% | 8.3% | 9.9% |
|  | <4 fold increase | 94.3% | 97.2% | 88.6% | 91.7% | 90.1% |
| Change from Baseline to Day 14 | >=4 fold increase | 8.8% | 10.8% | 5.6% | 16.7% | 11.1% |
|  | <4 fold increase | 91.2% | 89.2% | 94.4% | 83.3% | 88.9% |
| Change from Baseline to Day 28 | >=4 fold increase | 8.3% | 8.6% | 8.3% | 14.3% | 11.3% |
|  | <4 fold increase | 91.7% | 91.4% | 91.7% | 85.7% | 88.7% |
| Change from Baseline to Day 56/Early Term | >=4 fold increase | 20.0% | 5.9% | 5.4% | 13.9% | 9.6% |
|  | <4 fold increase | 80.0% | 94.1% | 94.6% | 86.1% | 90.4% |

TABLE 18

EE population—Change in non-fermenting grain negative bacilli density ($log_{10}$ CFU/g sputum)

|  |  | Placebo (N = 5) | Levofloxacin 120 mg. QD (N = 5) | Levofloxacin 240 mg QD (N = 5) | Levofloxacin 240 mg BID (N = 4) | Combined Levofloxacin 240 mg QD and BID (N = 9) | Combined Levofloxacin (N = 14) |
|---|---|---|---|---|---|---|---|
| Day 1 | Mean (SD) | 6.60 (1.113) | 5.69 (2.674) | 4.65 (2.271) | 5.52 (2.291) | 5.03 (2.182) | 5.27 (2.288) |
| Day 7 | Mean (SD) | 6.26 (3.018) | 4.54 (2.361) | 2.18 (1.614) | 5.01 (3.068) | 3.44 (2.657) | 3.83 (2.522) |
| Change from Baseline to Day 7 | Mean (SD) | −0.34 (2.610) | −1.15 (1.607) | −2.47 (3.346) | −0.51 (3.184) | −1.60 (3.235) | −1.44 (2.699) |
|  | P-value |  | 0.1206 | 0.0476 | 0.7552 | 0.1755 | 0.1178 |

TABLE 18-continued

EE population—Change in non-fermenting grain negative bacilli density (log$_{10}$ CFU/g sputum)

| | | Placebo (N = 5) | Levo-floxacin 120 mg. QD (N = 5) | Levo-floxacin 240 mg QD (N = 5) | Levo-floxacin 240 mg BID (N = 4) | Combined Levo-floxacin 240 mg QD and BID (N = 9) | Combined Levo-floxacin (N = 14) |
|---|---|---|---|---|---|---|---|
| Day 14 | Mean | 5.94 | 3.15 | 2.04 | 6.02 | 3.80 | 3.57 |
| | (SD) | (3.002) | (3.122) | (2.315) | (1.894) | (2.903) | (2.880) |
| Change from Baseline to Day 28 | Mean | −0.66 | −2.54 | −2.61 | 0.50 | −1.23 | −1.70 |
| | (SD) | (2.315) | (3.057) | (3.222) | (1.638) | (2.980) | (2.961) |
| | P-value | | 0.0894 | 0.1571 | 0.5983 | 0.5932 | 0.2824 |
| Day 28 | Mean | 5.60 | 5.10 | 1.36 | 5.01 | 2.98 | 3.63 |
| | (SD) | (3.012) | (2.938) | (0.808) | (2.758) | (2.621) | (2.787) |
| Change from Baseline to Day 28 | Mean | −1.00 | −1.44 | −3.29 | −0.51 | −2.05 | −1.87 |
| | (SD) | (3.262) | (4.739) | (2.401) | (1.438) | (2.407) | (3.092) |
| | P-value | | 0.2997 | 0.0479 | 0.9881 | 0.2237 | 0.1956 |

TABLE 19

MITT population—Change in non-fermenting gram negative bacilli density (log$_{10}$ CFU/g sputum)

| | | Placebo (N = 6) | Levo-floxacin 120 mg. QD (N = 5) | Levo-floxacin 240 mg QD (N = 7) | Levo-floxacin 240 mg BID (N = 5) | Combined Levo-floxacin 240 mg QD and BID (N = 12) | Combined Levo-floxacin (N = 17) |
|---|---|---|---|---|---|---|---|
| Day 1 | Mean | 5.88 | 5.69 | 5.26 | 6.05 | 5.59 | 5.62 |
| | (SD) | (2.018) | (2.674) | (2.203) | (2.317) | (2.184) | (2.251) |
| Day 7 | Mean | 5.44 | 4.54 | 2.52 | 5.63 | 3.82 | 4.03 |
| | (SD) | (3.375) | (2.361) | (1.997) | (3.004) | (2.832) | (2.650) |
| Change from Baseline to Day 7 | Mean | −0.45 | −1.15 | −2.73 | −0.42 | −1.77 | −1.59 |
| | (SD) | (2.350) | (1.607) | (2.882) | (2.765) | (2.955) | (2.594) |
| | P-value | | 0.2680 | 0.0485 | 0.6562 | 0.3749 | 0.2748 |
| Day 14 | Mean | 5.17 | 3.25 | 3.08 | 6.50 | 4.50 | 4.11 |
| | (SD) | (3.286) | (3.122) | (2.599) | (1.964) | (2.862) | (2.911) |
| Change from Baseline to Day 28 | Mean | −0.72 | −2.54 | −2.18 | 0.45 | −1.08 | −1.51 |
| | (SD) | (2.075) | (3.057) | (2.784) | (1.423) | (2.605) | (2.733) |
| | P-value | | 0.1020 | 0.1924 | 0.2832 | 0.9333 | 0.4410 |
| Day 28 | Mean | 4.88 | 5.10 | 2.77 | 5.63 | 3.96 | 4.24 |
| | (SD) | (3.215) | (2.938) | (2.505) | (2.762) | (2.892) | (2.850) |
| Change from Baseline to Day 28 | Mean | −1.00 | −1.44 | −2.49 | −0.43 | 1.63 | −1.58 |
| | (SD) | (2.917) | (4.739) | (2.538) | (1.260) | (2.284) | (2.885) |
| | P-value | | 0.5733 | 0.1606 | 0.4532 | 0.7266 | 0.6211 |

TABLE 20

EE population—Change for presumptive
S. aureus density ($\log_{10}$ CFU/g sputum)

|  |  | Placebo (N = 16) | Levofloxacin 120 mg. QD (N = 16) | Levofloxacin 240 mg QD (N = 19) | Levofloxacin 240 mg BID (N = 13) | Combined Levofloxacin 240 mg QD and BID (N = 32) | Combined Levofloxacin (N = 48) |
|---|---|---|---|---|---|---|---|
| Day 1 | Mean | 5.67 | 5.72 | 5.64 | 5.68 | 5.65 | 5.68 |
|  | (SD) | (2.125) | (1.871) | (1.985) | (2.196) | (2.038) | (1.964) |
| Day 7 | Mean | 5.53 | 4.53 | 5.34 | 4.96 | 5.18 | 4.97 |
|  | (SD) | (2.152) | (2.272) | (2.321) | (2.992) | (2.574) | (2.473) |
| Change from Baseline to Day 7 | Mean | −0.14 | −1.19 | −0.30 | −0.72 | −0.47 | −0.71 |
|  | (SD) | (0.968) | (1.722) | (1.579) | (1.159) | (1.419) | (1.546) |
|  | P-value |  | 0.0347 | 0.5969 | 0.2039 | 0.2891 | 0.1059 |
| Day 14 | Mean | 5.35 | 5.30 | 5.14 | 4.70 | 4.96 | 5.08 |
|  | (SD) | (2.469) | (2.543) | (2.594) | (2.829) | (2.656) | (2.597) |
| Change from Baseline to Day 28 | Mean | −0.32 | −0.42 | −0.50 | −0.98 | −0.69 | −0.60 |
|  | (SD) | (1.259) | (1.273) | (1.766) | (0.998) | (1.502) | (1.422) |
|  | P-value |  | 0.6684 | 0.5883 | 0.1593 | 0.2497 | 0.3259 |
| Day 28 | Mean | 5.46 | 5.31 | 4.56 | 5.42 | 4.89 | 5.04 |
|  | (SD) | (2.647) | (2.482) | (2.724) | (2.973) | (2.806) | (2.680) |
| Change from Baseline to Day 28 | Mean | −0.21 | −0.41 | −1.08 | −0.38 | −0.81 | −0.67 |
|  | (SD) | (1.137) | (1.146) | (2.622) | (1.144) | (2.173) | (1.882) |
|  | P-value |  | 0.6124 | 0.1186 | 0.6403 | 0.2589 | 0.3159 |

TABLE 21

EE population—Change for presumptive
S. aureus density ($\log_{10}$ CFU/g sputum)

|  |  | Placebo (N = 19) | Levofloxacin 120 mg. QD (N = 17) | Levofloxacin 240 mg QD (N = 21) | Levofloxacin 240 mg BID (N = 16) | Combined Levofloxacin 240 mg QD and BID (N = 37) | Combined Levofloxacin (N = 54) |
|---|---|---|---|---|---|---|---|
| Day 1 | Mean | 6.06 | 5.89 | 5.63 | 5.51 | 5.58 | 5.68 |
|  | (SD) | (2.152) | (1.941) | (1.894) | (2.318) | (2.058) | (2.009) |
| Day 7 | Mean | 5.78 | 4.75 | 5.23 | 4.65 | 4.99 | 4.91 |
|  | (SD) | (2.071) | (2.382) | (2.249) | (2.954) | (2.543) | (2.472) |
| Change from Baseline to Day 7 | Mean | −0.28 | −1.14 | −0.40 | −0.66 | −0.51 | −0.71 |
|  | (SD) | (0.985) | (1.681) | (1.615) | (1.243) | (1.458) | (1.545) |
|  | P-value |  | 0.0563 | 0.6856 | 0.3058 | 0.3995 | 0.1653 |
| Day 14 | Mean | 5.64 | 5.48 | 4.97 | 4.32 | 4.70 | 4.95 |
|  | (SD) | (2.387) | (2.568) | (2.579) | (2.820) | (2.662) | (2.633) |
| Change from Baseline to Day 28 | Mean | −0.42 | −0.41 | −0.66 | −0.99 | −0.80 | −0.68 |
|  | (SD) | (1.216) | (1.233) | (1.907) | (0.981) | (1.578) | (1475) |
|  | P-value |  | 0.8238 | 0.5691 | 0.2231 | 0.2393 | 0.4058 |
| Day 28 | Mean | 5.65 | 5.49 | 4.48 | 4.95 | 4.66 | 4.93 |
|  | (SD) | (2.511) | (2.510) | (2.633) | (3.018) | (2.760) | (2.684) |
| Change froin Baseline to Day 28 | Mean | −0.41 | −0.41 | −1.15 | −0.44 | −0.87 | −0.72 |
|  | (SD) | (1.240) | (1.110) | (2.578) | (1.150) | (2.131) | (1.860) |
|  | P-value |  | 0.8341 | 0.1623 | 0.7846 | 0.3528 | 0.4572 |

Figure 3:
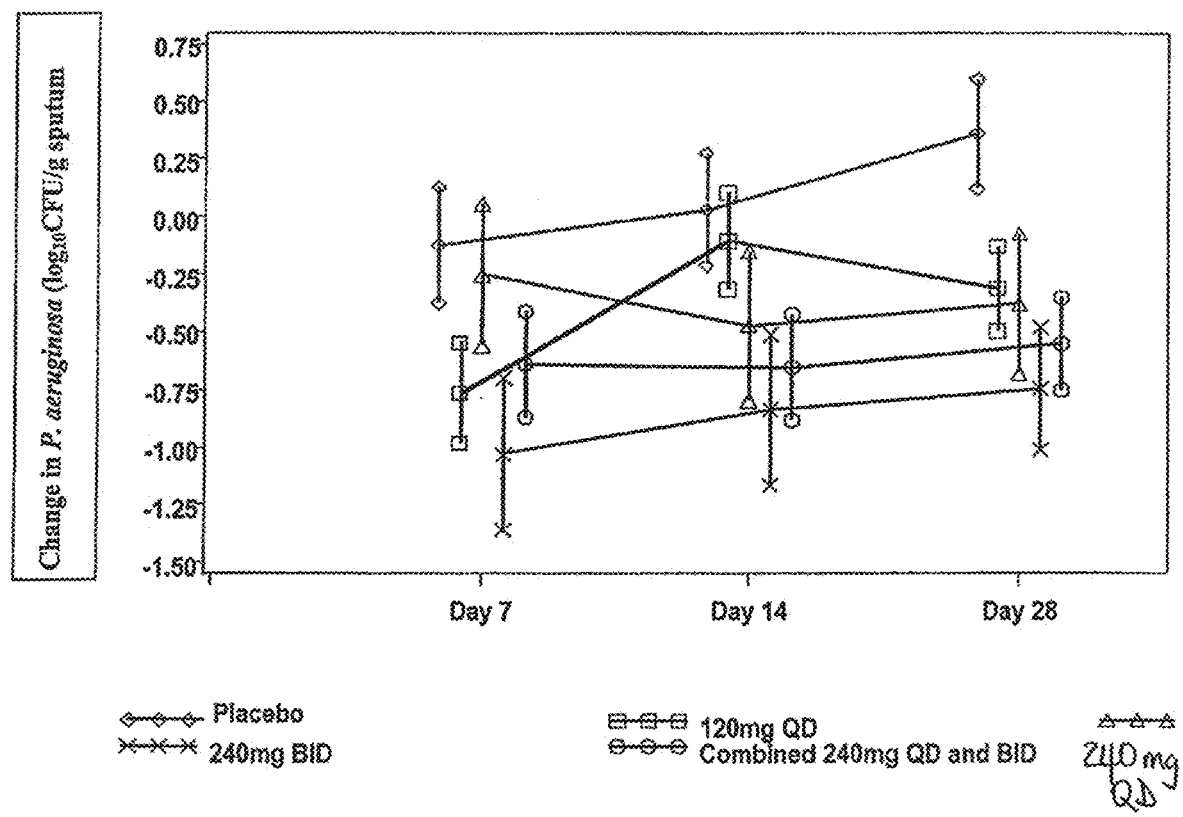
Figure 4:
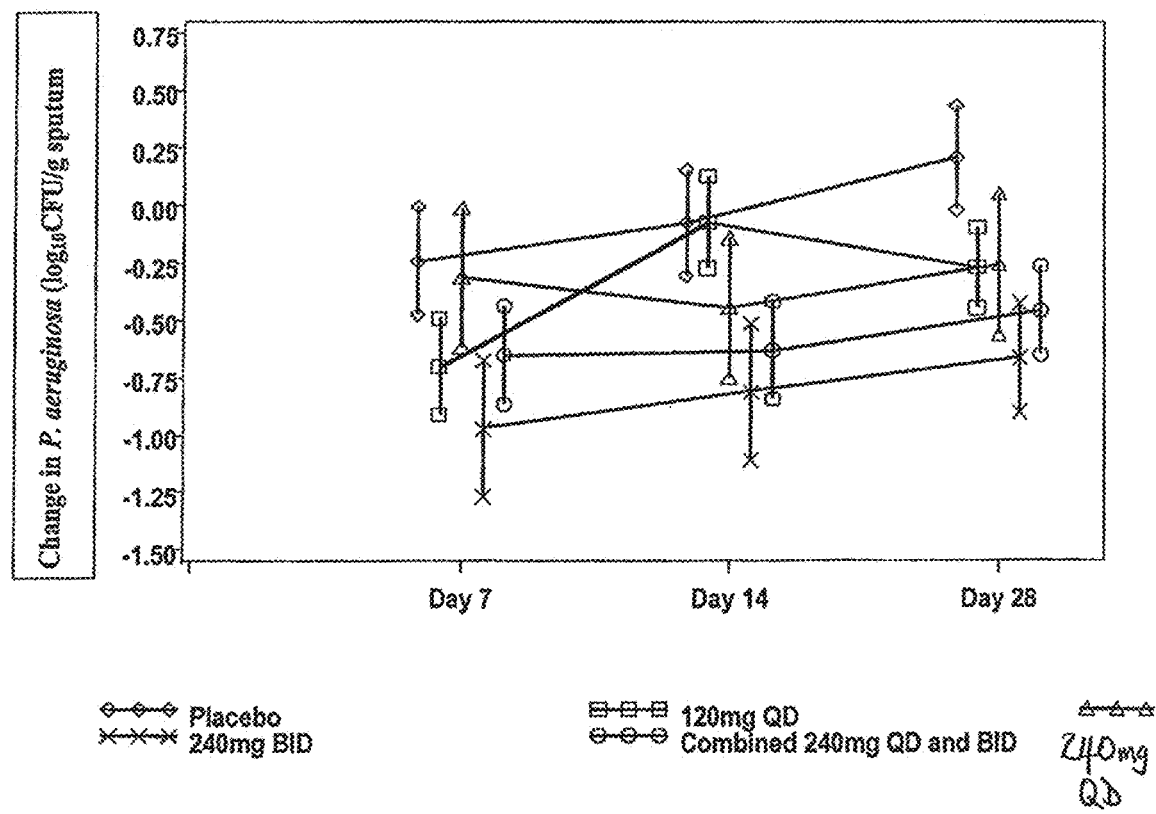

*P. aeruginosa* densities were reduced from baseline values on (Day 1) over the course of the study in all three levofloxacin treatment groups in both the EE and MITT populations. FIGS. 3 and 4 show mean changes in *P. aeruginosa* densities over time for each treatment group.

In the EE population, there was a decrease of *P. aeruginosa* density in patients administered levofloxacin 240 mg BID from a median value of 7.84 $\log_{10}$ CFU/g sputum on Day 1 to a median value of 6.40 $\log_{10}$ CFU/g sputum on Day 28, representing a reduction in *P. aeruginosa* density in sputum of approximately 96%. In patients administered levofloxacin 240 mg QD, there was a decrease in *P. aeruginosa* density from a median value of 7.97 $\log_{10}$ CFU/g sputum on Day 1 to a median value of 7.38 $\log_{10}$ CFU/g sputum on Day 28, representing a reduction in *P. aeruginosa* density in sputum of approximately 74%. In patients administered levofloxacin 120 mg QD, there was a decrease in *P. aeruginosa* density from a median value of 8.17 $\log_{10}$ CFU/g sputum on Day 1 to a median value of 7.78 $\log_{10}$ CFU/g sputum on Day 28, representing a reduction in *P. aeruginosa* density in sputum of approximately 59%. The largest differences for *P. aeruginosa* density in sputum between patients administered placebo and patients administered levofloxacin were 1.62 $\log_{10}$ CFU/g sputum on Day 7, 1.39 $\log_{10}$ CFU/g sputum on Day 14, and 1.88 $\log_{10}$ CFU/g sputum on Day 28.

In the MITT population, there was a decrease of *P. aeruginosa* density in patients administered levofloxacin 240 mg BID from a median value of 7.90 $\log_{10}$, CFU/g sputum on Day 1 to a median value of 6.48 $\log_{10}$ CFU/g sputum on Day 28, representing a reduction in *P. aeruginosa* density in sputum of approximately 96%. In patients administered levofloxacin 240 mg QD, there was a decrease in *P. aeruginosa* density from a median value of 7.97 $\log_{10}$ CFU/g sputum on Day 1 to a median value of 7.38 $\log_{10}$ CFU/g sputum on Day 28, representing a reduction in *P. aeruginosa* density in sputum of approximately 74%. In patients administered levofloxacin 120 mg QD, there was a decrease in *P. aeruginosa* density from a median value of 8.16 $\log_{10}$ CFU/g sputum on Day 1 to a median value of 7.78 $\log_{10}$ CFU/g sputum on Day 28, representing a reduction in *P. aeruginosa* density in sputum of approximately 58%. The largest differences for *P. aeruginosa* density in sputum between patients administered placebo and patients administered levofloxacin were 1.44 $\log_{10}$ CFU/g sputum on Day 7, 1.39 $\log_{10}$ CFU/g sputum on Day 14, and 1.78 $\log_{10}$ CFU/g sputum on Day 28.

For the EE and MITT populations, baseline MIC50 values for *P. aeruginosa* isolates from patients administered placebo, 120 mg QD, 240 mg QD, and 240 mg BID were 8 µg/ml, 8, 4 µg/ml, and 6 µg/ml, respectively. On Day 28, $MIC_{50}$ values for *P. aeruginosa* isolates from patients administered placebo, 120 mg QD, 240 mg QD, and 240 mg BID were 8 µg/ml, 8 µg/ml, 8 µg/ml, and 8 µg/ml, respectively. Baseline $MIC_{90}$ values for *P. aeruginosa* isolates from patients administered placebo, 120 mg QD, 240 mg QD, and 240 mg BID were 16 µg/ml, 32 µg/ml, 32 µg/ml, and 32 µg/ml, respectively. On Day 28, $MIC_{90}$ values for *P. aeruginosa* isolates from patients administered placebo, 120 mg QD, 240 mg QD, and 240 mg BID were 16 µg/ml, 32 µg/ml, 16 µg/ml, and 32 µg/ml, respectively.

The similarity of corresponding $MIC_{50}$ and $MIC_{90}$ values between Day 1 and Day 28 for the EE and MITT populations indicates that *P. aeruginosa* cultures from patients did not develop any significant resistance to levofloxacin.

Clinical Evaluations—CFQ-R Questionnaire

Patients completed the CFQ-R questionnaire with domains that included: respiratory, body image, digestion, eating, emotion, health perception, physical, role/school, social, treatment burden, vitality, and weight. Tables 22 and 23 summarize results for the respiratory domain of the CFQ-R for EE and MITT populations, respectively. Table 24 summarizes changes in score for various domains of the CFQ-R from baseline to visit 4 in the MITT population.

TABLE 22

| | | Placebo (N = 32) | Levofloxacin 120 mg. QD (N = 35) | Levofloxacin 240 mg QD (N = 35) | Levofloxacin 240 mg BID (N = 34) | Combined Levofloxacin 240 mg QD and BID (N = 69) |
|---|---|---|---|---|---|---|
| Day 1 | Mean | 66.7 | 63.5 | 60.8 | 60.3 | 60.5 |
| | (SD) | (14.39) | (15.84) | (15.83) | (16.42) | (16.00) |
| | Median | 66.7 | 66.7 | 61.1 | 61.1 | 61.1 |
| Day 14 | Mean | 66.7 | 67.8 | 63.2 | 68.8 | 66.0 |
| | (SD) | (15.84) | (13.79) | (19.34) | (19.15) | (19.31) |
| | Median | 63.9 | 66.7 | 66.7 | 72.2 | 66.7 |
| Change from Baseline to Day 14 | Mean | −0.0 | 4.3 | 2.1 | 8.5 | 5.3 |
| | (SD) | (11.20) | (9.82) | (16.41) | (155.5) | (16.19) |
| | Median | 0.0 | 5.5 | 0.0 | 5.6 | 5.6 |
| | P-value | | 0.3953 | 0.9534 | 0.0374 | 0.2171 |
| Day 28 | Mean | 64.9 | 65.1 | 61.7 | 66.0 | 63.8 |
| | (SD) | (18.53) | (17.28) | (19.37) | (19.68) | (19.49) |
| | Median | 63.9 | 66.7 | 66.7 | 72.2 | 66.7 |
| Change from Baseline to Day 28 | Mean | −1.7 | 1.6 | 1.0 | 5.2 | 3.0 |
| | (SD) | (14.90) | (12.32) | (14.91) | (17.56) | (16.27) |
| | Median | 0.0 | 0.0 | 0.0 | 5.5 | 0.0 |
| | P-value | | 0.6183 | 0.8145 | 0.0924 | 0.2690 |

TABLE 23

| | | Placebo (N = 37) | Levofloxacin 120 mg. QD (N = 38) | Levofloxacin 240 mg QD (N = 37) | Levofloxacin 240 mg BID (N = 39) | Combined Levofloxacin 240 mg QD and BID (N = 76) |
|---|---|---|---|---|---|---|
| Day 1 | Mean | 64.9 | 62.3 | 61.3 | 60.5 | 60.9 |
| | (SD) | (14.17) | (15.88) | (15.52) | (16.31) | (15.83) |
| | Median | 66.7 | 61.1 | 61.1 | 61.1 | 61.1 |
| Day 14 | Mean | 64.6 | 67.1 | 63.0 | 68.4 | 65.8 |
| | (SD) | (15.84) | (13.70) | (19.74) | (19.51) | (19.68) |
| | Median | 61.1 | 66.7 | 66.7 | 72.2 | 69.4 |
| Change from Baseline to Day 14 | Mean | −0.3 | 4.5 | 1.4 | 7.5 | 4.5 |
| | (SD) | (10.79) | (9.78) | (17.54) | (15.30) | (16.59) |
| | Median | 0.0 | 5.5 | 0.0 | 5.6 | 5.5 |
| | P-value | | 0.2559 | 0.8964 | 0.0334 | 0.1937 |
| Day 28 | Mean | 63.1 | 64.6 | 61.6 | 64.4 | 63.0 |
| | (SD) | (18.01) | (16.94) | (19.74) | (20.39) | (19.98) |
| | Median | 61.1 | 66.7 | 66.7 | 72.2 | 66.7 |
| | Min, Max | 22, 94 | 17, 100 | 17, 89 | 22, 94 | 17, 94 |
| Change from | Mean | −1.8 | 2.0 | 0.3 | 3.0 | 1.7 |
| | (SD) | (14.11) | (12.23) | (16.14) | (19.18) | (17.66) |

TABLE 23-continued

MITT population—Respiratory domain of CFQ-R

|  |  | Placebo (N = 37) | Levofloxacin 120 mg. QD (N = 38) | Levofloxacin 240 mg. QD (N = 37) | Levofloxacin 240 mg BID (N = 39) | Combined Levofloxacin 240 mg QD and BID (N = 76) |
|---|---|---|---|---|---|---|
| Baseline to Day 28 | Median P-value | 0.0 | 0.0 0.5029 | 0.0 0.8365 | 0.0 0.2174 | 0.0 0.4069 |

TABLE 24

LS Mean Change from Baseline

| CFQ-R Scale | Placebo (N = 37) | Levofloxacin 240 mg. BID (N = 39) | LS Mean Difference (95% CI) | P-Value |
|---|---|---|---|---|
| Respiratory | −0.44 | 4.06 | 4.50 (−2.68, 11.67) | 0.2174 |
| Body Image | 0.59 | 0.34 | −0.25 (−6.00, 5.50) | 0.9315 |
| Digestion | −1.35 | 1.11 | 2.46 (−3.27, 8.18) | 0.3975 |
| Eating | −3.29 | 2.41 | 5.70 (0.78, 10.62) | 0.0235 |
| Emotion | 2.32 | 2.22 | −0.09 (−4.34, 4.15) | 0.9651 |
| Health Perception | −2.1 | 0.52 | 2.58 (−3.70, 8.86) | 0.4117 |
| Physical | −2.80 | 3.14 | 5.94 (0.75, 11.13) | 0.0252 |
| Role/School | −1.41 | −1.94 | −0.53 (−5.43, 4.38) | 0.8324 |
| Social | −1.68 | 0.69 | 2.37 (−2.66, 7.40) | 0.3530 |
| Treatment Burden | −0.99 | −0.93 | 0.06 (−5.84, 5.95) | 0.9851 |
| Vitality | −1.88 | 1.23 | 3.11 (−2.91, 9.13) | 0.3085 |
| Weight | 4.72 | 10.06 | 5.4 (−4.38, 15.06) | 0.2792 |

For the EE population, mean changes from baseline to Day 28 for respiratory factors measured by the CFQ-R for patient administered placebo, 120 mg QD, 240 mg QD, and 240 mg BID treatment groups were 1.6, 1.0, 5.2, and 3.0 units, respectively. For the MITT population, mean changes from baseline to Day 28 for respiratory factors for patient administered placebo, 120 mg QD, 240 mg QD, and 240 mg BID treatment groups were 2.0, 0.3, 3.0, and 1.7 units, respectively. The 240 mg BID group in the EE population demonstrated a statistically significant improvement in respiratory score on Day 14.

The CFQ-R eating score also showed improvement with the difference in the 240 mg BID group in the MITT population showing statistically significant improvement at Day 28.

Time to Patient Need for Anti-Pseudomonal Antimicrobials

Time to administration of intravenous/oral/inhaled anti-pseudomonal antimicrobials from Day 1 until Final visit was measured for patients with at least one of the following: decreased exercise tolerance, increased cough, increased sputum/chest congestion, and decreased appetite. The proportion of patients requiring anti-pseudomonal antimicrobials (inhaled or systemic) over time was analyzed using a Cox proportional hazards model. Table 25 summarizes results for time to need for anti-pseudomonal antimicrobials for EE and MITT populations.

TABLE 25

EE and MITT populations—Parameters for time to need anti-pseudomonal antimicrobials

|  |  | Placebo (N = 32) | Levofloxacin 120 mg. QD (N = 35) | Levofloxacin 240 mg QD (N = 35) | Levofloxacin 240 mg BID (N = 34) | Combined Levofloxacin 240 mg QD and BID (N = 69) |
|---|---|---|---|---|---|---|
| EE population | Patients Requiring Anti-Pseudomonal | 40.6% | 20.0% | 25.7% | 20.6% | 23.2% |

TABLE 25-continued

EE and MITT populations—Parameters for time to need anti-pseudomonal antimicrobials

|  |  | Placebo (N = 32) | Levofloxacin 120 mg. QD (N = 35) | Levofloxacin 240 mg QD (N = 35) | Levofloxacin 240 mg BID (N = 34) | Combined Levofloxacin 240 mg QD and BID (N = 69) |
|---|---|---|---|---|---|---|
|  | Antimicrobials Hazard Ratio [95% CI] P-value |  | 0.39 [0.15, 1.01] 0.0522 | 0.48 [0.20, 1.17] 0.1050 | 0.26 [0.10, 0.69] 0.0067 | 0.37 [0.17, 0.81] 0.0123 |
| MITT population | Number (%) of Patients Requiring Anti-Pseudomonal Antimicrobials Hazard Ratio [95% CI] P-value | 48.6% | 18.4% 0.29 [0.12, 0.71] 0.0069 | 27.0% 0.39 [0.17, 0.87] 0.0215 | 20.5% 0.21 [0.09, 0.52] 0.0007 | 23.7% 0.30 [0.15, 0.60] 0.0007 |

Figure 5:
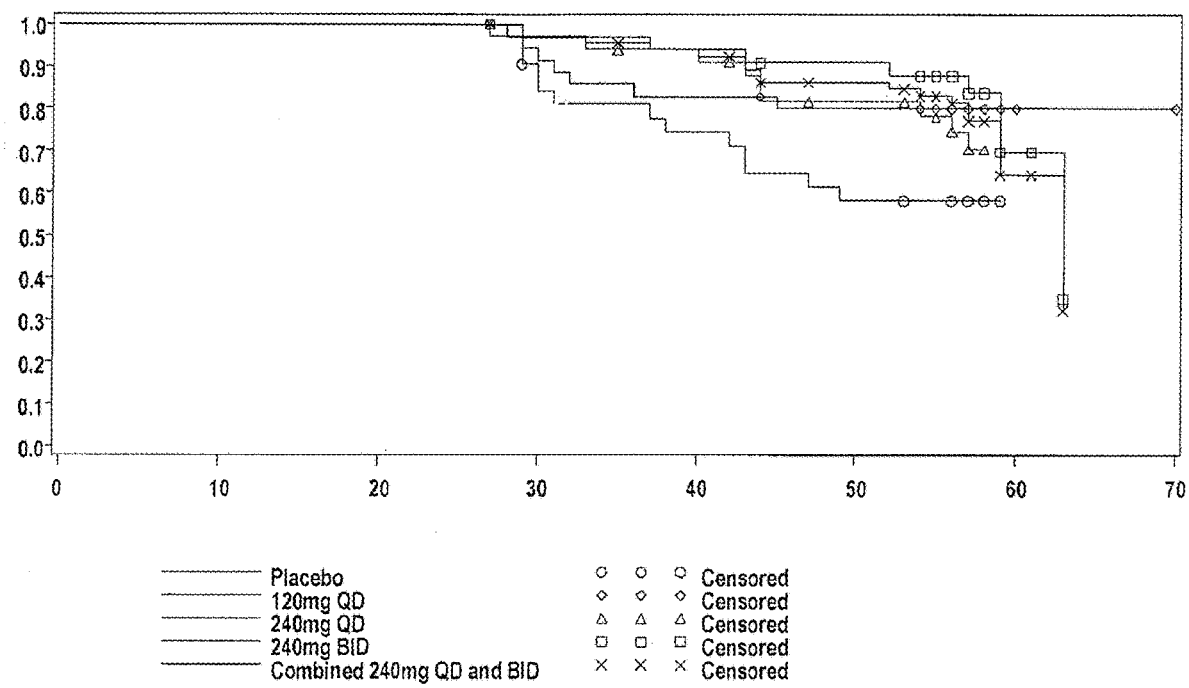
Figure 6:
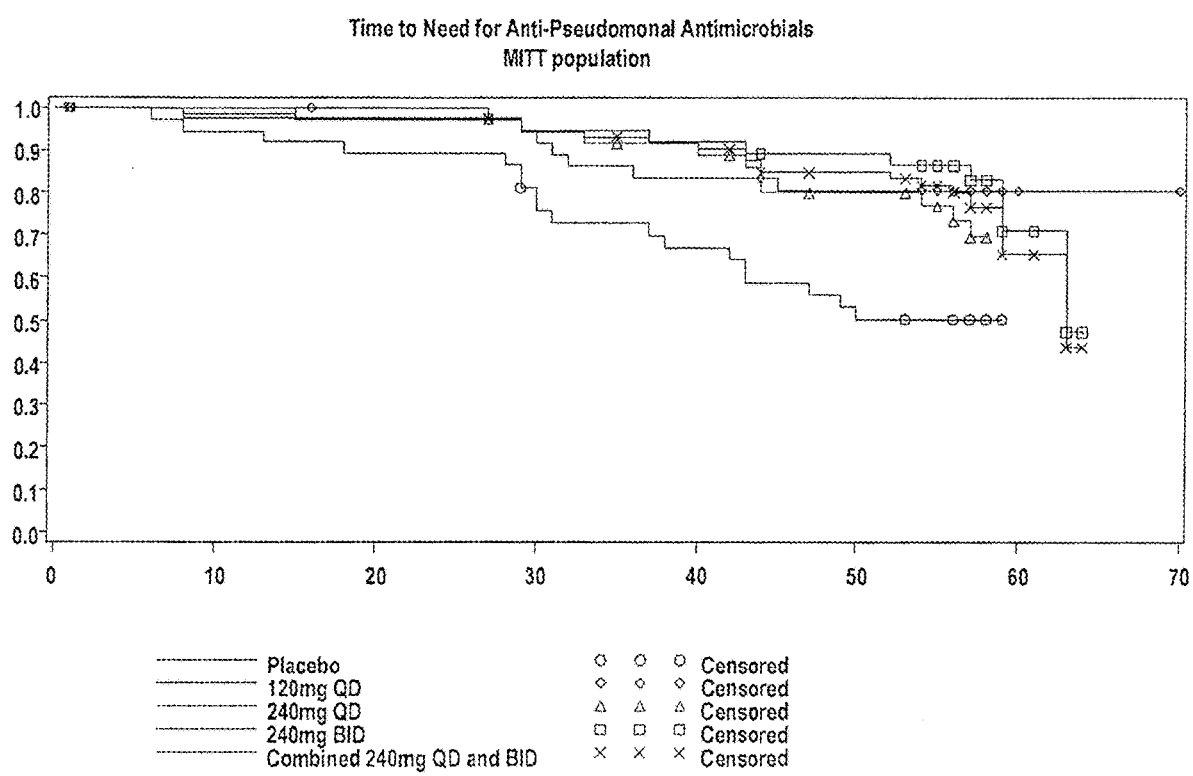

The measured need for additional anti-pseudomonal microbials was reduced in all levofloxacin treatment groups. In addition, significant hazard ratios were observed in all levofloxacin treatment groups. Hazard ratios are related to the relative risk that an event may occur. The hazard ratios were 0.29 for the levofloxacin 120 mg QD group, 0.39 for the levofloxacin 240 mg QD group, and 0.21 for the levofloxacin 240 mg BID group in the MITT Population compared to the placebo group, and were statistically significant compared to placebo. FIGS. 5 and 6 are plots of survival distribution function over time for each treatment group and show that the survival distribution function for patients treated with placebo begins to fall at a shorter time than patients treated with levofloxacin. In sum, at least 240 mg BID showed significant efficacy over placebo at Day 28 in time to need for anti-pseudomonal antimicrobials.

Pulmonary Function Evaluations

Figure 7:
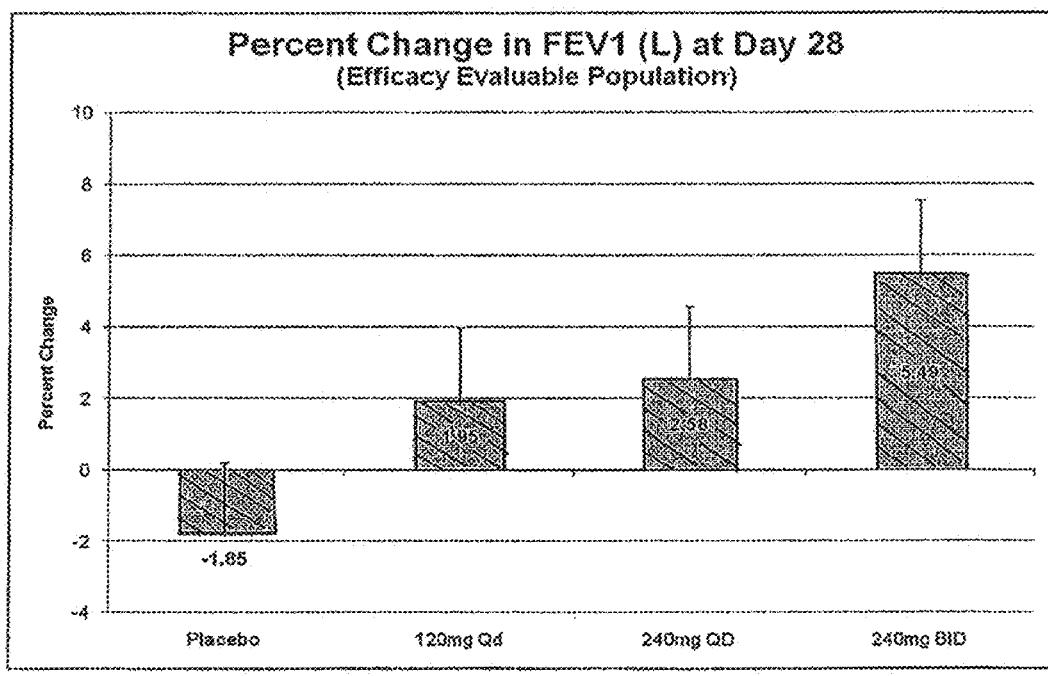
Figure 8:
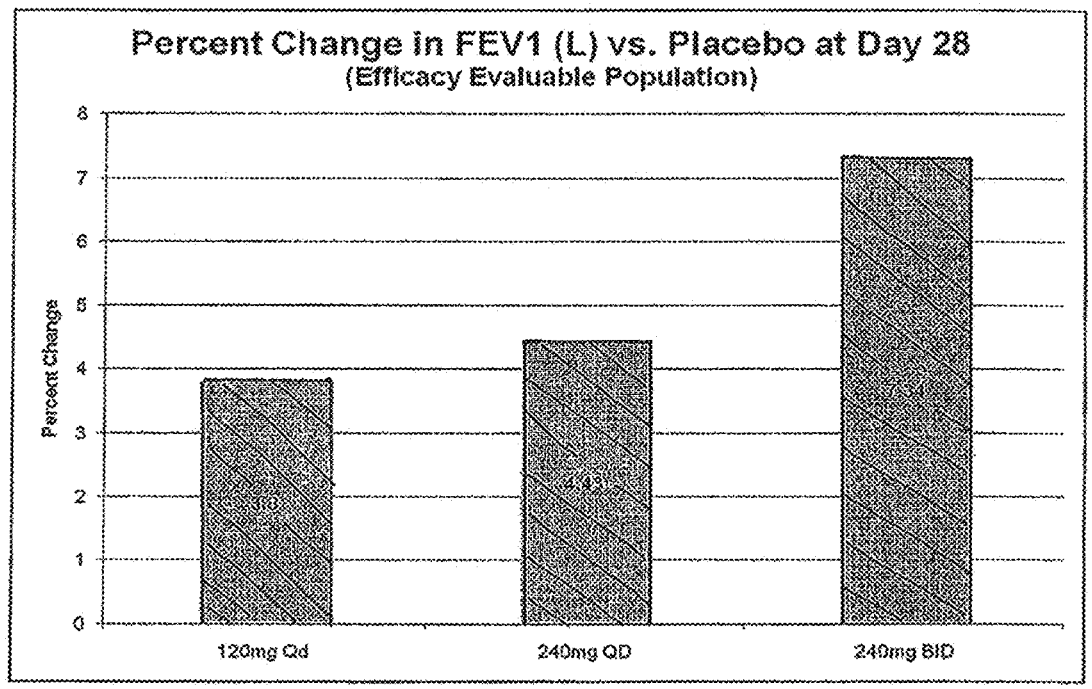
Figure 9:
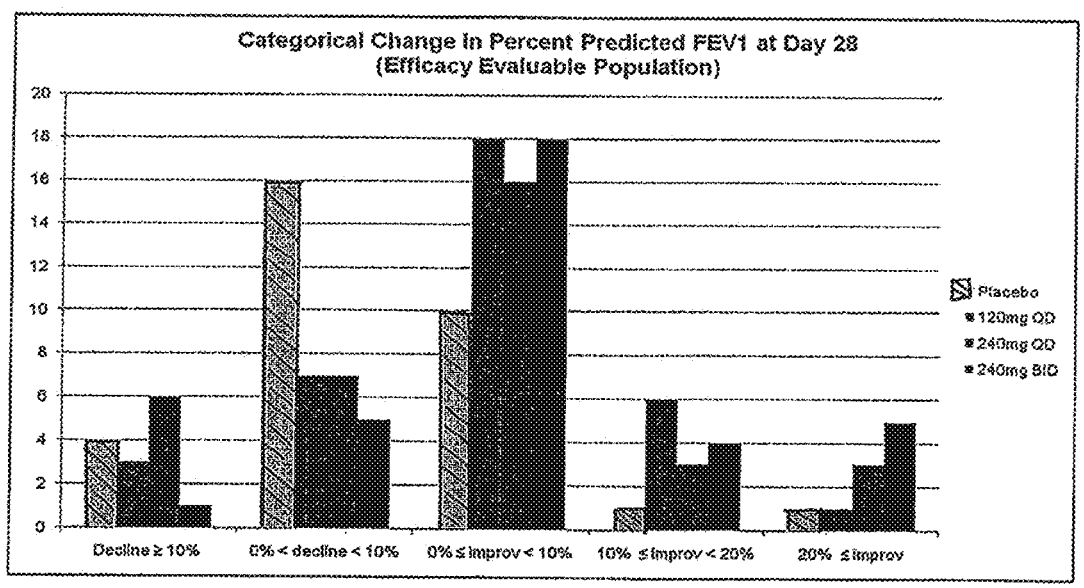

Changes in $FEV_1$ (forced expiratory volume in 1 second), FVC (forced vital capacity) and FEF 25-75 (forced expiratory flow 25-75%) from Day 1 to all subsequent visits were determined for patients. Tables 26 and 27 summarize the results for $FEV_1$ measurements in EE and MITT populations, respectively. FIGS. 7 and 8 show graphs of percent change in $FEV_1$ (L) and percent change in $FEV_1$(L) vs. placebo, respectively, at Day 28 for the EET population treated with placebo, 120 mg QD, 240 mg QD, or 240 mg BID. FIG. 9 shows a graph of the categorical change in percent predicted $FEV_1$ at Day 28 for the EET population treated with 120 mg QD, 240 mg QD, or 240 mg BID. Tables 28 and 29 summarize the results for predicted FEVI measurements in EE and MITT populations, respectively. Tables 30 and 31 summarize results for FEF 25-75 measurements in EE and MITT populations, respectively.

TABLE 26

EE population—Changes in $FEV_1$ values

|  |  | Placebo (N = 32) | Levofloxacin 120 mg. QD (N = 35) | Levofloxacin 240 mg QD (N = 35) | Levofloxacin 240 mg BID (N = 34) | Combined Levofloxacin 240 mg QD and BID (N = 69) |
|---|---|---|---|---|---|---|
| Day 1 | Mean | 1.98 | 1.99 | 2.09 | 1.86 | 1.98 |
|  | (SD) | (0.61) | (0.83) | (0.75) | (0.68) | (0.72) |
|  | Median | 2.01 | 1.87 | 2.02 | 1.70 | 1.81 |
| Day 14 | Mean | 1..97 | 2.00 | 2.16 | 2.02 | 2.09 |
|  | (SD) | (0.63) | (0.83) | (0.78) | (0.76) | (0.77) |
|  | Median | 1.93 | 1.82 | 2.09 | 1.88 | 2.03 |
| Percent Change from Baseline to Day 14 | Mean | −0.89 | 1.13 | 3.84 | 8.87 | 6.32 |
|  | (SD) | (6.86) | (7.48) | (10.23) | (12.42) | (11.56) |
|  | Median | −0.17 | 0.56 | 1.92 | 7.51 | 3.94 |
|  | P-value vs. Placebo |  | 0.4940 | 0.0737 | 0.001 | 0.0013 |
| Day 28 | Mean | 1.95 | 2.03 | 2.13 | 1.90 | 2.02 |
|  | (SD) | (0.65) | (0.89) | (0.76) | (0.68) | (0.73) |
|  | Median | 1.91 | 1.91 | 2.15 | 11.79 | 1.98 |
| Percent Change from Baseline to Day 28 | Mean | −2.55 | 1.71 | 2.51 | 5.05 | 3.75 |
|  | (SD) | (10.37) | (9.37) | (13.25) | (11.49) | (12.40) |
|  | Median | −3.91 | 1.06 | 1.28 | 4.55 | 2.80 |
|  | P-value vs. Placebo |  | 0.1726 | 0.1121 | 0.0102 | 0.0168 |

TABLE 27

MITT population—Changes in $FEV_1$ values

|  |  | Placebo (N = 37) | Levofloxacin 120 mg. QD (N = 38) | Levofloxacin 240 mg QD (N = 37) | Levofloxacin 240 mg BID (N = 39) | Combined Levofloxacin 240 mg QD and BID (N = 76) |
|---|---|---|---|---|---|---|
| Day 1 | Mean | 1.94 | 1.95 | 2.05 | 1.88 | 1.96 |
|  | (SD) | (0.61) | (0.81) | (0.75) | (0.68) | (0.71) |
|  | Median | 1.97 | 1.83 | 1.90 | 1.70 | 1.80 |
| Day 14 | Mean | 1.92 | 1.97 | 2.12 | 2.04 | 2.08 |
|  | (SD) | (0.63) | (0.81) | (0.78) | (0.77) | (0.77) |
|  | Median | 1.92 | 1.79 | 2.04 | 1.90 | 1.97 |
| Percent Change from Baseline to Day 14 | Mean | −1.21 | 1.87 | 3.81 | 9.34 | 6.61 |
|  | (SD) | (6.46) | (9.41) | (10.32) | (13.72) | (12.40) |
|  | Median | −0.90 | 0.56 | 1.92 | 7.51 | 3.94 |
|  | P-value |  | 0.2873 | 0.0497 | <.0001 | 0.0005 |
| Day 28 | Mean | 1.89 | 1.99 | 2.09 | 1.93 | 2.01 |
|  | (SD) | (0.64) | (0.88) | (0.76) | (0.69) | (0.73) |
|  | Median | 1.85 | 1.83 | 2.10 | 1.82 | 1.95 |
| Percent Change from Baseline to Day 28 | Mean | −2.96 | 1.92 | 2.35 | 5.93 | 4.14 |
|  | (SD) | (9.81) | (9.95) | (13.03) | (15.07) | (14.11) |
|  | Median | −3.92 | 1.60 | 1.28 | 3.55 | 2.50 |
|  | P-value |  | 0.1292 | 0.0831 | 0.0026 | 0.0063 |

TABLE 28

EE population—Changes in % predicted $FEV_1$

|  |  | Placebo (N = 32) | Levofloxacin 120 mg. QD (N = 35) | Levofloxacin 240 mg QD (N = 35) | Levofloxacin 240 mg BID (N = 34) | Combined Levofloxacin 240 mg QD and BID (N = 69) |
|---|---|---|---|---|---|---|
| Day 1 | Mean | 54.4 | 54.0 | 55.9 | 48.2 | 52.1 |
|  | (SD) | (12.93) | (17.79) | (14.60) | (14.88) | (15.13) |
|  | Median | 54.5 | 53.0 | 56.0 | 45.5 | 51.0 |
| Day 14 | Mean | 53.9 | 54.7 | 57.7 | 51.7 | 54.7 |
|  | (SD) | (13.21) | (17.61) | (15.19) | (16.93) | (16.23) |
|  | Median | 54.5 | 53.0 | 62.0 | 49.5 | 52.0 |
| Relative Percent Change from Baseline to Day 14 | Mean | −0.77 | 1.77 | 3.57 | 7.67 | 5.59 |
|  | (SD) | (6.85) | (6.08) | (10.75) | (14.70) | (12.92) |
|  | Median | 0.00 | 1.15 | 1.52 | 7.42 | 4.00 |
| Day 28 | Mean | 53.1 | 55.0 | 57.3 | 50.5 | 54.0 |
|  | (SD) | (14.05) | (19.30) | (15.52) | (15.36) | (15.71) |
|  | Median | 55.0 | 52.0 | 58.0 | 49.0 | 54.0 |
| Relative Percent Change from Baseline to Day 28 | Mean | −2.47 | 1.82 | 2.99 | 7.39 | 5.13 |
|  | (SD) | (10.34) | (9.81) | (14.54) | (17.48) | (16.06) |
|  | Median | −3.74 | 2.30 | 0.00 | 4.88 | 4.00 |
|  | P-value |  | 0.2655 | 0.1411 | 0.0034 | 0.0113 |

TABLE 29

MITT population—Changes in % predicted $FEV_1$

|  |  | Placebo (N = 37) | Levofloxacin 120 mg. QD (N = 38) | Levofloxacin 240 mg QD (N = 37) | Levofloxacin 240 mg BID (N = 39) | Combined Levofloxacin 240 mg QD and BID (N = 76) |
|---|---|---|---|---|---|---|
| Day 1 | Mean | 52.4 | 52.9 | 55.4 | 48.8 | 52.0 |
|  | (SD) | (13.42) | (17.68) | (14.41) | (15.15) | (15.07) |
|  | Median | 53.0 | 53.0 | 56.0 | 46.0 | 51.0 |
| Day 14 | Mean | 51.7 | 53.9 | 57.1 | 52.1 | 54.6 |
|  | (SD) | (13.84) | (17.42) | (14.96) | (17.16) | (16.20) |
|  | Median | 53.0 | 53.0 | 61.0 | 49.55555 | 52.0 |
|  | Mean | −0.68 | 0.81 | 1.70 | 3.66 | 2.69 |
|  | (SD) | (3.37) | (3.24) | (5.39) | (7.49) | (6.57) |
|  | Median | −1.00 | 1.00 | 1.00 | 2.50 | 2.00 |
| Relative Percent Change from Baseline to Day | Mean | −1.30 | 2.46 | 3.51 | 8.30 | 5.93 |
|  | (SD) | (6.58) | (8.47) | (10.83) | (15.80) | (13.70) |
|  | Median | −1.89 | 1.15 | 1.52 | 7.42 | 4.00 |
|  | P-value |  | 0.2284 | 0.0780 | 0.0005 | 0.0025 |
| Day 28 | Mean | 50.9 | 54.1 | 56.7 | 50.8 | 53.8 |
|  | (SD) | (14.46) | (19.19) | (15.33) | (15.40) | (15.54) |
|  | Median | 52.0 | 50.0 | 54.0 | 49.0 | 53.5 |
| Relative Percent Change from Baseline to Day 28 | Mean | −3.08 | 2.00 | 2.77 | 7.97 | 5.37 |
|  | (SD) | (9.82) | (10.07) | (14.30) | (19.49) | (17.18) |
|  | Median | 3.77 | 2.30 | 0.00 | 4.44 | 3.85 |
|  | P-value |  | 0.1759 | 0.0888 | 0.0008 | 0.0036 |

TABLE 30

EE population—Changes in FEF 25-75 values

|  |  | Placebo (N = 32) | Levofloxacin 120 mg. QD (N = 35) | Levofloxacin 240 mg QD (N = 35) | Levofloxacin 240 mg BID (N = 34) | Combined Levofloxacin 240 mg QD and BID (N = 69) |
|---|---|---|---|---|---|---|
| Day 1 | Mean | 1.02 | 1.17 | 1.22 | 0.85 | 1.04 |
|  | (SD) | (0.57) | (0.78) | (0.84) | (0.53) | (0.72) |
|  | Median | 0.94 | 0.98 | 1.10 | 0.68 | 0.83 |
| Day 14 | Mean | 1.03 | 1.18 | 1.33 | 1.00 | 1.17 |
|  | (SD) | (0.64) | (0.83) | (0.93) | (0.78) | (0.87) |
|  | Median | 0.86 | 0.99 | 1.11 | 0.78 | 0.92 |
| Percent Change from Baseline to Day 14 | Mean | 1.95 | 0.41 | 9.58 | 16.99 | 13.23 |
|  | (SD) | (19.45) | (12.28) | (21.16) | (32.60) | (27.45) |
|  | Median | −1.72 | 0.45 | 4.41 | 11.66 | 8.79 |
|  | P-value |  | 0.6634 | 0.2532 | 0.0072 | 0.0275 |
| Day 28 | Mean | 1.00 | 1.23 | 1.27 | 0.93 | 1.10 |
|  | (SD) | (0.64) | (0.93) | (0.88) | (0.59) | (0.77) |
|  | Median | 0.94 | 1.03 | 1.15 | 0.78 | 0.97 |
| Percent Change from Baseline to Day 28 | Mean | −2.73 | 0.73 | 4.70 | 13.11 | 8.78 |
|  | (SD) | (16.74) | (15.76) | (16.11) | (28.50) | (23.19) |
|  | Median | −4.61 | 2.70 | 5.77 | 5.71 | 5.74 |
|  | P-value |  | 0.6038 | 0.2223 | 0.0007 | 0.0076 |

TABLE 31

MITT population–Changes in FEF 25-75 values

|  |  | Placebo (N = 37) | Levofloxacin solution 120 mg. QD (N = 38) | Levofloxacin solution 240 mg QD (N = 37) | Levofloxacin solution 240 mg BID (N = 39) | Combined Levofloxacin solution 240 mg QD and BID (N = 76) |
|---|---|---|---|---|---|---|
| Day 1 | Mean | 0.98 | 1.12 | 1.18 | 0.87 | 1.02 |
|  | (SD) | (0.55) | (0.77) | (0.83) | (0.53) | (0.71) |
|  | Median | 0.92 | 0.89 | 1.09 | 0.68 | 0.83 |
| Day 14 | Mean | 0.97 | 1.15 | 1.29 | 1.01 | 1.15 |
|  | (SD) | (0.63) | (0.82) | (0.92) | (0.78) | (0.86) |
|  | Median | 0.81 | 0.85 | 1.08 | 0.78 | 0.90 |
| Percent Change from Baseline to Day 14 | Mean | −1.78 | 1.73 | 9.53 | 16.70 | 13.16 |
|  | (SD) | (22.86) | (13.76) | (20.70) | (31.72) | (26.92) |
|  | Median | −4.46 | 1.35 | 4.41 | 11.66 | 8.79 |
|  | P-value |  | 0.5910 | 0.0699 | 0.0007 | 0.0027 |
| Day 28 | Mean | 0.94 | 1.20 | 1.23 | 0.95 | 1.09 |
|  | (SD) | (0.62) | (0.92) | (0.87) | (0.61) | (0.76) |
|  | Median | 0.91 | 0.83 | 1.12 | 0.82 | 0.93 |
| Percent Change from Baseline to Day 28 | Mean | −6.40 | 1.94 | 5.02 | 14.19 | 9.611 |
|  | (SD) | (20.27) | (16.55) | (15.98) | (28.56) | (23.44) |
|  | Median | −8.66 | 3.38 | 5.77 | 7.46 | 5.88 |
|  | P-value |  | 0.1241 | 0.0489 | <.0001 | 0.0003 |

In the EE population, $FEV_1$ values for patients administered levofloxacin 240 mg BID increased from a median value of 1.70 L at Day 1 (baseline) to 1.79 L at Day 28, representing an increase in $FEV_1$ of approximately 5%. In patients administered levofloxacin 240 mg QD, $FEV_1$ values increased from a median value of 2.02 L on Day 1 to a median value of 2.15 L on Day 28, representing an increase in $FEV_1$ of approximately 6%. In patients administered levofloxacin 120 mg QD, $FEV_1$ values increased from a median value of 1.87 L on Day 1 to a median value of 1.91 L on Day 28, representing an increase in $FEV_1$ of approximately 2%. The largest differences for $FEV_1$ between patients administered placebo and patients administered levofloxacin were 0.16 L on Day 14, and 0.24 L on Day 28.

In the MITT population, $FEV_1$ values for patients administered levofloxacin 240 mg BID increased from a median value of 1.70 L at Day 1 (baseline) to 1.82 L at Day 28, representing an increase in $FEV_1$ of approximately 7%. In patients administered levofloxacin 240 mg QD, $FEV_1$ values increased from a median value of 1.90 L on Day 1 to a median value of 2.10 L on Day 28, representing an increase in FEVl of approximately 10%. The largest differences for $FEV_1$ between patients administered placebo and patients administered levofloxacin were 0.12 L on Day 14, and 0.25 L on Day 28.

FEF 25-75 values relate to the average flow of air coming out of the lungs during the middle portion of the expiration. In small airway diseases this value can be reduced. In the EE population, FEF 25-75 values for patients administered levofloxacin 240 mg BID increased from a median value of 0.68 at Day 1 (baseline) to 0.78 at Day 28, representing an increase in FEF 25-75 of approximately 15%. In patients administered levofloxacin 240 mg QD, FEF 25-75 values increased from a median value of 1.10 on Day 1 to a median value of 1.15 on Day 28, representing an increase in FEF 25-75 of approximately 4%. In patients administered levofloxacin 120 mg QD, FEF 25-75 values increased from a median value of 0.98 on Day 1 to a median value of 1.03 on Day 28, representing an increase in FEF 25-75 of approximately 5%. The largest differences for FEF 25-75 between patients administered placebo and patients administered levofloxacin were 0.25 L on Day 14, and 0.21 L on Day 28.

In the MITT population, FEF 25-75 values for patients administered levofloxacin 240 mg BID increased from a median value of 0.68 at Day 1 (baseline) to 0.82 at Day 28, representing an increase in FEF 25-75 of approximately 20%. In patients administered levofloxacin 240 mg QD, FEF 25-75 values increased from a median value of 1.09 on Day 1 to a median value of 1.12 on Day 28, representing an increase in FEF 25-75 of approximately 3%. The largest differences for FEF 25-75 between patients administered placebo and patients administered levofloxacin were 0.27 L on Day 14, and 0.21 L on Day 28.

Safety Evaluations

Adverse events and drug intolerability from Day 1 through the end of study were evaluated. No significant adverse events were reported.

Flouroquinolone-induced arthralgia and myalgia have been previously reported in the use of some fluoroquinolones, for example in the treatment of sinusitis (0-Lee T., et al "Fluoroquinolone-induced arthralgia and myalgia in the treatment of sinusitis" Am. J. Rhinol. (2005) 19:395-9, incorporated by reference in its entirety). In this study, Arthralgia was reported in 5.4% of patients administered with placebo. No arthralgia was reported in patients administered any levofloxacin formulations.

Example 3—Phase I Clinical Study in Pediatric CF Patients

Figure 10:
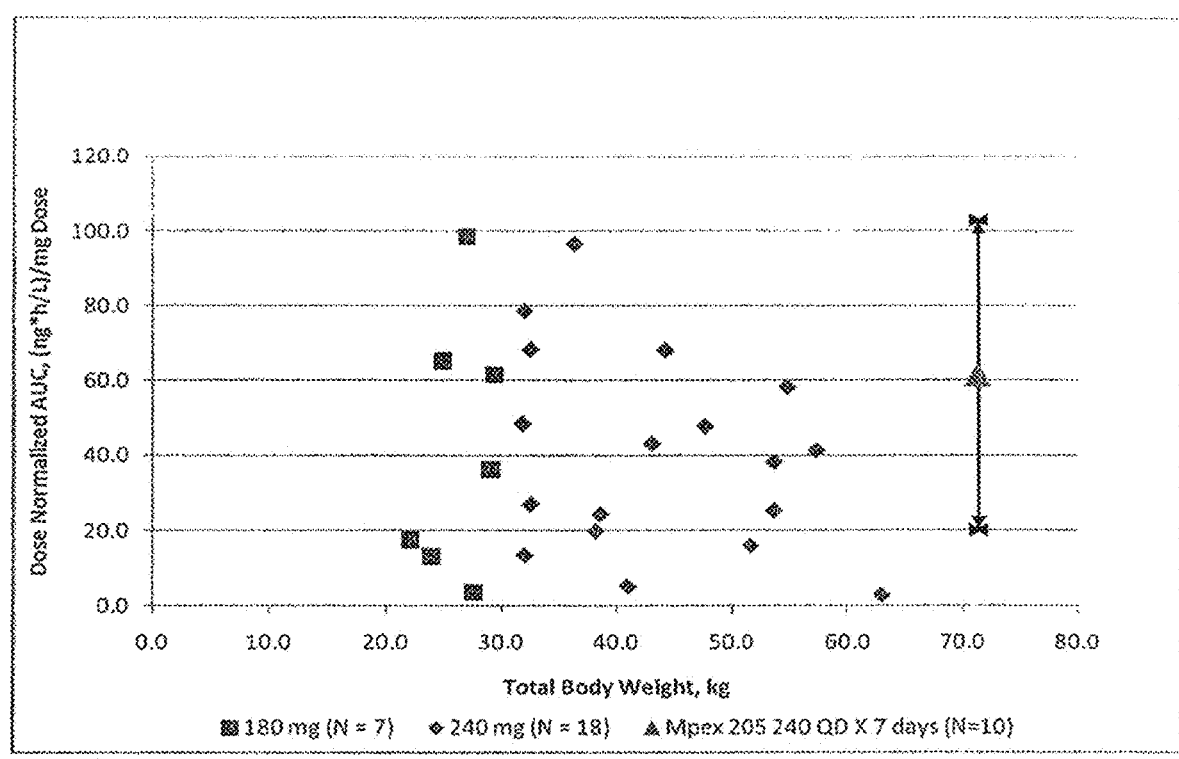

A Phase 1 multicenter, open-label study was carried out to evaluate the safety, tolerability and pharmacokinetics of weight-adjusted doses of levofloxacin formulated with $MgCl_2$ administered once daily for 14 days to stable pediatric CF patients. Patients were divided into 2 groups based on their age: 6-11 years of age and 12-16 years of age. The daily dose administered of levofloxacin formulated with $MgCl_2$ was divided as follows: patients that weighed 14-21 kg received a 120 mg dose, patients that weighed 22-30 kg received a 180 mg dose, and patients that weighed more than 30 kg received a 240 mg dose. A total of 27 patients were enrolled and all patients completed the study. There were 14 patients in the 6-11 years of age group and 13 patients in the 12-16 years of age group. Seven patients (all in the 6-11 age group) received 180 mg QD levofloxacin formulated with $MgCl_2$ and the remaining 20 patients received 240 mg QD levofloxacin formulated with $MgCl_2$. FIG. 10 shows a graph of dose normalized serum AUC in pediatric CF patients vs. patient body weight. FIGS. 11A-9B show graphs of dose normalized serum AUC in pediatric CF patients vs. patient age, and vs. BSA, respectively. FIGS. 11C-9E show graphs of dose normalized serum Cmax in pediatric CF patients vs. patient body weight, vs. patient age, and vs. BSA, respectively.

Serum levofloxacin exposures with either the 180 or 240 mg dose of levofloxacin formulated with $MgCl_2$ appear to be in the ranges observed in adults CF patients studied in a related clinical trial (data not shown).

Example 4—Phase III Clinical Study

A Phase 3, multi-center, multinational, randomized, double-blind, placebo-controlled study to evaluate the efficacy and safety of levofloxacin formulated with $MgCl_2$ in stable CF patients is performed. Following a 14-day screening period, patients are randomized at Visit 1/Day 1 in a 2:1 ratio to receive levofloxacin formulated with $MgCl_2$ or placebo. Randomization is stratified by geographic region (US vs. non-US), age (12-18 years vs. >18 years of age) and by $FEV_1$ percent predicted (<55% vs. >55%). Patients receive 28 days of either levofloxacin formulated with $MgCl_2$ or placebo followed by 28 days of observation. Patients should remain off anti-pseudomonal antimicrobials, other than Study Drug (levofloxacin formulated with $MgCl_2$ or placebo) and maintenance oral azithromycin (if applicable), for the duration of the study unless they meet the protocol defined definition of an exacerbation or unless determined to be necessary for safety reasons by the Investigators. The end of the study is defined as the last visit of the last patient.

Levofloxacin formulated with $MgCl_2$ (levofloxacin inhalation solution, Aeroquin™) will be provided in single use ampules ready for administration. Each ampule contains 240 mg of levofloxacin formulated with $MgCl_2$ in 2.4 mL (100 mg/mL). A 240 mg dose (1 ampule) is administered using a PART investigational eFlow® nebulizer twice daily (BID) approximately 8-12 hours apart. Placebo is riboflavin 5'-phosphate (solubilized form of vitamin B2) in 0.9% saline provided in single use ampules ready for administration. Each ampule contains 9.6 lag of riboflavin 5'-phosphate in a volume of 2.4 mL. A PART investigational eFlow® nebulizer is optimized and customized for use only with levofloxacin formulated with $MgCl_2$. Both levofloxacin formulated with $MgCl_2$ and the placebo control are administered using this nebulizer system. Analysis populations include: (1) safety/modified intent to treat (MITT) population (all patients enrolled in the study who receive at least one dose of Study Drug (levofloxacin formulated with $MgCl_2$ or placebo); (2) efficacy evaluable Population (all patients enrolled in the study, without major protocol violations, who receive at least 80% of Study Drug (levofloxacin formulated with $MgCl_2$/placebo) doses); and (3) pharmacokinetic population (all patients who receive a least one dose of Study Drug (levofloxacin formulated with $MgCl_2$/placebo) and have at least one pharmacokinetic (PK) blood or sputum sample collected).

Inclusion criteria for study patients included: at least 12 years of age; weigh at least 30 kg or 66 pounds; and have documented CF diagnosis as evidenced by one or more clinical features consistent with the CF phenotype. Exclusion criteria for study patients included: use of an investigational agent within 28 days prior to Visit 1; use of any nebulized or systemic antimicrobials active against *P. aeruginosa* within 28 days prior to Visit 1, other than maintenance oral azithromycin, which must have been initiated at least 28 days prior to Visit 1; and use of oral corticosteroids in doses exceeding the equivalent of 10 mg prednisone/day or 20 mg prednisone every other day at Screening or Visit 1.

Primary Efficacy Evaluations

The primary endpoint includes the time (in days) to an exacerbation from Baseline (Visit 1/Day 1) until Final Visit. To meet the endpoint a patient must concurrently meet 4 of the 12 symptoms/signs that make up the Fuchs definition of an exacerbation (Fuchs H J, et al. Effect of aerosolized recombinant human DNase on exacerbations of respiratory symptoms and on pulmonary function in patients with cystic fibrosis. N Engl J Med 1994; 331:637-642, incorporated by reference in its entirety).

The 12 symptoms/signs defined by the Fuchs criteria include: change in sputum; new or increased hemoptysis; increased cough; increased dyspnea; malaise, fatigue or lethargy; temperature above 38° C.; anorexia or weight loss; sinus pain or tenderness; change in sinus discharge; change in physical examination of the chest; decrease in pulmonary function by 10% or more from a previously recorded value; and radiographic changes indicative of pulmonary infection. The above symptoms associated with an exacerbation are recorded from each patient using a standardized questionnaire, the Respiratory and Systemic Symptoms Questionnaire (RSSQ) at patient visits. Changes the patient experiences are relative to what the patient considers normal on a day-to-day basis. It is anticipated that patients administered aerosolized levofloxacin formulated with $MgCl_2$ provide the following signs/symptoms that are included in the Fuchs criteria and that are recorded using the RSSQ: (1) Increased sputum production: patients have no change, a little less or much less amounts of sputum when coughing up. (2) Change in sputum appearance: for sputum thickness, patients have a little thinner or much thinner sputum; for sputum color, patients have a better color of sputum (better increases from brown→green→yellow→clear). (3) Increased chest congestion: patients have a little decrease, or a large decrease in chest congestion. (4) New or increased coughing up of blood: patients have a little decrease or a large decrease in the amount of blood coughed up. (5) Increased cough: for intensity of cough, patients have a little lighter, or much lighter coughs; for frequency of cough, patients cough a little less often or much less often. (6) Decreased exercise tolerance: patients perform daily activities, e.g., climbing stairs, a little easier, or much easier. (7) Increased dyspnea with exertion: patients breathe a little easier or much easier when performing daily activities. (8) Malaise, fatigue or lethargy: patients have a little more energy or much more energy since last visit. (9) Fever: patients have no fever since last visit. (10) Weight loss:

patients have no change in weight, or a little weight gain. (11) Sinus pain and tenderness: patient has no pain or tenderness. (12) Change in sinus discharge: patient has better sinus discharge (a decrease in thickness and/or better color). (13) School or work absenteeism (due to illness): patient has no absenteeism from schedules activities. (14) Decreased appetite: patient has a little increase in appetite.

Secondary Efficacy Evaluations

Secondary Endpoints include clinical, pulmonary function, microbiology, and patient reported outcome characteristics.

Clinical Characteristics

Clinical characteristics include the time (in days) to administration of systemic (oral or IV) and/or inhaled anti-pseudomonal antimicrobials from Baseline (Visit 1/Day 1) until Final Visit. To meet this endpoint, patients must have at least one of four worsening respiratory symptoms (increased cough, increased sputum/chest congestion, decreased exercise tolerance, decreased appetite) at the time of administration of the anti-pseudomonal antimicrobial agent. Clinical characteristics also include the proportion of patients who miss at least 1 day of school/work secondary to worsening respiratory status.

It is anticipated that patients administered aerosolized levofloxacin formulated with $MgCl_2$ have an increased time to administration of systemic (oral or IV) and/or inhaled anti-pseudomonal antimicrobials from Baseline (Visit 1/Day 1) until Final Visit compared to patients administered placebo. In addition, the proportion of patients administered aerosolized levofloxacin formulated with $MgCl_2$ who miss at least 1 day of school/work secondary to worsening respiratory status is less than the proportion of patients administered placebo who miss at least 1 day of school/work secondary to worsening respiratory status.

Pulmonary Function Characteristics

Pulmonary function characteristics include: percent change in $FEV_1$ (L) from Baseline to Day 28; relative change in $FEV_1$ (percent predicted) from Baseline to Day 28; percent change in FEF25-75 (L/s) from Baseline to Day 28; percent change in FVC (L) from Baseline to Day 28; and categorical assessment of percent change in $FEV_1$(L) and relative change in percent predicted $FEV_1$ from Baseline to Day 28.

It is anticipated that patients administered aerosolized levofloxacin formulated with $MgCl_2$ have more advantageous pulmonary function characteristics compared to patients administered placebo.

Microbiology Characteristics

Microbiology characteristics include: change in *P. aeruginosa* density (log 10 colony-forming units [CFU] per gram sputum) from Baseline to Day 28; categorical assessment of change in *P. aeruginosa* density (log 10 colony-forming units [CFU] per gram sputum) from Baseline to Day 28; and change in *Stenotrophomonas* sp., *Achromobacter* sp., *Burkholderia* sp. and *S. aureus* density (log 10 colony-forming units [CFU] per gram sputum) from Baseline to Day 28.

It is anticipated that patients administered aerosolized levofloxacin formulated with $MgCl_2$ have more advantageous microbiology characteristics, e.g., decreased *P. aeruginosa* sputum density, decreased *Stenotrophomonas* sp., *Achromobacter* sp., *Burkholderia* sp. and *S. aureus* sputum density, compared to patients administered placebo.

Patient Reported Outcome Characteristics

Patient reported outcome characteristics include: change in the respiratory domain of the CFQ-R from Baseline to Day 28; and categorical assessment of change in the respiratory domain of the CFQ-R from Baseline to Day 28.

It is anticipated that patients administered aerosolized levofloxacin formulated with $MgCl_2$ have more advantageous patient reported outcome characteristics than patients administered placebo.

Example 5—In Vivo Antibacterial Activity of Levofloxacin Inhalation Solution Against *Burkholderia cepacia*

*Burkholderia cepacia* is an opportunistic pathogen capable of causing pulmonary infection in CF patients. Infections with certain strains of *B. cepacia* cause "cepacia syndrome" which is characterized by progressive and invasive necrotizing pneumonia and septicemia. Most *B. cepacia* have high MICs to many antibiotics. Aerosolized levofloxacin formulated with $MgCl_2$ enables aerosol delivery of high drug concentrations to the lung.

Five *B. cepacia* strains with levofloxacin MICs ranging between 0.25-8 mg/L were tested in a mouse model of pulmonary infection. Female BALB/c mice were injected with 150 mg/kg of cyclophosphamide 3 days prior to infection. On day 4, the mice were infected with 50 ul of bacterial suspension (~$10^6$ CFU/ml) using a curved bead-tipped oral gavage syringe under isoflurane anesthesia. Treatment with levofloxacin formulated with $MgCl_2$ (60 mg/kg BID) or saline only was initiated 72 hours post-infection and continued twice daily for four days using a microspray aerosol device. Sixteen hours after the last treatment, mice were sacrificed, lungs harvested, homogenized, and plated to determine colony counts (CFU).

As part of a Phase 2b trial of aerosolized levofloxacin formulated with $MgCl_2$ in CF patients, a 16 year old male patient infected with *B. cepacia* (levofloxacin MIC=>128 mg/L) received levofloxacin formulated with $MgCl_2$ 240 mg QD for 28 days.

Aerosolized levofloxacin formulated with $MgCl_2$ produced at least one log CFU of bacterial killing for all strains in the mouse infection model (Table 32). In the CF patient, a 1.7 log CFU decrease in bacterial counts was observed over 28 days.

TABLE 32

| Strains | Genomovar II | | | Genomovar III | |
|---|---|---|---|---|---|
| | BC1012 | BC1013 | BC1014 | BC1020 | BC1021 |
| MIC (mg/L) | 4 | 0.25 | 1 | 8 | 8 |
| Mean Change in Log CFU/Lungs | −1.03 | −2.08 | −1.47 | −1.11 | −1.35 |

An increase in the CF patient's $FEV_1$ was observed. On day 1 of the study, the patient's $FEV_1$ was 1.21 L, this increased to 1.30 L on day 28, a 7% improvement. From a population model, Cmax and AUC values were calculated to be approximately 12,900 mg/L and 4,400 mg*h/L, respectively.

Aerosol administration of levofloxacin formulated with $MgCl_2$ produced significant bacterial killing in strains with a wide range of MICs. The non-clinical and clinical data support the future clinical evaluation of levofloxacin formulated with $MgCl_2$ in the management of chronic pulmonary infections due to *B. cepacia*.

To the extent publications and patents or patent applications incorporated by reference herein contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein.

Terms and phrases used in this application, and variations thereof, unless otherwise expressly stated, should be construed as open ended as opposed to limiting. As examples of the foregoing, the term 'including' should be read to mean 'including, without limitation' or the like; the term 'comprising' as used herein is synonymous with 'including,' 'containing,' or 'characterized by,' and is inclusive or open-ended and does not exclude additional, unrecited elements or method steps: the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise. In addition, as used in this application, the articles 'a' and 'an' should be construed as referring to one or more than one (i.e., to at least one) of the grammatical objects of the article. By way of example, 'an element' means one element or more than one element.

The presence in some instances of broadening words and phrases such as 'one or more', 'at least', 'but not limited to', or other like phrases shall not be read to mean that the narrower case is intended or required in instances where such broadening phrases may be absent.

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method for treating a pulmonary infection, wherein the pulmonary infection comprises one or more *Mycobacterium*, the method comprising:
   administering via inhalation 240 mg of levofloxacin twice daily for 28 days to the human having cystic fibrosis to treat the *Mycobacterium* pulmonary infection;
   wherein the levofloxacin is in an aerosol of a solution comprising levofloxacin at a concentration from about 90 mg/ml to about 110 mg/ml, a magnesium cation at a concentration from about 175 mM to about 225 mM, wherein the solution has a pH from about 5 to about 7, and an osmolality from about 300 mOsmol/kg to about 500 mOsmol/kg.

2. The method of claim 1, wherein the *Mycobacterium* is *Mycobacterium tuberculosis*, *Mycobacterium avium*, *Mycobacterium intracellulare*, or *Mycobacterium leprae*.

3. The method of claim 2, wherein the *Mycobacterium* is *Mycobacterium avium* or *Mycobacterium intracellulare*.

4. The method of claim 1, wherein the magnesium cation is in the form of magnesium chloride.

5. The method of claim 1, wherein the solution comprises a levofloxacin concentration of about 100 mg/ml, a magnesium chloride concentration of about 200 mM, a pH between about 6.0 to about 6.5, and an osmolality of between about 300 mOsmol/kg to about 500 mOsmol/kg, and lacks lactose.

6. The method of claim 1, wherein the aerosol of the solution comprises a mass median aerodynamic diameter from about 2 microns to about 5 microns with a geometric standard deviation less than or equal to 2.5 microns.

7. The method of claim 1, wherein the aerosol is produced by a vibrating mesh nebulizer.

8. The method of claim 1, further comprising administering an antibiotic, a bronchodilator, an anticholinergic agent, a glucocorticoid, an eicosanoid inhibitor, or a combination of two or more thereof.

* * * * *